United States Patent
Drew et al.

(10) Patent No.: US 9,731,007 B2
(45) Date of Patent: Aug. 15, 2017

(54) TUMOUR NECROSIS FACTOR RECEPTOR FUSION PROTEINS AND METHODS OF USING THE SAME

(71) Applicant: NEXVET AUSTRALIA PTY LTD, Melbourne (AU)

(72) Inventors: Alexander Drew, Kensington (AU); David Gearing, Melbourne (AU)

(73) Assignee: Nexvet Australia Pty Ltd, Melbourne (AU)

( * ) Notice: Subject to any disclaimer, the term of this patent is extended or adjusted under 35 U.S.C. 154(b) by 231 days.

(21) Appl. No.: 14/380,277

(22) PCT Filed: Feb. 22, 2013

(86) PCT No.: PCT/GB2013/050433
§ 371 (c)(1),
(2) Date: Aug. 21, 2014

(87) PCT Pub. No.: WO2013/124666
PCT Pub. Date: Aug. 29, 2013

(65) Prior Publication Data
US 2015/0037333 A1    Feb. 5, 2015

Related U.S. Application Data

(60) Provisional application No. 61/601,712, filed on Feb. 22, 2012.

(51) Int. Cl.
| | | |
|---|---|---|
| A61K 39/395 | (2006.01) | |
| A61K 38/17 | (2006.01) | |
| C07K 14/715 | (2006.01) | |
| C07K 16/00 | (2006.01) | |
| A61K 45/06 | (2006.01) | |
| C07K 14/705 | (2006.01) | |

(52) U.S. Cl.
CPC ...... *A61K 39/3955* (2013.01); *A61K 38/1793* (2013.01); *A61K 45/06* (2013.01); *C07K 14/70578* (2013.01); *C07K 14/7151* (2013.01); *C07K 16/00* (2013.01); *C07K 2319/30* (2013.01)

(58) Field of Classification Search
CPC ............ A61K 39/3955; A61K 38/1793; C07K 14/7151
See application file for complete search history.

(56) References Cited

FOREIGN PATENT DOCUMENTS

| WO | WO 2006/105344 A2 | 10/2006 |
| WO | WO-2010/027488 A2 | 3/2010 |
| WO | WO 2010/117488 A2 | 10/2010 |
| WO | WO-2010/136480 | 12/2010 |

OTHER PUBLICATIONS

Glabinski et al., "Treatment with Soluble Tumor Necrosis Factor Receptor (sTNFR): Fc/p80 Fusion Protein Ameliorates Relapsing-remitting Experimental Autoimmune Encephalomyelitis and Decreases Chemokine Expression," Autoimmunity, vol. 37 (6/7), pp. 465-471, Sep./Nov. 2004.
Database UniProt, "SubName: Full=Uncharacterized protein; Flags: Fragment;", XP002698800, retrieved from EBI accession No. UNIPROT:F1P971, dated May 3, 2011 (1 page).
International Search Report dated Jul. 26, 2013 issued in PCT/GB2013/050433.
Karampetsou et al., "TNF—antagonists beyond approved indications: stories of success prospects for the future", Q J Med, vol. 103, No. 12, pp. 917-928, dated Aug. 27, 2010.
Written Opinion dated Jul. 26, 2013 issued in PCT/GB2013/050433.
Staten, "LIB3731-005-Q6-K1-C9 Canis lupus familiaris cDNA clone CLN2602209 MRNA sequence," NCBI GenBank: DN368636.1, Mar. 4, 2005.

*Primary Examiner* — Ruixiang Li
(74) *Attorney, Agent, or Firm* — Foley & Lardner LLP

(57) ABSTRACT

A chimeric fusion polypeptide is provided comprising an extracellular domain of a canine TNF receptor p60 or p80 polypeptide conjoined to an Fc region of a canine IgG immunoglobulin heavy chain. The chimeric fusion polypeptide may be used in the treatment or prevention of conditions in canines mediated by TNF expression.

14 Claims, 21 Drawing Sheets

MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGST

Figure 1: SEQ ID NO:1 – Canine TNFR p60 ECD amino acid sequence

FNECRCTDTPPCPVPEPLGGPSVLIFPPKPKDILRITRTPEVTCVV
LDLGREDPEVQISWFVDGKEVHTAKTQSREQQFNGTYRVVSVLPIE
HQDWLTGKEFKCRVNHIDLPSPIERTISKARGRAHKPSVYVLPPSP
KELSSSDTVSITCLIKDFYPPDIDVEWQSNGQQEPERKHRMTPPQL
DEDGSYFLYSKLSVDKSRWQQGDPFTCAVMHETLQNHYTDLSLSHS
PGK

Figure 2: SEQ ID NO:2 – Canine IgG HCA heavy chain

```
PKRENGRVPRPPDCPKCPAPEMLGGPSVFIFPPKPKDTLLIARTPE
VTCVVVDLDPEDPEVQISWFVDGKQMQTAKTQPREEQFNGTYRVVS
VLPIGHQDWLKGKQFTCKVNNKALPSPIERTISKARGQAHQPSVYV
LPPSREELSKNTVSLTCLIKDFYPPDIDVEWQSNGQQEPESKYRTT
PPQLDEDGSYFLYSKLSVDKSRWQRGDTFICAVMHEALHNHYTQES
LSHSPGK
```

Figure 3: SEQ ID NO:3 – Canine IgG HCB heavy chain

```
AKECECKCNCNNCPCPGCGLLGGPSVFIFPPKPKDILVTARTPTVT
CVVVDLDPENPEVQISWFVDSKQVQTANTQPREEQSNGTYRVVSVL
PIGHQDWLSGKQFKCKVNNKALPSPIEEIISKTPGQAHQPNVYVLP
PSRDEMSKNTVTLTCLVKDFFPPEIDVEWQSNGQQEPESKYRMTPP
QLDEDGSYFLYSKLSVDKSRWQRGDTFICAVMHEALHNHYTQISLS
HSPGK
```

Figure 4: SEQ ID NO:4 – Canine IgG HCC heavy chain

```
PKESTCKCISPCPVPESLGGPSVFIFPPKPKDILRITRTPEITCVV
LDLGREDPEVQISWFVDGKEVHTAKTQPREQQFNSTYRVVSVLPIE
HQDWLTGKEFKCRVNHIGLPSPIERTISKARGQAHQPSVYVLPPSP
KELSSSDTVTLTCLIKDFYPPEIDVEWQSNGQPEPESKYHTTAPQL
DEDGSYFLYSKLSVDKSRWQQGDTFTCAVMHEALQNHYTDLSLSHS
PGK
```

Figure 5: SEQ ID NO:5 – Canine IgG HCD heavy chain

```
MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGSTFNECRCTDTPPCPVPEPLG
GPSVLIFPPKPKDILRITRTPEVTCVVLDLGREDPEVQISWFVDGK
EVHTAKTQSREQQFNGTYRVVSVLPIEHQDWLTGKEFKCRVNHIDL
PSPIERTISKARGRAHKPSVYVLPPSPKELSSSDTVSITCLIKDFY
PPDIDVEWQSNGQQEPERKHRMTPPQLDEDGSYFLYSKLSVDKSRW
QQGDPFTCAVMHETLQNHYTDLSLSHSPGK**
```

Figure 6: SEQ ID NO:6 – caTNFR:HCA Fc Fusion Polypeptide

```
MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGSTPKRENGRVPRPPDCPKCPA
PEMLGGPSVFIFPPKPKDTLLIARTPEVTCVVVDLDPEDPEVQISW
FVDGKQMQTAKTQPREEQFNGTYRVVSVLPIGHQDWLKGKQFTCKV
NNKALPSPIERTISKARGQAHQPSVYVLPPSREELSKNTVSLTCLI
KDFYPPDIDVEWQSNGQQEPESKYRTTPPQLDEDGSYFLYSKLSVD
KSRWQRGDTFICAVMHEALHNHYTQESLSHSPGK**
```

Figure 7: SEQ ID NO:7 – caTNFR:HCB Fc Fusion Polypeptide

```
MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGSTAKECECKCNCNNCPCPGCG
LLGGPSVFIFPPKPKDILVTARTPTVTCVVVDLDPENPEVQISWFV
DSKQVQTANTQPREEQSNGTYRVVSVLPIGHQDWLSGKQFKCKVNN
KALPSPIEEIISKTPGQAHQPNVYVLPPSRDEMSKNTVTLTCLVKD
FFPPEIDVEWQSNGQQEPESKYRMTPPQLDEDGSYFLYSKLSVDKS
RWQRGDTFICAVMHEALHNHYTQISLSHSPGK**
```

Figure 8: SEQ ID NO:8 – caTNFR:HCC Fc Fusion Polypeptide

```
MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGSTPKESTCKCISPCPVPESLG
GPSVFIFPPKPKDILRITRTPEITCVVLDLGREDPEVQISWFVDGK
EVHTAKTQPREQQFNSTYRVVSVLPIEHQDWLTGKEFKCRVNHIGL
PSPIERTISKARGQAHQPSVYVLPPSPKELSSSDTVTLTCLIKDFY
PPEIDVEWQSNGQPEPESKYHTTAPQLDEDGSYFLYSKLSVDKSRW
QQGDTFTCAVMHEALQNHYTDLSLSHSPGK**
```

Figure 9: SEQ ID NO:9 – caTNFR:HCD Fc Fusion Polypeptide

```
MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGSTFNECRCTDTPPCPVPEPLG
GPSVLIFPPKPKDILRITRTPEVTCVVLDLGREDPEVQISWFVDGK
EVHTAKTQSREQQFAGTYRVVSVLPIEHQDWLTGKEFKCRVNHIDL
PSPIERTISKARGRAHKPSVYVLPPSPKELSSSDTVSITCLIKDFY
PPDIDVEWQSNGQQEPERKHRMTPPQLDEDGSYFLYSKLSVDKSRW
QQGDPFTCAVMHETLQNHYTDLSLSHSPGK**
```

Figure 10: SEQ ID NO:10 – caTNFR:HCA Aglycosyl Fc Fusion Polypeptide

```
MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGSTPKRENGRVPRPPDCPKCPA
PEMLGGPSVFIFPPKPKDTLLIARTPEVTCVVVDLDPEDPEVQISW
FVDGKQMQTAKTQPREEQFAGTYRVVSVLPIGHQDWLKGKQFTCKV
NNKALPSPIERTISKARGQAHQPSVYVLPPSREELSKNTVSLTCLI
KDFYPPDIDVEWQSNGQQEPESKYRTTPPQLDEDGSYFLYSKLSVD
KSRWQRGDTFICAVMHEALHNHYTQESLSHSPGK**
```

Figure 11: SEQ ID NO:11 – caTNFR:HCB Aglycosyl Fc Fusion Polypeptide

```
MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGSTAKECECKCNCNNCPCPGCG
LLGGPSVFIFPPKPKDILVTARTPTVTCVVVDLDPENPEVQISWFV
DSKQVQTANTQPREEQSAGTYRVVSVLPIGHQDWLSGKQFKCKVNN
KALPSPIEEIISKTPGQAHQPNVYVLPPSRDEMSKNTVTLTCLVKD
FFPPEIDVEWQSNGQQEPESKYRMTPPQLDEDGSYFLYSKLSVDKS
RWQRGDTFICAVMHEALHNHYTQISLSHSPGK**
```

Figure 12: SEQ ID NO:12 – caTNFR:HCC Aglycosyl Fc Fusion Polypeptide

```
MGLPTVPGLLLPLVLLALLLEIYPISVTALVPHPRNRVKRAILCPQ
GKYIHPQDDSICCTKCHKGTYLYNDCPGPGLDTDCRECENGTFTAS
ENHLRQCLSCSKCRKEMNQVEISPCTVYRDTVCGCRKNQYRFYWSE
TLFQCNNCSLCLNGTVQISCQEKQNTICTCHAGFFLREHECVSCVN
CKKNTECGKLCLPPVETVKVPQDPGSTPKESTCKCISPCPVPESLG
GPSVFIFPPKPKDILRITRTPEITCVVLDLGREDPEVQISWFVDGK
EVHTAKTQPREQQFASTYRVVSVLPIEHQDWLTGKEFKCRVNHIGL
PSPIERTISKARGQAHQPSVYVLPPSPKELSSSDTVTLTCLIKDFY
PPEIDVEWQSNGQPEPESKYHTTAPQLDEDGSYFLYSKLSVDKSRW
QQGDTFTCAVMHEALQNHYTDLSLSHSPGK**
```

Figure 13: SEQ ID NO:13 – caTNFR:HCD Aglycosyl Fc Fusion Polypeptide

MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGD

Figure 14: SEQ ID NO:14 – Canine TNFR p80 signal sequence and ECD

MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGDFNECRCTDTPPCPVPE
PLGGPSVLIFPPKPKDILRITRTPEVTCVVLDLGREDPEVQISWFV
DGKEVHTAKTQSREQQFNGTYRVVSVLPIEHQDWLTGKEFKCRVNH
IDLPSPIERTISKARGRAHKPSVYVLPPSPKELSSSDTVSITCLIK
DFYPPDIDVEWQSNGQQEPERKHRMTPPQLDEDGSYFLYSKLSVDK
SRWQQGDPFTCAVMHETLQNHYTDLSLSHSPGK**

Figure 15: SEQ ID NO:15 – caTNFrecp80-HCA Fusion Polypeptide

```
MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGDPKRENGRVPRPPDCPK
CPAPEMLGGPSVFIFPPKPKDTLLIARTPEVTCVVVDLDPEDPEVQ
ISWFVDGKQMQTAKTQPREEQFNGTYRVVSVLPIGHQDWLKGKQFT
CKVNNKALPSPIERTISKARGQAHQPSVYVLPPSREELSKNTVSLT
CLIKDFYPPDIDVEWQSNGQQEPESKYRTTPPQLDEDGSYFLYSKL
SVDKSRWQRGDTFICAVMHEALHNHYTQESLSHSPGK**
```

Figure 16: SEQ ID NO:16 – caTNFrecp80-HCB Fusion Polypeptide

```
MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGDAKECECKCNCNNCPCP
GCGLLGGPSVFIFPPKPKDILVTARTPTVTCVVVDLDPENPEVQIS
WFVDSKQVQTANTQPREEQSNGTYRVVSVLPIGHQDWLSGKQFKCK
VNNKALPSPIEEIISKTPGQAHQPNVYVLPPSRDEMSKNTVTLTCL
VKDFFPPEIDVEWQSNGQQEPESKYRMTPPQLDEDGSYFLYSKLSV
DKSRWQRGDTFICAVMHEALHNHYTQISLSHSPGK**
```

Figure 17: SEQ ID NO:17 – caTNFrecp80-HCC Fc Fusion Polypeptide

MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGDPKESTCKCISPCPVPE
SLGGPSVFIFPPKPKDILRITRTPEITCVVLDLGREDPEVQISWFV
DGKEVHTAKTQPREQQFNSTYRVVSVLPIEHQDWLTGKEFKCRVNH
IGLPSPIERTISKARGQAHQPSVYVLPPSPKELSSSDTVTLTCLIK
DFYPPEIDVEWQSNGQPEPESKYHTTAPQLDEDGSYFLYSKLSVDK
SRWQQGDTFTCAVMHEALQNHYTDLSLSHSPGK**

Figure 18: SEQ ID NO:18 – caTNFrecp80-HCD Fc Fusion Polypeptide

MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGDFNECRCTDTPPCPVPE
PLGGPSVLIFPPKPKDILRITRTPEVTCVVLDLGREDPEVQISWFV
DGKEVHTAKTQSREQQFAGTYRVVSVLPIEHQDWLTGKEFKCRVNH
IDLPSPIERTISKARGRAHKPSVYVLPPSPKELSSSDTVSITCLIK
DFYPPDIDVEWQSNGQQEPERKHRMTPPQLDEDGSYFLYSKLSVDK
SRWQQGDPFTCAVMHETLQNHYTDLSLSHSPGK**

Figure 19: SEQ ID NO:19 – caTNFrecp80-aglycosyl HCA Fc Fusion Polypeptide

MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGDPKRENGRVPRPPDCPK
CPAPEMLGGPSVFIFPPKPKDTLLIARTPEVTCVVVDLDPEDPEVQ
ISWFVDGKQMQTAKTQPREEQFAGTYRVVSVLPIGHQDWLKGKQFT
CKVNNKALPSPIERTISKARGQAHQPSVYVLPPSREELSKNTVSLT
CLIKDFYPPDIDVEWQSNGQQEPESKYRTTPPQLDEDGSYFLYSKL
SVDKSRWQRGDTFICAVMHEALHNHYTQESLSHSPGK**

Figure 20: SEQ ID NO:20 – caTNFrecp80-aglycosyl HCB Fc Fusion Polypeptide

MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGDAKECECKCNCNNCPCP
GCGLLGGPSVFIFPPKPKDILVTARTPTVTCVVVDLDPENPEVQIS
WFVDSKQVQTANTQPREEQSAGTYRVVSVLPIGHQDWLSGKQFKCK
VNNKALPSPIEEIISKTPGQAHQPNVYVLPPSRDEMSKNTVTLTCL
VKDFFPPEIDVEWQSNGQQEPESKYRMTPPQLDEDGSYFLYSKLSV
DKSRWQRGDTFICAVMHEALHNHYTQISLSHSPGK**

Figure 21: SEQ ID NO:21 – caTNFrecp80-aglycosyl HCC Fc Fusion Polypeptide

MAPAALWALLAAGLQLWGAGRAVPGQATQLPYVPDPELGSSCQQSE
YFDQRTQMCCSMCPPGSHARLFCTKTSNTVCARCENSTYTQLWNWV
PECLSCGSRCGADQVETQACTREQNRICSCKSGWYCTLRRQGGCRL
CAPLRRCRPGFGVAKPGTATSDVVCAPCAPGTFSNTTSSTDTCRPH
RICSSVAVPGNASVDAVCSPAPPTVRTAPRPASTRQPGSTQPRPAE
PTPGPSTPPRTSVLFPAVPSPPAEGLSTGDPKESTCKCISPCPVPE
SLGGPSVFIFPPKPKDILRITRTPEITCVVLDLGREDPEVQISWFV
DGKEVHTAKTQPREQQFASTYRVVSVLPIEHQDWLTGKEFKCRVNH
IGLPSPIERTISKARGQAHQPSVYVLPPSPKELSSSDTVTLTCLIK
DFYPPEIDVEWQSNGQPEPESKYHTTAPQLDEDGSYFLYSKLSVDK
SRWQQGDTFTCAVMHEALQNHYTDLSLSHSPGK**

Figure 22: SEQ ID NO:22 –caTNFrecp80-aglycosyl HCD Fc Fusion Polypeptide

Dimer 25-45 mls
High MW 50-60 mls

```
                                                            1         10        20        30        40        50        60
                                                            |         |         |         |         |         |         |
DN368636 Canine p80 cDNA translation frame 1                ------------------------------MAPAALWAILAAGLQLWGAGRAVPGQATQLPYVPDP
XP_544562.2tumor necrosis factor receptor p80               ------------------MAVLPS---LP---------QATQLPYVPDP
Novel Canine TNFR p80 ECD SEQ ID NO:14                      ------------------------------MAPAALWAILAAGLQLWGAGRAVPGQATQLPYVPDP
Human TNFR p80 ECD P20333|23-257                            ------------------------------MAPVAVWAALAVGLELWAAAHALPAQVAFTPYAPEP DN368636 Canine p80 cDNA translation frame 1                ELGSSCQQSEYFDQRTQMCCSMCPPGSHARLPCTKTSNTVCARCENSTYTQLWNWVPECL
XP_544562.2tumor necrosis factor receptor p80               ELGSSCQQSEYFDQRTQMCCSMCPPGSHARLPCTKTSNTVCARCENSTYTQLWNWVPECL
Novel Canine TNFR p80 ECD SEQ ID NO:14                      ELGSSCQQSEYFDQRTQMCCSMCPPGSHARLPCTKTSNTVCARCENSTYTQLWNWVPECL
Human TNFR p80 ECD P20333|23-257                            --GSTCRLREYYDQTAQMCCSKCSPGQHAKVFCTKTSDTVCDSCEDSTYTQLWNWVPECL DN368636 Canine p80 cDNA translation frame 1                SCGSRCGADQVETQACTREQNRICSCKSGWYCTLRRQGGCRLCAPLRRCRPGFGVARPGT
XP_544562.2tumor necrosis factor receptor p80               SCGSRCGADQVETQACTREQNRICSCKSGWYCTLRRQGGCRLCAPLRRCRPGFGVARPGT
Novel Canine TNFR p80 ECD SEQ ID NO:14                      SCGSRCGADQVETQACTREQNRICSCKSGWYCTLRRQGGCRLCAPLRRCRPGFGVARPGT
Human TNFR p80 ECD P20333|23-257                            SCGSRCSSDQVETQACTREQNRICTCRPGWYCALSKQEGCRLCAPLRKCRPGFGVARPGT DN368636 Canine p80 cDNA translation frame 1                ATSDVVCAPCAPGTFSTRRE---------------------------------
XP_544562.2tumor necrosis factor receptor p80               ATSDVVCAPCAPGTFSNTTSSTDTCRPERICSSVAVPGNASVDAVCSPAPPTVRTAPRDA
Novel Canine TNFR p80 ECD SEQ ID NO:14                      ATSDVVCAPCAPGTFSNTTSSTDTCRPERICSSVAVPGNASVDAVCSPAPPTVRTAPRDA
Human TNFR p80 ECD P20333|23-257                            ETSDVVCKPCAPGTFSNTTSSTDICRPHQICNVVAIPGNASMDAVCTSTSPTRSMAPGAV DN368636 Canine p80 cDNA translation frame 1                ------------------------------------------------------------
XP_544562.2tumor necrosis factor receptor p80               STRQPGSTQPRPAEPTPGPSTPPRTSVLFPAVPSPPAEGLSTGDISLPIGLIVGVTTLGL
Novel Canine TNFR p80 ECD SEQ ID NO:14                      STRQPGSTQPRPAEPTPGPSTPPRTSVLFPAVPSPPAEGLSTGD----------------
Human TNFR p80 ECD P20333|23-257                            HLPQPVSTRSQHTQPTEEPSTAPSTSPLLPMGPSPPAEG-STGD----------------

DN368636 Canine p80 cDNA translation frame 1                ------------------
XP_544562.2tumor necrosis factor receptor p80               LLIGLVNCVIV-------
Novel Canine TNFR p80 ECD SEQ ID NO:14                      ------------------
Human TNFR p80 ECD P20333|23-257                            ------------------
```

Figure 30

SEQUENCE LISTING

<160> NUMBER OF SEQ ID NOS: 31

<210> SEQ ID NO 1
<211> LENGTH: 212
<212> TYPE: PRT
<213> ORGANISM: Canis familiaris

<400> SEQUENCE: 1

Ala Met Gly Leu Pro Thr Val Pro Gly Leu Leu Pro Leu Val Leu
1               5                   10                  15

Leu Ala Leu Leu Glu Ile Tyr Pro Ile Ser Val Thr Ala Leu Val
                20                  25                  30

Pro His Pro Arg Asn Arg Val Lys Arg Ala Ile Leu Cys Pro Gln Gly
            35                  40                  45

Lys Tyr Ile His Pro Gln Asp Asp Ser Ile Cys Cys Thr Lys Cys His
50                  55                      60

Lys Gly Thr Tyr Leu Tyr Asn Asp Cys Pro Gly Pro Gly Leu Asp Thr
65                  70                  75                      80

Asp Cys Arg Glu Cys Glu Asn Gly Thr Phe Thr Ala Ser Glu Asn His
                85                  90                      95

Leu Arg Gln Cys Leu Ser Cys Ser Lys Cys Arg Lys Glu Met Asn Gln
                100                 105                 110

Val Glu Ile Ser Pro Cys Thr Val Tyr Arg Asp Thr Val Cys Gly Cys
            115                 120                 125

Arg Lys Asn Gln Tyr Arg Phe Tyr Trp Ser Glu Thr Leu Phe Gln Cys
    130                 135                 140

Asn Asn Cys Ser Leu Cys Leu Asn Gly Thr Val Gln Ile Ser Cys Gln
145                 150                 155                 160

Glu Lys Gln Asn Thr Ile Cys Thr Cys His Ala Gly Phe Phe Leu Arg
                165                 170                 175

Glu His Glu Cys Val Ser Cys Val Asn Cys Lys Lys Asn Thr Glu Cys
                180                 185                 190

Gly Lys Leu Cys Leu Pro Pro Val Glu Thr Val Lys Val Pro Gln Asp
            195                 200                 205

Pro Gly Ser Thr
    210

<210> SEQ ID NO 2
<211> LENGTH: 233
<212> TYPE: PRT
<213> ORGANISM: Canis familiaris

<400> SEQUENCE: 2

Phe Asn Glu Cys Arg Cys Thr Asp Thr Pro Pro Cys Pro Val Pro Glu

```
              1               5                  10                 15
         Pro Leu Gly Gly Pro Ser Val Leu Ile Phe Pro Pro Lys Pro Lys Asp
                         20                 25                 30

Ile Leu Arg Ile Thr Arg Thr Pro Glu Val Thr Cys Val Val Leu Asp
                         35                 40                 45

Leu Gly Arg Glu Asp Pro Glu Val Gln Ile Ser Trp Phe Val Asp Gly
         50                  55                 60

Lys Glu Val His Thr Ala Lys Thr Gln Ser Arg Glu Gln Gln Phe Asn
         65                  70                 75                 80

Gly Thr Tyr Arg Val Val Ser Val Leu Pro Ile Glu His Gln Asp Trp
                         85                 90                 95

Leu Thr Gly Lys Glu Phe Lys Cys Arg Val Asn His Ile Asp Leu Pro
                         100                105                110

Ser Pro Ile Glu Arg Thr Ile Ser Lys Ala Arg Gly Arg Ala His Lys
                         115                120                125

Pro Ser Val Tyr Val Leu Pro Pro Ser Pro Lys Glu Leu Ser Ser Ser
         130                 135                140

Asp Thr Val Ser Ile Thr Cys Leu Ile Lys Asp Phe Tyr Pro Pro Asp
         145                 150                155                160

Ile Asp Val Glu Trp Gln Ser Asn Gly Gln Gln Glu Pro Glu Arg Lys
                         165                170                175

His Arg Met Thr Pro Pro Gln Leu Asp Glu Asp Gly Ser Tyr Phe Leu
                         180                185                190

Tyr Ser Lys Leu Ser Val Asp Lys Ser Arg Trp Gln Gln Gly Asp Pro
                         195                200                205

Phe Thr Cys Ala Val Met His Glu Thr Leu Gln Asn His Tyr Thr Asp
                         210                215                220

Leu Ser Leu Ser His Ser Pro Gly Lys
         225                 230

<210> SEQ ID NO 3
<211> LENGTH: 237
<212> TYPE: PRT
<213> ORGANISM: Canis familiaris

<400> SEQUENCE: 3

Pro Lys Arg Glu Asn Gly Arg Val Pro Arg Pro Asp Cys Pro Lys
         1               5                  10                 15

Cys Pro Ala Pro Glu Met Leu Gly Gly Pro Ser Val Phe Ile Phe Pro
                         20                 25                 30

Pro Lys Pro Lys Asp Thr Leu Leu Ile Ala Arg Thr Pro Glu Val Thr
                         35                 40                 45

Cys Val Val Val Asp Leu Asp Pro Glu Asp Pro Glu Val Gln Ile Ser
         50                  55                 60

Trp Phe Val Asp Gly Lys Gln Met Gln Thr Ala Lys Thr Gln Pro Arg
         65                  70                 75                 80

Glu Glu Gln Phe Asn Gly Thr Tyr Arg Val Val Ser Val Leu Pro Ile
                         85                 90                 95

Gly His Gln Asp Trp Leu Lys Gly Lys Gln Phe Thr Cys Lys Val Asn
                         100                105                110

Asn Lys Ala Leu Pro Ser Pro Ile Glu Arg Thr Ile Ser Lys Ala Arg
                         115                120                125

Gly Gln Ala His Gln Pro Ser Val Tyr Val Leu Pro Pro Ser Arg Glu
         130                 135                140
```

```
Glu Leu Ser Lys Asn Thr Val Ser Leu Thr Cys Leu Ile Lys Asp Phe
145                 150                 155                 160

Tyr Pro Pro Asp Ile Asp Val Glu Trp Gln Ser Asn Gly Gln Gln Glu
                165                 170                 175

Pro Glu Ser Lys Tyr Arg Thr Thr Pro Gln Leu Asp Glu Asp Gly
            180                 185                 190

Ser Tyr Phe Leu Tyr Ser Lys Leu Ser Val Asp Lys Ser Arg Trp Gln
        195                 200                 205

Arg Gly Asp Thr Phe Ile Cys Ala Val Met His Glu Ala Leu His Asn
        210                 215                 220

His Tyr Thr Gln Glu Ser Leu Ser His Ser Pro Gly Lys
225                 230                 235
```

```
<210> SEQ ID NO 4
<211> LENGTH: 235
<212> TYPE: PRT
<213> ORGANISM: Canis familiaris

<400> SEQUENCE: 4

Ala Lys Glu Cys Glu Cys Lys Cys Asn Cys Asn Asn Cys Pro Cys Pro
1               5                   10                  15

Gly Cys Gly Leu Leu Gly Gly Pro Ser Val Phe Ile Phe Pro Pro Lys
            20                  25                  30

Pro Lys Asp Ile Leu Val Thr Ala Arg Thr Pro Thr Val Thr Cys Val
            35                  40                  45

Val Val Asp Leu Asp Pro Glu Asn Pro Glu Val Gln Ile Ser Trp Phe
50                  55                  60

Val Asp Ser Lys Gln Val Gln Thr Ala Asn Thr Gln Pro Arg Glu Glu
65                  70                  75                  80

Gln Ser Asn Gly Thr Tyr Arg Val Val Ser Val Leu Pro Ile Gly His
                85                  90                  95

Gln Asp Trp Leu Ser Gly Lys Gln Phe Lys Cys Lys Val Asn Asn Lys
            100                 105                 110

Ala Leu Pro Ser Pro Ile Glu Glu Ile Ile Ser Lys Thr Pro Gly Gln
        115                 120                 125

Ala His Gln Pro Asn Val Tyr Val Leu Pro Pro Ser Arg Asp Glu Met
    130                 135                 140

Ser Lys Asn Thr Val Thr Leu Thr Cys Leu Val Lys Asp Phe Phe Pro
145                 150                 155                 160

Pro Glu Ile Asp Val Glu Trp Gln Ser Asn Gly Gln Gln Glu Pro Glu
                165                 170                 175

Ser Lys Tyr Arg Met Thr Pro Pro Gln Leu Asp Glu Asp Gly Ser Tyr
            180                 185                 190

Phe Leu Tyr Ser Lys Leu Ser Val Asp Lys Ser Arg Trp Gln Arg Gly
        195                 200                 205

Asp Thr Phe Ile Cys Ala Val Met His Glu Ala Leu His Asn His Tyr
    210                 215                 220

Thr Gln Ile Ser Leu Ser His Ser Pro Gly Lys
225                 230                 235
```

```
<210> SEQ ID NO 5
<211> LENGTH: 233
<212> TYPE: PRT
<213> ORGANISM: Canis familiaris

<400> SEQUENCE: 5
```

```
Pro Lys Glu Ser Thr Cys Lys Cys Ile Ser Pro Cys Pro Val Pro Glu
1               5                   10                  15

Ser Leu Gly Gly Pro Ser Val Phe Ile Phe Pro Lys Pro Lys Asp
            20                  25                  30

Ile Leu Arg Ile Thr Arg Thr Pro Glu Ile Thr Cys Val Val Leu Asp
            35                  40                  45

Leu Gly Arg Glu Asp Pro Glu Val Gln Ile Ser Trp Phe Val Asp Gly
    50                  55                  60

Lys Glu Val His Thr Ala Lys Thr Gln Pro Arg Glu Gln Gln Phe Asn
65                  70                  75                  80

Ser Thr Tyr Arg Val Val Ser Val Leu Pro Ile Glu His Gln Asp Trp
                85                  90                  95

Leu Thr Gly Lys Glu Phe Lys Cys Arg Val Asn His Ile Gly Leu Pro
            100                 105                 110

Ser Pro Ile Glu Arg Thr Ile Ser Lys Ala Arg Gly Gln Ala His Gln
            115                 120                 125

Pro Ser Val Tyr Val Leu Pro Pro Ser Pro Lys Glu Leu Ser Ser Ser
    130                 135                 140

Asp Thr Val Thr Leu Thr Cys Leu Ile Lys Asp Phe Tyr Pro Pro Glu
145                 150                 155                 160

Ile Asp Val Glu Trp Gln Ser Asn Gly Gln Pro Glu Pro Glu Ser Lys
                165                 170                 175

Tyr His Thr Thr Ala Pro Gln Leu Asp Glu Asp Gly Ser Tyr Phe Leu
            180                 185                 190

Tyr Ser Lys Leu Ser Val Asp Lys Ser Arg Trp Gln Gln Gly Asp Thr
            195                 200                 205

Phe Thr Cys Ala Val Met His Glu Ala Leu Gln Asn His Tyr Thr Asp
    210                 215                 220

Leu Ser Leu Ser His Ser Pro Gly Lys
225                 230

<210> SEQ ID NO 6
<211> LENGTH: 444
<212> TYPE: PRT
<213> ORGANISM: Artificial Sequence
<220> FEATURE:
<223> OTHER INFORMATION: caTNFRp60:HCA Fc Fusion Polypeptide

<400> SEQUENCE: 6

Met Gly Leu Pro Thr Val Pro Gly Leu Leu Leu Pro Leu Val Leu Leu
1               5                   10                  15

Ala Leu Leu Leu Glu Ile Tyr Pro Ile Ser Val Thr Ala Leu Val Pro
            20                  25                  30

His Pro Arg Asn Arg Val Lys Arg Ala Ile Leu Cys Pro Gln Gly Lys
            35                  40                  45

Tyr Ile His Pro Gln Asp Asp Ser Ile Cys Cys Thr Lys Cys His Lys
    50                  55                  60

Gly Thr Tyr Leu Tyr Asn Asp Cys Pro Gly Pro Gly Leu Asp Thr Asp
65                  70                  75                  80

Cys Arg Glu Cys Glu Asn Gly Thr Phe Thr Ala Ser Glu Asn His Leu
                85                  90                  95

Arg Gln Cys Leu Ser Cys Ser Lys Cys Arg Lys Glu Met Asn Gln Val
            100                 105                 110

Glu Ile Ser Pro Cys Thr Val Tyr Arg Asp Thr Val Cys Gly Cys Arg
            115                 120                 125
```

Lys Asn Gln Tyr Arg Phe Tyr Trp Ser Glu Thr Leu Phe Gln Cys Asn
            130                 135                 140

Asn Cys Ser Leu Cys Leu Asn Gly Thr Val Gln Ile Ser Cys Gln Glu
145                 150                 155                 160

Lys Gln Asn Thr Ile Cys Thr Cys His Ala Gly Phe Phe Leu Arg Glu
            165                 170                 175

His Glu Cys Val Ser Cys Val Asn Cys Lys Lys Asn Thr Glu Cys Gly
            180                 185                 190

Lys Leu Cys Leu Pro Pro Val Glu Thr Val Lys Val Pro Gln Asp Pro
            195                 200                 205

Gly Ser Thr Phe Asn Glu Cys Arg Cys Thr Asp Thr Pro Pro Cys Pro
210                 215                 220

Val Pro Glu Pro Leu Gly Gly Pro Ser Val Leu Ile Phe Pro Pro Lys
225                 230                 235                 240

Pro Lys Asp Ile Leu Arg Ile Thr Arg Thr Pro Glu Val Thr Cys Val
            245                 250                 255

Val Leu Asp Leu Gly Arg Glu Asp Pro Glu Val Gln Ile Ser Trp Phe
            260                 265                 270

Val Asp Gly Lys Glu Val His Thr Ala Lys Thr Gln Ser Arg Glu Gln
            275                 280                 285

Gln Phe Asn Gly Thr Tyr Arg Val Val Ser Val Leu Pro Ile Glu His
            290                 295                 300

Gln Asp Trp Leu Thr Gly Lys Glu Phe Lys Cys Arg Val Asn His Ile
305                 310                 315                 320

Asp Leu Pro Ser Pro Ile Glu Arg Thr Ile Ser Lys Ala Arg Gly Arg
            325                 330                 335

Ala His Lys Pro Ser Val Tyr Val Leu Pro Pro Ser Pro Lys Glu Leu
            340                 345                 350

Ser Ser Ser Asp Thr Val Ser Ile Thr Cys Leu Ile Lys Asp Phe Tyr
            355                 360                 365

Pro Pro Asp Ile Asp Val Glu Trp Gln Ser Asn Gly Gln Gln Glu Pro
370                 375                 380

Glu Arg Lys His Arg Met Thr Pro Pro Gln Leu Asp Glu Asp Gly Ser
385                 390                 395                 400

Tyr Phe Leu Tyr Ser Lys Leu Ser Val Asp Lys Ser Arg Trp Gln Gln
            405                 410                 415

Gly Asp Pro Phe Thr Cys Ala Val Met His Glu Thr Leu Gln Asn His
            420                 425                 430

Tyr Thr Asp Leu Ser Leu Ser His Ser Pro Gly Lys
            435                 440

<210> SEQ ID NO 7
<211> LENGTH: 448
<212> TYPE: PRT
<213> ORGANISM: Artificial Sequence
<220> FEATURE:
<223> OTHER INFORMATION: caTNFRp60:HCB Fc Fusion Polypeptide

<400> SEQUENCE: 7

Met Gly Leu Pro Thr Val Pro Gly Leu Leu Leu Pro Leu Val Leu Leu
1               5                   10                  15

Ala Leu Leu Leu Glu Ile Tyr Pro Ile Ser Val Thr Ala Leu Val Pro
            20                  25                  30

His Pro Arg Asn Arg Val Lys Arg Ala Ile Leu Cys Pro Gln Gly Lys
            35                  40                  45

```
Tyr Ile His Pro Gln Asp Asp Ser Ile Cys Cys Thr Lys Cys His Lys
 50                  55                  60
Gly Thr Tyr Leu Tyr Asn Asp Cys Pro Gly Pro Gly Leu Asp Thr Asp
 65                  70                  75                  80
Cys Arg Glu Cys Glu Asn Gly Thr Phe Thr Ala Ser Glu Asn His Leu
                 85                  90                  95
Arg Gln Cys Leu Ser Cys Ser Lys Cys Arg Lys Glu Met Asn Gln Val
            100                 105                 110
Glu Ile Ser Pro Cys Thr Val Tyr Arg Asp Thr Val Cys Gly Cys Arg
        115                 120                 125
Lys Asn Gln Tyr Arg Phe Tyr Trp Ser Glu Thr Leu Phe Gln Cys Asn
130                 135                 140
Asn Cys Ser Leu Cys Leu Asn Gly Thr Val Gln Ile Ser Cys Gln Glu
145                 150                 155                 160
Lys Gln Asn Thr Ile Cys Thr Cys His Ala Gly Phe Phe Leu Arg Glu
                165                 170                 175
His Glu Cys Val Ser Cys Val Asn Cys Lys Lys Asn Thr Glu Cys Gly
            180                 185                 190
Lys Leu Cys Leu Pro Pro Val Glu Thr Val Lys Val Pro Gln Asp Pro
        195                 200                 205
Gly Ser Thr Pro Lys Arg Glu Asn Gly Arg Val Pro Arg Pro Pro Asp
210                 215                 220
Cys Pro Lys Cys Pro Ala Pro Glu Met Leu Gly Pro Ser Val Phe
225                 230                 235                 240
Ile Phe Pro Pro Lys Pro Lys Asp Thr Leu Leu Ile Ala Arg Thr Pro
                245                 250                 255
Glu Val Thr Cys Val Val Val Asp Leu Asp Pro Glu Asp Pro Glu Val
            260                 265                 270
Gln Ile Ser Trp Phe Val Asp Gly Lys Gln Met Gln Thr Ala Lys Thr
        275                 280                 285
Gln Pro Arg Glu Glu Gln Phe Asn Gly Thr Tyr Arg Val Val Ser Val
290                 295                 300
Leu Pro Ile Gly His Gln Asp Trp Leu Lys Gly Lys Gln Phe Thr Cys
305                 310                 315                 320
Lys Val Asn Asn Lys Ala Leu Pro Ser Pro Ile Glu Arg Thr Ile Ser
                325                 330                 335
Lys Ala Arg Gly Gln Ala His Gln Pro Ser Val Tyr Val Leu Pro Pro
            340                 345                 350
Ser Arg Glu Glu Leu Ser Lys Asn Thr Val Ser Leu Thr Cys Leu Ile
        355                 360                 365
Lys Asp Phe Tyr Pro Pro Asp Ile Asp Val Glu Trp Gln Ser Asn Gly
370                 375                 380
Gln Gln Glu Pro Glu Ser Lys Tyr Arg Thr Thr Pro Pro Gln Leu Asp
385                 390                 395                 400
Glu Asp Gly Ser Tyr Phe Leu Tyr Ser Lys Leu Ser Val Asp Lys Ser
                405                 410                 415
Arg Trp Gln Arg Gly Asp Thr Phe Ile Cys Ala Val Met His Glu Ala
            420                 425                 430
Leu His Asn His Tyr Thr Gln Glu Ser Leu Ser His Ser Pro Gly Lys
        435                 440                 445

<210> SEQ ID NO 8
<211> LENGTH: 446
<212> TYPE: PRT
```

<213> ORGANISM: Artificial Sequence
<220> FEATURE:
<223> OTHER INFORMATION: caTNFRp60:HCC Fc Fusion Polypeptide

<400> SEQUENCE: 8

```
Met Gly Leu Pro Thr Val Pro Gly Leu Leu Pro Leu Val Leu Leu
1               5                   10                  15

Ala Leu Leu Leu Glu Ile Tyr Pro Ile Ser Val Thr Ala Leu Val Pro
                20                  25                  30

His Pro Arg Asn Arg Val Lys Arg Ala Ile Leu Cys Pro Gln Gly Lys
            35                  40                  45

Tyr Ile His Pro Gln Asp Asp Ser Ile Cys Cys Thr Lys Cys His Lys
        50                  55                  60

Gly Thr Tyr Leu Tyr Asn Asp Cys Pro Gly Pro Gly Leu Asp Thr Asp
65                  70                  75                  80

Cys Arg Glu Cys Glu Asn Gly Thr Phe Thr Ala Ser Glu Asn His Leu
                85                  90                  95

Arg Gln Cys Leu Ser Cys Ser Lys Cys Arg Lys Glu Met Asn Gln Val
            100                 105                 110

Glu Ile Ser Pro Cys Thr Val Tyr Arg Asp Thr Val Cys Gly Cys Arg
        115                 120                 125

Lys Asn Gln Tyr Arg Phe Tyr Trp Ser Glu Thr Leu Phe Gln Cys Asn
130                 135                 140

Asn Cys Ser Leu Cys Leu Asn Gly Thr Val Gln Ile Ser Cys Gln Glu
145                 150                 155                 160

Lys Gln Asn Thr Ile Cys Thr Cys His Ala Gly Phe Phe Leu Arg Glu
                165                 170                 175

His Glu Cys Val Ser Cys Val Asn Cys Lys Lys Asn Thr Glu Cys Gly
            180                 185                 190

Lys Leu Cys Leu Pro Pro Val Glu Thr Val Lys Val Pro Gln Asp Pro
        195                 200                 205

Gly Ser Thr Ala Lys Glu Cys Glu Cys Lys Cys Asn Cys Asn Asn Cys
    210                 215                 220

Pro Cys Pro Gly Cys Gly Leu Leu Gly Gly Pro Ser Val Phe Ile Phe
225                 230                 235                 240

Pro Pro Lys Pro Lys Asp Ile Leu Val Thr Ala Arg Thr Pro Thr Val
                245                 250                 255

Thr Cys Val Val Val Asp Leu Asp Pro Glu Asn Pro Glu Val Gln Ile
            260                 265                 270

Ser Trp Phe Val Asp Ser Lys Gln Val Gln Thr Ala Asn Thr Gln Pro
        275                 280                 285

Arg Glu Glu Gln Ser Asn Gly Thr Tyr Arg Val Val Ser Val Leu Pro
    290                 295                 300

Ile Gly His Gln Asp Trp Leu Ser Gly Lys Gln Phe Lys Cys Lys Val
305                 310                 315                 320

Asn Asn Lys Ala Leu Pro Ser Pro Ile Glu Glu Ile Ile Ser Lys Thr
                325                 330                 335

Pro Gly Gln Ala His Gln Pro Asn Val Tyr Val Leu Pro Pro Ser Arg
            340                 345                 350

Asp Glu Met Ser Lys Asn Thr Val Thr Leu Thr Cys Leu Val Lys Asp
        355                 360                 365

Phe Phe Pro Pro Glu Ile Asp Val Glu Trp Gln Ser Asn Gly Gln Gln
    370                 375                 380

Glu Pro Glu Ser Lys Tyr Arg Met Thr Pro Pro Gln Leu Asp Glu Asp
```

-continued

```
                385                 390                 395                 400
Gly Ser Tyr Phe Leu Tyr Ser Lys Leu Ser Val Asp Lys Ser Arg Trp
                    405                 410                 415
Gln Arg Gly Asp Thr Phe Ile Cys Ala Val Met His Glu Ala Leu His
                420                 425                 430
Asn His Tyr Thr Gln Ile Ser Leu Ser His Ser Pro Gly Lys
                435                 440                 445

<210> SEQ ID NO 9
<211> LENGTH: 444
<212> TYPE: PRT
<213> ORGANISM: Artificial Sequence
<220> FEATURE:
<223> OTHER INFORMATION: caTNFRp60:HCD Fc Fusion Polypeptide

<400> SEQUENCE: 9

Met Gly Leu Pro Thr Val Pro Gly Leu Leu Leu Pro Leu Val Leu Leu
1               5                   10                  15
Ala Leu Leu Glu Ile Tyr Pro Ile Ser Val Thr Ala Leu Val Pro
            20                  25                  30
His Pro Arg Asn Arg Val Lys Arg Ala Ile Leu Cys Pro Gln Gly Lys
        35                  40                  45
Tyr Ile His Pro Gln Asp Ser Ile Cys Cys Thr Lys Cys His Lys
    50                  55                  60
Gly Thr Tyr Leu Tyr Asn Asp Cys Pro Gly Pro Gly Leu Asp Thr Asp
65                  70                  75                  80
Cys Arg Glu Cys Glu Asn Gly Thr Phe Thr Ala Ser Glu Asn His Leu
                85                  90                  95
Arg Gln Cys Leu Ser Cys Ser Lys Cys Arg Lys Glu Met Asn Gln Val
            100                 105                 110
Glu Ile Ser Pro Cys Thr Val Tyr Arg Asp Thr Val Cys Gly Cys Arg
        115                 120                 125
Lys Asn Gln Tyr Arg Phe Tyr Trp Ser Glu Thr Leu Phe Gln Cys Asn
    130                 135                 140
Asn Cys Ser Leu Cys Leu Asn Gly Thr Val Gln Ile Ser Cys Gln Glu
145                 150                 155                 160
Lys Gln Asn Thr Ile Cys Thr Cys His Ala Gly Phe Phe Leu Arg Glu
                165                 170                 175
His Glu Cys Val Ser Cys Val Asn Cys Lys Lys Asn Thr Glu Cys Gly
            180                 185                 190
Lys Leu Cys Leu Pro Pro Val Glu Thr Val Lys Val Pro Gln Asp Pro
        195                 200                 205
Gly Ser Thr Pro Lys Glu Ser Thr Cys Lys Cys Ile Ser Pro Cys Pro
    210                 215                 220
Val Pro Glu Ser Leu Gly Gly Pro Ser Val Phe Ile Phe Pro Pro Lys
225                 230                 235                 240
Pro Lys Asp Ile Leu Arg Ile Thr Arg Thr Pro Glu Ile Thr Cys Val
                245                 250                 255
Val Leu Asp Leu Gly Arg Glu Asp Pro Glu Val Gln Ile Ser Trp Phe
            260                 265                 270
Val Asp Gly Lys Glu Val His Thr Ala Lys Thr Gln Pro Arg Glu Gln
        275                 280                 285
Gln Phe Asn Ser Thr Tyr Arg Val Val Ser Val Leu Pro Ile Glu His
    290                 295                 300
Gln Asp Trp Leu Thr Gly Lys Glu Phe Lys Cys Arg Val Asn His Ile
```

```
                305                 310                 315                 320
Gly Leu Pro Ser Pro Ile Glu Arg Thr Ile Ser Lys Ala Arg Gly Gln
                325                 330                 335

Ala His Gln Pro Ser Val Tyr Val Leu Pro Ser Pro Lys Glu Leu
                340                 345                 350

Ser Ser Ser Asp Thr Val Thr Leu Thr Cys Leu Ile Lys Asp Phe Tyr
                355                 360                 365

Pro Pro Glu Ile Asp Val Glu Trp Gln Ser Asn Gly Gln Pro Glu Pro
        370                 375                 380

Glu Ser Lys Tyr His Thr Thr Ala Pro Gln Leu Asp Glu Asp Gly Ser
385                 390                 395                 400

Tyr Phe Leu Tyr Ser Lys Leu Ser Val Asp Lys Ser Arg Trp Gln Gln
                405                 410                 415

Gly Asp Thr Phe Thr Cys Ala Val Met His Glu Ala Leu Gln Asn His
                420                 425                 430

Tyr Thr Asp Leu Ser Leu Ser His Ser Pro Gly Lys
                435                 440
```

<210> SEQ ID NO 10
<211> LENGTH: 444
<212> TYPE: PRT
<213> ORGANISM: Artificial Sequence
<220> FEATURE:
<223> OTHER INFORMATION: caTNFRp60:HCA Aglycosyl Fc Fusion Polypeptide

<400> SEQUENCE: 10

```
Met Gly Leu Pro Thr Val Pro Gly Leu Leu Pro Leu Val Leu Leu
1               5                   10                  15

Ala Leu Leu Leu Glu Ile Tyr Pro Ile Ser Val Thr Ala Leu Val Pro
                20                  25                  30

His Pro Arg Asn Arg Val Lys Arg Ala Ile Leu Cys Pro Gln Gly Lys
                35                  40                  45

Tyr Ile His Pro Gln Asp Asp Ser Ile Cys Cys Thr Lys Cys His Lys
            50                  55                  60

Gly Thr Tyr Leu Tyr Asn Asp Cys Pro Gly Pro Gly Leu Asp Thr Asp
65                  70                  75                  80

Cys Arg Glu Cys Glu Asn Gly Thr Phe Thr Ala Ser Glu Asn His Leu
                85                  90                  95

Arg Gln Cys Leu Ser Cys Ser Lys Cys Arg Lys Glu Met Asn Gln Val
                100                 105                 110

Glu Ile Ser Pro Cys Thr Val Tyr Arg Asp Thr Val Cys Gly Cys Arg
            115                 120                 125

Lys Asn Gln Tyr Arg Phe Tyr Trp Ser Glu Thr Leu Phe Gln Cys Asn
130                 135                 140

Asn Cys Ser Leu Cys Leu Asn Gly Thr Val Gln Ile Ser Cys Gln Glu
145                 150                 155                 160

Lys Gln Asn Thr Ile Cys Thr Cys His Ala Gly Phe Phe Leu Arg Glu
                165                 170                 175

His Glu Cys Val Ser Cys Val Asn Cys Lys Lys Asn Thr Glu Cys Gly
                180                 185                 190

Lys Leu Cys Leu Pro Pro Val Glu Thr Val Lys Val Pro Gln Asp Pro
            195                 200                 205

Gly Ser Thr Phe Asn Glu Cys Arg Cys Thr Asp Thr Pro Pro Cys Pro
        210                 215                 220

Val Pro Glu Pro Leu Gly Gly Pro Ser Val Leu Ile Phe Pro Pro Lys
```

```
                225                 230                 235                 240
Pro Lys Asp Ile Leu Arg Ile Thr Arg Thr Pro Glu Val Thr Cys Val
            245                 250                 255

Val Leu Asp Leu Gly Arg Glu Asp Pro Glu Val Gln Ile Ser Trp Phe
            260                 265                 270

Val Asp Gly Lys Glu Val His Thr Ala Lys Thr Gln Ser Arg Glu Gln
            275                 280                 285

Gln Phe Ala Gly Thr Tyr Arg Val Val Ser Val Leu Pro Ile Glu His
        290                 295                 300

Gln Asp Trp Leu Thr Gly Lys Glu Phe Lys Cys Arg Val Asn His Ile
305                 310                 315                 320

Asp Leu Pro Ser Pro Ile Glu Arg Thr Ile Ser Lys Ala Arg Gly Arg
                325                 330                 335

Ala His Lys Pro Ser Val Tyr Val Leu Pro Pro Ser Pro Lys Glu Leu
            340                 345                 350

Ser Ser Ser Asp Thr Val Ser Ile Thr Cys Leu Ile Lys Asp Phe Tyr
        355                 360                 365

Pro Pro Asp Ile Asp Val Glu Trp Gln Ser Asn Gly Gln Gln Glu Pro
    370                 375                 380

Glu Arg Lys His Arg Met Thr Pro Pro Gln Leu Asp Glu Asp Gly Ser
385                 390                 395                 400

Tyr Phe Leu Tyr Ser Lys Leu Ser Val Asp Lys Ser Arg Trp Gln Gln
                405                 410                 415

Gly Asp Pro Phe Thr Cys Ala Val Met His Glu Thr Leu Gln Asn His
            420                 425                 430

Tyr Thr Asp Leu Ser Leu Ser His Ser Pro Gly Lys
        435                 440

<210> SEQ ID NO 11
<211> LENGTH: 448
<212> TYPE: PRT
<213> ORGANISM: Artificial Sequence
<220> FEATURE:
<223> OTHER INFORMATION: caTNFRp60:HCB Aglycosyl Fc Fusion Polypeptide

<400> SEQUENCE: 11

Met Gly Leu Pro Thr Val Pro Gly Leu Leu Leu Pro Leu Val Leu Leu
1               5                   10                  15

Ala Leu Leu Leu Glu Ile Tyr Pro Ile Ser Val Thr Ala Leu Val Pro
            20                  25                  30

His Pro Arg Asn Arg Val Lys Arg Ala Ile Leu Cys Pro Gln Gly Lys
        35                  40                  45

Tyr Ile His Pro Gln Asp Asp Ser Ile Cys Cys Thr Lys Cys His Lys
    50                  55                  60

Gly Thr Tyr Leu Tyr Asn Asp Cys Pro Gly Pro Gly Leu Asp Thr Asp
65                  70                  75                  80

Cys Arg Glu Cys Glu Asn Gly Thr Phe Thr Ala Ser Glu Asn His Leu
                85                  90                  95

Arg Gln Cys Leu Ser Cys Ser Lys Cys Arg Lys Glu Met Asn Gln Val
            100                 105                 110

Glu Ile Ser Pro Cys Thr Val Tyr Arg Asp Thr Val Cys Gly Cys Arg
        115                 120                 125

Lys Asn Gln Tyr Arg Phe Tyr Trp Ser Glu Thr Leu Phe Gln Cys Asn
    130                 135                 140

Asn Cys Ser Leu Cys Leu Asn Gly Thr Val Gln Ile Ser Cys Gln Glu
```

```
            145                 150                 155                 160
Lys Gln Asn Thr Ile Cys Thr Cys His Ala Gly Phe Phe Leu Arg Glu
                165                 170                 175

His Glu Cys Val Ser Cys Val Asn Cys Lys Lys Asn Thr Glu Cys Gly
            180                 185                 190

Lys Leu Cys Leu Pro Pro Val Glu Thr Val Lys Val Pro Gln Asp Pro
        195                 200                 205

Gly Ser Thr Pro Lys Arg Glu Asn Gly Arg Val Pro Arg Pro Pro Asp
    210                 215                 220

Cys Pro Lys Cys Pro Ala Pro Glu Met Leu Gly Gly Pro Ser Val Phe
225                 230                 235                 240

Ile Phe Pro Pro Lys Pro Lys Asp Thr Leu Leu Ile Ala Arg Thr Pro
                245                 250                 255

Glu Val Thr Cys Val Val Val Asp Leu Asp Pro Glu Asp Pro Glu Val
            260                 265                 270

Gln Ile Ser Trp Phe Val Asp Gly Lys Gln Met Gln Thr Ala Lys Thr
        275                 280                 285

Gln Pro Arg Glu Glu Gln Phe Ala Gly Thr Tyr Arg Val Val Ser Val
    290                 295                 300

Leu Pro Ile Gly His Gln Asp Trp Leu Lys Gly Lys Gln Phe Thr Cys
305                 310                 315                 320

Lys Val Asn Asn Lys Ala Leu Pro Ser Pro Ile Glu Arg Thr Ile Ser
                325                 330                 335

Lys Ala Arg Gly Gln Ala His Gln Pro Ser Val Tyr Val Leu Pro Pro
            340                 345                 350

Ser Arg Glu Glu Leu Ser Lys Asn Thr Val Ser Leu Thr Cys Leu Ile
        355                 360                 365

Lys Asp Phe Tyr Pro Pro Asp Ile Asp Val Glu Trp Gln Ser Asn Gly
    370                 375                 380

Gln Gln Glu Pro Glu Ser Lys Tyr Arg Thr Thr Pro Pro Gln Leu Asp
385                 390                 395                 400

Glu Asp Gly Ser Tyr Phe Leu Tyr Ser Lys Leu Ser Val Asp Lys Ser
                405                 410                 415

Arg Trp Gln Arg Gly Asp Thr Phe Ile Cys Ala Val Met His Glu Ala
            420                 425                 430

Leu His Asn His Tyr Thr Gln Glu Ser Leu Ser His Ser Pro Gly Lys
        435                 440                 445

<210> SEQ ID NO 12
<211> LENGTH: 446
<212> TYPE: PRT
<213> ORGANISM: Artificial Sequence
<220> FEATURE:
<223> OTHER INFORMATION: caTNFRp60:HCC Aglycosyl Fc Fusion Polypeptide

<400> SEQUENCE: 12

Met Gly Leu Pro Thr Val Pro Gly Leu Leu Leu Pro Leu Val Leu Leu
1               5                   10                  15

Ala Leu Leu Leu Glu Ile Tyr Pro Ile Ser Val Thr Ala Leu Val Pro
            20                  25                  30

His Pro Arg Asn Arg Val Lys Arg Ala Ile Leu Cys Pro Gln Gly Lys
        35                  40                  45

Tyr Ile His Pro Gln Asp Asp Ser Ile Cys Cys Thr Lys Cys His Lys
    50                  55                  60

Gly Thr Tyr Leu Tyr Asn Asp Cys Pro Gly Pro Gly Leu Asp Thr Asp
```

```
              65                  70                  75                  80
        Cys Arg Glu Cys Glu Asn Gly Thr Phe Thr Ala Ser Glu Asn His Leu
                        85                  90                  95

Arg Gln Cys Leu Ser Cys Ser Lys Cys Arg Lys Glu Met Asn Gln Val
                        100                 105                 110

Glu Ile Ser Pro Cys Thr Val Tyr Arg Asp Thr Val Cys Gly Cys Arg
                        115                 120                 125

Lys Asn Gln Tyr Arg Phe Tyr Trp Ser Glu Thr Leu Phe Gln Cys Asn
                        130                 135                 140

Asn Cys Ser Leu Cys Leu Asn Gly Thr Val Gln Ile Ser Cys Gln Glu
        145                 150                 155                 160

Lys Gln Asn Thr Ile Cys Thr Cys His Ala Gly Phe Phe Leu Arg Glu
                        165                 170                 175

His Glu Cys Val Ser Cys Val Asn Cys Lys Lys Asn Thr Glu Cys Gly
                        180                 185                 190

Lys Leu Cys Leu Pro Val Glu Thr Val Lys Val Pro Gln Asp Pro
                        195                 200                 205

Gly Ser Thr Ala Lys Glu Cys Glu Cys Lys Cys Asn Cys Asn Asn Cys
                210                 215                 220

Pro Cys Pro Gly Cys Gly Leu Leu Gly Gly Pro Ser Val Phe Ile Phe
        225                 230                 235                 240

Pro Pro Lys Pro Lys Asp Ile Leu Val Thr Ala Arg Thr Pro Thr Val
                        245                 250                 255

Thr Cys Val Val Val Asp Leu Asp Pro Glu Asn Pro Glu Val Gln Ile
                        260                 265                 270

Ser Trp Phe Val Asp Ser Lys Gln Val Gln Thr Ala Asn Thr Gln Pro
                        275                 280                 285

Arg Glu Glu Gln Ser Ala Gly Thr Tyr Arg Val Val Ser Val Leu Pro
                        290                 295                 300

Ile Gly His Gln Asp Trp Leu Ser Gly Lys Gln Phe Lys Cys Lys Val
        305                 310                 315                 320

Asn Asn Lys Ala Leu Pro Ser Pro Ile Glu Glu Ile Ser Lys Thr
                        325                 330                 335

Pro Gly Gln Ala His Gln Pro Asn Val Tyr Val Leu Pro Pro Ser Arg
                        340                 345                 350

Asp Glu Met Ser Lys Asn Thr Val Thr Leu Thr Cys Leu Val Lys Asp
                        355                 360                 365

Phe Phe Pro Pro Glu Ile Asp Val Glu Trp Gln Ser Asn Gly Gln Gln
                        370                 375                 380

Glu Pro Glu Ser Lys Tyr Arg Met Thr Pro Pro Gln Leu Asp Glu Asp
        385                 390                 395                 400

Gly Ser Tyr Phe Leu Tyr Ser Lys Leu Ser Val Asp Lys Ser Arg Trp
                        405                 410                 415

Gln Arg Gly Asp Thr Phe Ile Cys Ala Val Met His Glu Ala Leu His
                        420                 425                 430

Asn His Tyr Thr Gln Ile Ser Leu Ser His Ser Pro Gly Lys
                        435                 440                 445

<210> SEQ ID NO 13
<211> LENGTH: 444
<212> TYPE: PRT
<213> ORGANISM: Artificial Sequence
<220> FEATURE:
<223> OTHER INFORMATION: caTNFRp60:HCD Aglycosyl Fc Fusion Polypeptide
```

```
<400> SEQUENCE: 13

Met Gly Leu Pro Thr Val Pro Gly Leu Leu Pro Leu Val Leu Leu
  1               5                  10                  15

Ala Leu Leu Leu Glu Ile Tyr Pro Ile Ser Val Thr Ala Leu Val Pro
                 20                  25                  30

His Pro Arg Asn Arg Val Lys Arg Ala Ile Leu Cys Pro Gln Gly Lys
             35                  40                  45

Tyr Ile His Pro Gln Asp Asp Ser Ile Cys Cys Thr Lys Cys His Lys
 50                      55                  60

Gly Thr Tyr Leu Tyr Asn Asp Cys Pro Gly Pro Gly Leu Asp Thr Asp
 65                  70                  75                  80

Cys Arg Glu Cys Glu Asn Gly Thr Phe Thr Ala Ser Glu Asn His Leu
                 85                  90                  95

Arg Gln Cys Leu Ser Cys Ser Lys Cys Arg Lys Glu Met Asn Gln Val
                100                 105                 110

Glu Ile Ser Pro Cys Thr Val Tyr Arg Asp Thr Val Cys Gly Cys Arg
            115                 120                 125

Lys Asn Gln Tyr Arg Phe Tyr Trp Ser Glu Thr Leu Phe Gln Cys Asn
130                 135                 140

Asn Cys Ser Leu Cys Leu Asn Gly Thr Val Gln Ile Ser Cys Gln Glu
145                 150                 155                 160

Lys Gln Asn Thr Ile Cys Thr Cys His Ala Gly Phe Phe Leu Arg Glu
                165                 170                 175

His Glu Cys Val Ser Cys Val Asn Cys Lys Lys Asn Thr Glu Cys Gly
            180                 185                 190

Lys Leu Cys Leu Pro Pro Val Glu Thr Val Lys Val Pro Gln Asp Pro
        195                 200                 205

Gly Ser Thr Pro Lys Glu Ser Thr Cys Lys Cys Ile Ser Pro Cys Pro
210                 215                 220

Val Pro Glu Ser Leu Gly Gly Pro Ser Val Phe Ile Phe Pro Pro Lys
225                 230                 235                 240

Pro Lys Asp Ile Leu Arg Ile Thr Arg Thr Pro Glu Ile Thr Cys Val
                245                 250                 255

Val Leu Asp Leu Gly Arg Glu Asp Pro Glu Val Gln Ile Ser Trp Phe
            260                 265                 270

Val Asp Gly Lys Glu Val His Thr Ala Lys Thr Gln Pro Arg Glu Gln
        275                 280                 285

Gln Phe Ala Ser Thr Tyr Arg Val Val Ser Val Leu Pro Ile Glu His
    290                 295                 300

Gln Asp Trp Leu Thr Gly Lys Glu Phe Lys Cys Arg Val Asn His Ile
305                 310                 315                 320

Gly Leu Pro Ser Pro Ile Glu Arg Thr Ile Ser Lys Ala Arg Gly Gln
                325                 330                 335

Ala His Gln Pro Ser Val Tyr Val Leu Pro Pro Ser Pro Lys Glu Leu
            340                 345                 350

Ser Ser Ser Asp Thr Val Thr Leu Thr Cys Leu Ile Lys Asp Phe Tyr
        355                 360                 365

Pro Pro Glu Ile Asp Val Glu Trp Gln Ser Asn Gly Gln Pro Glu Pro
370                 375                 380

Glu Ser Lys Tyr His Thr Thr Ala Pro Gln Leu Asp Glu Asp Gly Ser
385                 390                 395                 400

Tyr Phe Leu Tyr Ser Lys Leu Ser Val Asp Lys Ser Arg Trp Gln Gln
                405                 410                 415
```

```
Gly Asp Thr Phe Thr Cys Ala Val Met His Glu Ala Leu Gln Asn His
                420                 425                 430

Tyr Thr Asp Leu Ser Leu Ser His Ser Pro Gly Lys
            435                 440

<210> SEQ ID NO 14
<211> LENGTH: 260
<212> TYPE: PRT
<213> ORGANISM: Canis familiaris

<400> SEQUENCE: 14

Met Ala Pro Ala Ala Leu Trp Ala Leu Leu Ala Ala Gly Leu Gln Leu
1               5                   10                  15

Trp Gly Ala Gly Arg Ala Val Pro Gly Gln Ala Thr Gln Leu Pro Tyr
            20                  25                  30

Val Pro Asp Pro Glu Leu Gly Ser Ser Cys Gln Gln Ser Glu Tyr Phe
        35                  40                  45

Asp Gln Arg Thr Gln Met Cys Cys Ser Met Cys Pro Pro Gly Ser His
    50                  55                  60

Ala Arg Leu Phe Cys Thr Lys Thr Ser Asn Thr Val Cys Ala Arg Cys
65                  70                  75                  80

Glu Asn Ser Thr Tyr Thr Gln Leu Trp Asn Trp Val Pro Glu Cys Leu
                85                  90                  95

Ser Cys Gly Ser Arg Cys Gly Ala Asp Gln Val Glu Thr Gln Ala Cys
            100                 105                 110

Thr Arg Glu Gln Asn Arg Ile Cys Ser Cys Lys Ser Gly Trp Tyr Cys
        115                 120                 125

Thr Leu Arg Arg Gln Gly Gly Cys Arg Leu Cys Ala Pro Leu Arg Arg
    130                 135                 140

Cys Arg Pro Gly Phe Gly Val Ala Lys Pro Gly Thr Ala Thr Ser Asp
145                 150                 155                 160

Val Val Cys Ala Pro Cys Ala Pro Gly Thr Phe Ser Asn Thr Thr Ser
                165                 170                 175

Ser Thr Asp Thr Cys Arg Pro His Arg Ile Cys Ser Ser Val Ala Val
            180                 185                 190

Pro Gly Asn Ala Ser Val Asp Ala Val Cys Ser Pro Ala Pro Pro Thr
        195                 200                 205

Val Arg Thr Ala Pro Arg Pro Ala Ser Thr Arg Gln Pro Gly Ser Thr
    210                 215                 220

Gln Pro Arg Pro Ala Glu Pro Thr Pro Gly Pro Ser Thr Pro Pro Arg
225                 230                 235                 240

Thr Ser Val Leu Phe Pro Ala Val Pro Ser Pro Pro Ala Glu Gly Leu
                245                 250                 255

Ser Thr Gly Asp
            260

<210> SEQ ID NO 15
<211> LENGTH: 493
<212> TYPE: PRT
<213> ORGANISM: Artificial Sequence
<220> FEATURE:
<223> OTHER INFORMATION: caTNFrecp80-HCA Fusion Polypeptide

<400> SEQUENCE: 15

Met Ala Pro Ala Ala Leu Trp Ala Leu Leu Ala Ala Gly Leu Gln Leu
1               5                   10                  15
```

```
Trp Gly Ala Gly Arg Ala Val Pro Gly Gln Ala Thr Gln Leu Pro Tyr
            20                  25                  30

Val Pro Asp Pro Glu Leu Gly Ser Ser Cys Gln Gln Ser Glu Tyr Phe
        35                  40                  45

Asp Gln Arg Thr Gln Met Cys Cys Ser Met Cys Pro Pro Gly Ser His
    50                  55                  60

Ala Arg Leu Phe Cys Thr Lys Thr Ser Asn Thr Val Cys Ala Arg Cys
65                  70                  75                  80

Glu Asn Ser Thr Tyr Thr Gln Leu Trp Asn Trp Val Pro Glu Cys Leu
                85                  90                  95

Ser Cys Gly Ser Arg Cys Gly Ala Asp Gln Val Glu Thr Gln Ala Cys
            100                 105                 110

Thr Arg Glu Gln Asn Arg Ile Cys Ser Cys Lys Ser Gly Trp Tyr Cys
        115                 120                 125

Thr Leu Arg Arg Gln Gly Gly Cys Arg Leu Cys Ala Pro Leu Arg Arg
    130                 135                 140

Cys Arg Pro Gly Phe Gly Val Ala Lys Pro Gly Thr Ala Thr Ser Asp
145                 150                 155                 160

Val Val Cys Ala Pro Cys Ala Pro Gly Thr Phe Ser Asn Thr Thr Ser
                165                 170                 175

Ser Thr Asp Thr Cys Arg Pro His Arg Ile Cys Ser Ser Val Ala Val
            180                 185                 190

Pro Gly Asn Ala Ser Val Asp Ala Val Cys Ser Pro Ala Pro Pro Thr
        195                 200                 205

Val Arg Thr Ala Pro Arg Pro Ala Ser Thr Arg Gln Pro Gly Ser Thr
    210                 215                 220

Gln Pro Arg Pro Ala Glu Pro Thr Pro Gly Pro Ser Thr Pro Arg
225                 230                 235                 240

Thr Ser Val Leu Phe Pro Ala Val Pro Ser Pro Ala Glu Gly Leu
                245                 250                 255

Ser Thr Gly Asp Phe Asn Glu Cys Arg Cys Thr Asp Thr Pro Pro Cys
            260                 265                 270

Pro Val Pro Glu Pro Leu Gly Gly Pro Ser Val Leu Ile Phe Pro Pro
        275                 280                 285

Lys Pro Lys Asp Ile Leu Arg Ile Thr Arg Thr Pro Glu Val Thr Cys
    290                 295                 300

Val Val Leu Asp Leu Gly Arg Glu Asp Pro Glu Val Gln Ile Ser Trp
305                 310                 315                 320

Phe Val Asp Gly Lys Glu Val His Thr Ala Lys Thr Gln Ser Arg Glu
                325                 330                 335

Gln Gln Phe Asn Gly Thr Tyr Arg Val Val Ser Val Leu Pro Ile Glu
            340                 345                 350

His Gln Asp Trp Leu Thr Gly Lys Glu Phe Lys Cys Arg Val Asn His
        355                 360                 365

Ile Asp Leu Pro Ser Pro Ile Glu Arg Thr Ile Ser Lys Ala Arg Gly
    370                 375                 380

Arg Ala His Lys Pro Ser Val Tyr Val Leu Pro Pro Ser Pro Lys Glu
385                 390                 395                 400

Leu Ser Ser Ser Asp Thr Val Ser Ile Thr Cys Leu Ile Lys Asp Phe
                405                 410                 415

Tyr Pro Pro Asp Ile Asp Val Glu Trp Gln Ser Asn Gly Gln Gln Glu
            420                 425                 430

Pro Glu Arg Lys His Arg Met Thr Pro Pro Gln Leu Asp Glu Asp Gly
```

```
                    435                 440                 445
Ser Tyr Phe Leu Tyr Ser Lys Leu Ser Val Asp Lys Ser Arg Trp Gln
    450                 455                 460

Gln Gly Asp Pro Phe Thr Cys Ala Val Met His Glu Thr Leu Gln Asn
465                 470                 475                 480

His Tyr Thr Asp Leu Ser Leu Ser His Ser Pro Gly Lys
                485                 490

<210> SEQ ID NO 16
<211> LENGTH: 497
<212> TYPE: PRT
<213> ORGANISM: Artificial Sequence
<220> FEATURE:
<223> OTHER INFORMATION: caTNFrecp80-HCB Fusion Polypeptide

<400> SEQUENCE: 16

Met Ala Pro Ala Ala Leu Trp Ala Leu Ala Ala Gly Leu Gln Leu
1               5                   10                  15

Trp Gly Ala Gly Arg Ala Val Pro Gly Gln Ala Thr Gln Leu Pro Tyr
                20                  25                  30

Val Pro Asp Pro Glu Leu Gly Ser Ser Cys Gln Gln Ser Glu Tyr Phe
            35                  40                  45

Asp Gln Arg Thr Gln Met Cys Cys Ser Met Cys Pro Pro Gly Ser His
    50                  55                  60

Ala Arg Leu Phe Cys Thr Lys Thr Ser Asn Thr Val Cys Ala Arg Cys
65                  70                  75                  80

Glu Asn Ser Thr Tyr Thr Gln Leu Trp Asn Trp Val Pro Glu Cys Leu
                85                  90                  95

Ser Cys Gly Ser Arg Cys Gly Ala Asp Gln Val Glu Thr Gln Ala Cys
            100                 105                 110

Thr Arg Glu Gln Asn Arg Ile Cys Ser Cys Lys Ser Gly Trp Tyr Cys
    115                 120                 125

Thr Leu Arg Arg Gln Gly Gly Cys Arg Leu Cys Ala Pro Leu Arg Arg
130                 135                 140

Cys Arg Pro Gly Phe Gly Val Ala Lys Pro Gly Thr Ala Thr Ser Asp
145                 150                 155                 160

Val Val Cys Ala Pro Cys Ala Pro Gly Thr Phe Ser Asn Thr Thr Ser
                165                 170                 175

Ser Thr Asp Thr Cys Arg Pro His Arg Ile Cys Ser Ser Val Ala Val
            180                 185                 190

Pro Gly Asn Ala Ser Val Asp Ala Val Cys Ser Pro Ala Pro Pro Thr
    195                 200                 205

Val Arg Thr Ala Pro Arg Pro Ala Ser Thr Arg Gln Pro Gly Ser Thr
210                 215                 220

Gln Pro Arg Pro Ala Glu Pro Thr Pro Gly Pro Ser Thr Pro Pro Arg
225                 230                 235                 240

Thr Ser Val Leu Phe Pro Ala Val Pro Ser Pro Ala Glu Gly Leu
                245                 250                 255

Ser Thr Gly Asp Pro Lys Arg Glu Asn Gly Arg Val Pro Arg Pro Pro
            260                 265                 270

Asp Cys Pro Lys Cys Pro Ala Pro Glu Met Leu Gly Gly Pro Ser Val
    275                 280                 285

Phe Ile Phe Pro Pro Lys Pro Lys Asp Thr Leu Leu Ile Ala Arg Thr
290                 295                 300

Pro Glu Val Thr Cys Val Val Val Asp Leu Asp Pro Glu Asp Pro Glu
```

```
            305                 310                 315                 320
Val Gln Ile Ser Trp Phe Val Asp Gly Lys Gln Met Gln Thr Ala Lys
                325                 330                 335

Thr Gln Pro Arg Glu Glu Gln Phe Asn Gly Thr Tyr Arg Val Val Ser
                340                 345                 350

Val Leu Pro Ile Gly His Gln Asp Trp Leu Lys Gly Lys Gln Phe Thr
                355                 360                 365

Cys Lys Val Asn Asn Lys Ala Leu Pro Ser Pro Ile Glu Arg Thr Ile
            370                 375                 380

Ser Lys Ala Arg Gly Gln Ala His Gln Pro Ser Val Tyr Val Leu Pro
385                 390                 395                 400

Pro Ser Arg Glu Glu Leu Ser Lys Asn Thr Val Ser Leu Thr Cys Leu
                405                 410                 415

Ile Lys Asp Phe Tyr Pro Pro Asp Ile Asp Val Glu Trp Gln Ser Asn
                420                 425                 430

Gly Gln Gln Glu Pro Glu Ser Lys Tyr Arg Thr Thr Pro Pro Gln Leu
            435                 440                 445

Asp Glu Asp Gly Ser Tyr Phe Leu Tyr Ser Lys Leu Ser Val Asp Lys
            450                 455                 460

Ser Arg Trp Gln Arg Gly Asp Thr Phe Ile Cys Ala Val Met His Glu
465                 470                 475                 480

Ala Leu His Asn His Tyr Thr Gln Glu Ser Leu Ser His Ser Pro Gly
                485                 490                 495

Lys

<210> SEQ ID NO 17
<211> LENGTH: 495
<212> TYPE: PRT
<213> ORGANISM: Artificial Sequence
<220> FEATURE:
<223> OTHER INFORMATION: caTNFrecp80-HCC Fusion Polypeptide

<400> SEQUENCE: 17

Met Ala Pro Ala Ala Leu Trp Ala Leu Leu Ala Ala Gly Leu Gln Leu
1               5                   10                  15

Trp Gly Ala Gly Arg Ala Val Pro Gly Gln Ala Thr Gln Leu Pro Tyr
                20                  25                  30

Val Pro Asp Pro Glu Leu Gly Ser Ser Cys Gln Gln Ser Glu Tyr Phe
            35                  40                  45

Asp Gln Arg Thr Gln Met Cys Cys Ser Met Cys Pro Pro Gly Ser His
        50                  55                  60

Ala Arg Leu Phe Cys Thr Lys Thr Ser Asn Thr Val Cys Ala Arg Cys
65              70                  75                  80

Glu Asn Ser Thr Tyr Thr Gln Leu Trp Asn Trp Val Pro Glu Cys Leu
                85                  90                  95

Ser Cys Gly Ser Arg Cys Gly Ala Asp Gln Val Glu Thr Gln Ala Cys
            100                 105                 110

Thr Arg Glu Gln Asn Arg Ile Cys Ser Cys Lys Ser Gly Trp Tyr Cys
        115                 120                 125

Thr Leu Arg Arg Gln Gly Gly Cys Arg Leu Cys Ala Pro Leu Arg Arg
    130                 135                 140

Cys Arg Pro Gly Phe Gly Val Ala Lys Pro Gly Thr Ala Thr Ser Asp
145                 150                 155                 160

Val Val Cys Ala Pro Cys Ala Pro Gly Thr Phe Ser Asn Thr Thr Ser
                165                 170                 175
```

Ser Thr Asp Thr Cys Arg Pro His Arg Ile Cys Ser Val Ala Val
            180                 185                 190

Pro Gly Asn Ala Ser Val Asp Ala Val Cys Ser Pro Ala Pro Pro Thr
        195                 200                 205

Val Arg Thr Ala Pro Arg Pro Ala Ser Thr Arg Gln Pro Gly Ser Thr
    210                 215                 220

Gln Pro Arg Pro Ala Glu Pro Thr Pro Gly Pro Ser Thr Pro Pro Arg
225                 230                 235                 240

Thr Ser Val Leu Phe Pro Ala Val Pro Ser Pro Pro Ala Glu Gly Leu
                245                 250                 255

Ser Thr Gly Asp Ala Lys Glu Cys Glu Cys Lys Cys Asn Cys Asn Asn
            260                 265                 270

Cys Pro Cys Pro Gly Cys Gly Leu Leu Gly Pro Ser Val Phe Ile
        275                 280                 285

Phe Pro Pro Lys Pro Lys Asp Ile Leu Val Thr Ala Arg Thr Pro Thr
    290                 295                 300

Val Thr Cys Val Val Val Asp Leu Asp Pro Glu Asn Pro Glu Val Gln
305                 310                 315                 320

Ile Ser Trp Phe Val Asp Ser Lys Gln Val Gln Thr Ala Asn Thr Gln
                325                 330                 335

Pro Arg Glu Glu Gln Ser Asn Gly Thr Tyr Arg Val Val Ser Val Leu
            340                 345                 350

Pro Ile Gly His Gln Asp Trp Leu Ser Gly Lys Gln Phe Lys Cys Lys
        355                 360                 365

Val Asn Asn Lys Ala Leu Pro Ser Pro Ile Glu Glu Ile Ile Ser Lys
    370                 375                 380

Thr Pro Gly Gln Ala His Gln Pro Asn Val Tyr Val Leu Pro Pro Ser
385                 390                 395                 400

Arg Asp Glu Met Ser Lys Asn Thr Val Thr Leu Thr Cys Leu Val Lys
                405                 410                 415

Asp Phe Phe Pro Pro Glu Ile Asp Val Glu Trp Gln Ser Asn Gly Gln
            420                 425                 430

Gln Glu Pro Glu Ser Lys Tyr Arg Met Thr Pro Gln Leu Asp Glu
        435                 440                 445

Asp Gly Ser Tyr Phe Leu Tyr Ser Lys Leu Ser Val Asp Lys Ser Arg
    450                 455                 460

Trp Gln Arg Gly Asp Thr Phe Ile Cys Ala Val Met His Glu Ala Leu
465                 470                 475                 480

His Asn His Tyr Thr Gln Ile Ser Leu Ser His Ser Pro Gly Lys
                485                 490                 495

<210> SEQ ID NO 18
<211> LENGTH: 493
<212> TYPE: PRT
<213> ORGANISM: Artificial Sequence
<220> FEATURE:
<223> OTHER INFORMATION: caTNFrecp80-HCD Fusion Polypeptide

<400> SEQUENCE: 18

Met Ala Pro Ala Ala Leu Trp Ala Leu Leu Ala Ala Gly Leu Gln Leu
1               5                   10                  15

Trp Gly Ala Gly Arg Ala Val Pro Gly Gln Ala Thr Gln Leu Pro Tyr
            20                  25                  30

Val Pro Asp Pro Glu Leu Gly Ser Ser Cys Gln Gln Ser Glu Tyr Phe
        35                  40                  45

```
Asp Gln Arg Thr Gln Met Cys Cys Ser Met Cys Pro Gly Ser His
     50                  55                  60

Ala Arg Leu Phe Cys Thr Lys Thr Ser Asn Thr Val Cys Ala Arg Cys
65                   70                  75                  80

Glu Asn Ser Thr Tyr Thr Gln Leu Trp Asn Trp Val Pro Glu Cys Leu
                 85                  90                  95

Ser Cys Gly Ser Arg Cys Gly Ala Asp Gln Val Glu Thr Gln Ala Cys
            100                 105                 110

Thr Arg Glu Gln Asn Arg Ile Cys Ser Cys Lys Ser Gly Trp Tyr Cys
        115                 120                 125

Thr Leu Arg Arg Gln Gly Gly Cys Arg Leu Cys Ala Pro Leu Arg Arg
    130                 135                 140

Cys Arg Pro Gly Phe Gly Val Ala Lys Pro Gly Thr Ala Thr Ser Asp
145                 150                 155                 160

Val Val Cys Ala Pro Cys Ala Pro Gly Thr Phe Ser Asn Thr Thr Ser
                165                 170                 175

Ser Thr Asp Thr Cys Arg Pro His Arg Ile Cys Ser Ser Val Ala Val
            180                 185                 190

Pro Gly Asn Ala Ser Val Asp Ala Val Cys Ser Pro Ala Pro Pro Thr
        195                 200                 205

Val Arg Thr Ala Pro Arg Pro Ala Ser Thr Arg Gln Pro Gly Ser Thr
    210                 215                 220

Gln Pro Arg Pro Ala Glu Pro Thr Pro Gly Pro Ser Thr Pro Pro Arg
225                 230                 235                 240

Thr Ser Val Leu Phe Pro Ala Val Pro Ser Pro Ala Glu Gly Leu
                245                 250                 255

Ser Thr Gly Asp Pro Lys Glu Ser Thr Cys Lys Cys Ile Ser Pro Cys
            260                 265                 270

Pro Val Pro Glu Ser Leu Gly Gly Pro Ser Val Phe Ile Phe Pro Pro
        275                 280                 285

Lys Pro Lys Asp Ile Leu Arg Ile Thr Arg Thr Pro Glu Ile Thr Cys
    290                 295                 300

Val Val Leu Asp Leu Gly Arg Glu Asp Pro Glu Val Gln Ile Ser Trp
305                 310                 315                 320

Phe Val Asp Gly Lys Glu Val His Thr Ala Lys Thr Gln Pro Arg Glu
                325                 330                 335

Gln Gln Phe Asn Ser Thr Tyr Arg Val Val Ser Val Leu Pro Ile Glu
            340                 345                 350

His Gln Asp Trp Leu Thr Gly Lys Glu Phe Lys Cys Arg Val Asn His
        355                 360                 365

Ile Gly Leu Pro Ser Pro Ile Glu Arg Thr Ile Ser Lys Ala Arg Gly
    370                 375                 380

Gln Ala His Gln Pro Ser Val Tyr Val Leu Pro Pro Ser Pro Lys Glu
385                 390                 395                 400

Leu Ser Ser Ser Asp Thr Val Thr Leu Thr Cys Leu Ile Lys Asp Phe
                405                 410                 415

Tyr Pro Pro Glu Ile Asp Val Glu Trp Gln Ser Asn Gly Gln Pro Glu
            420                 425                 430

Pro Glu Ser Lys Tyr His Thr Thr Ala Pro Gln Leu Asp Glu Asp Gly
        435                 440                 445

Ser Tyr Phe Leu Tyr Ser Lys Leu Ser Val Asp Lys Ser Arg Trp Gln
    450                 455                 460
```

Gln Gly Asp Thr Phe Thr Cys Ala Val Met His Glu Ala Leu Gln Asn
465                 470                 475                 480

His Tyr Thr Asp Leu Ser Leu Ser His Ser Pro Gly Lys
            485                 490

<210> SEQ ID NO 19
<211> LENGTH: 493
<212> TYPE: PRT
<213> ORGANISM: Artificial Sequence
<220> FEATURE:
<223> OTHER INFORMATION: caTNFrecp80-aglycosyl HCA Fc Fusion Polypeptide

<400> SEQUENCE: 19

Met Ala Pro Ala Ala Leu Trp Ala Leu Leu Ala Ala Gly Leu Gln Leu
1               5                   10                  15

Trp Gly Ala Gly Arg Ala Val Pro Gly Gln Ala Thr Gln Leu Pro Tyr
            20                  25                  30

Val Pro Asp Pro Glu Leu Gly Ser Ser Cys Gln Gln Ser Glu Tyr Phe
        35                  40                  45

Asp Gln Arg Thr Gln Met Cys Cys Ser Met Cys Pro Pro Gly Ser His
    50                  55                  60

Ala Arg Leu Phe Cys Thr Lys Thr Ser Asn Thr Val Cys Ala Arg Cys
65                  70                  75                  80

Glu Asn Ser Thr Tyr Thr Gln Leu Trp Asn Trp Val Pro Glu Cys Leu
                85                  90                  95

Ser Cys Gly Ser Arg Cys Gly Ala Asp Gln Val Glu Thr Gln Ala Cys
            100                 105                 110

Thr Arg Glu Gln Asn Arg Ile Cys Ser Cys Lys Ser Gly Trp Tyr Cys
        115                 120                 125

Thr Leu Arg Arg Gln Gly Gly Cys Arg Leu Cys Ala Pro Leu Arg Arg
    130                 135                 140

Cys Arg Pro Gly Phe Gly Val Ala Lys Pro Gly Thr Ala Thr Ser Asp
145                 150                 155                 160

Val Val Cys Ala Pro Cys Ala Pro Gly Thr Phe Ser Asn Thr Thr Ser
                165                 170                 175

Ser Thr Asp Thr Cys Arg Pro His Arg Ile Cys Ser Ser Val Ala Val
            180                 185                 190

Pro Gly Asn Ala Ser Val Asp Ala Val Cys Ser Pro Ala Pro Pro Thr
        195                 200                 205

Val Arg Thr Ala Pro Arg Pro Ala Ser Thr Arg Gln Pro Gly Ser Thr
    210                 215                 220

Gln Pro Arg Pro Ala Glu Pro Thr Pro Gly Pro Ser Thr Pro Pro Arg
225                 230                 235                 240

Thr Ser Val Leu Phe Pro Ala Val Pro Ser Pro Ala Glu Gly Leu
                245                 250                 255

Ser Thr Gly Asp Phe Asn Glu Cys Arg Cys Thr Asp Thr Pro Pro Cys
            260                 265                 270

Pro Val Pro Glu Pro Leu Gly Gly Pro Ser Val Leu Ile Phe Pro Pro
        275                 280                 285

Lys Pro Lys Asp Ile Leu Arg Ile Thr Arg Thr Pro Glu Val Thr Cys
    290                 295                 300

Val Val Leu Asp Leu Gly Arg Glu Asp Pro Glu Val Gln Ile Ser Trp
305                 310                 315                 320

Phe Val Asp Gly Lys Glu Val His Thr Ala Lys Thr Gln Ser Arg Glu
                325                 330                 335

```
Gln Gln Phe Ala Gly Thr Tyr Arg Val Val Ser Val Leu Pro Ile Glu
            340                 345                 350

His Gln Asp Trp Leu Thr Gly Lys Glu Phe Lys Cys Arg Val Asn His
        355                 360                 365

Ile Asp Leu Pro Ser Pro Ile Glu Arg Thr Ile Ser Lys Ala Arg Gly
    370                 375                 380

Arg Ala His Lys Pro Ser Val Tyr Val Leu Pro Pro Ser Pro Lys Glu
385                 390                 395                 400

Leu Ser Ser Ser Asp Thr Val Ser Ile Thr Cys Leu Ile Lys Asp Phe
                405                 410                 415

Tyr Pro Pro Asp Ile Asp Val Glu Trp Gln Ser Asn Gly Gln Gln Glu
            420                 425                 430

Pro Glu Arg Lys His Arg Met Thr Pro Pro Gln Leu Asp Glu Asp Gly
        435                 440                 445

Ser Tyr Phe Leu Tyr Ser Lys Leu Ser Val Asp Lys Ser Arg Trp Gln
    450                 455                 460

Gln Gly Asp Pro Phe Thr Cys Ala Val Met His Glu Thr Leu Gln Asn
465                 470                 475                 480

His Tyr Thr Asp Leu Ser Leu Ser His Ser Pro Gly Lys
                485                 490
```

<210> SEQ ID NO 20
<211> LENGTH: 497
<212> TYPE: PRT
<213> ORGANISM: Artificial Sequence
<220> FEATURE:
<223> OTHER INFORMATION: caTNFrecp80-aglycosyl HCB Fc Fusion Polypeptide

<400> SEQUENCE: 20

```
Met Ala Pro Ala Ala Leu Trp Ala Leu Leu Ala Gly Leu Gln Leu
1               5                   10                  15

Trp Gly Ala Gly Arg Ala Val Pro Gly Gln Ala Thr Gln Leu Pro Tyr

-continued

Val Arg Thr Ala Pro Arg Pro Ala Ser Thr Arg Gln Pro Gly Ser Thr
    210             215                 220

Gln Pro Arg Pro Ala Glu Pro Thr Pro Gly Pro Ser Thr Pro Pro Arg
225             230                 235                 240

Thr Ser Val Leu Phe Pro Ala Val Pro Ser Pro Pro Ala Glu Gly Leu
            245                 250                 255

Ser Thr Gly Asp Pro Lys Arg Glu Asn Gly Arg Val Pro Arg Pro Pro
            260                 265                 270

Asp Cys Pro Lys Cys Pro Ala Pro Glu Met Leu Gly Gly Pro Ser Val
        275                 280                 285

Phe Ile Phe Pro Pro Lys Pro Lys Asp Thr Leu Leu Ile Ala Arg Thr
290                 295                 300

Pro Glu Val Thr Cys Val Val Val Asp Leu Asp Pro Glu Asp Pro Glu
305             310                 315                 320

Val Gln Ile Ser Trp Phe Val Asp Gly Lys Gln Met Gln Thr Ala Lys
                325                 330                 335

Thr Gln Pro Arg Glu Glu Gln Phe Ala Gly Thr Tyr Arg Val Val Ser
            340                 345                 350

Val Leu Pro Ile Gly His Gln Asp Trp Leu Lys Gly Lys Gln Phe Thr
        355                 360                 365

Cys Lys Val Asn Asn Lys Ala Leu Pro Ser Pro Ile Glu Arg Thr Ile
    370                 375                 380

Ser Lys Ala Arg Gly Gln Ala His Gln Pro Ser Val Tyr Val Leu Pro
385                 390                 395                 400

Pro Ser Arg Glu Glu Leu Ser Lys Asn Thr Val Ser Leu Thr Cys Leu
                405                 410                 415

Ile Lys Asp Phe Tyr Pro Pro Asp Ile Asp Val Glu Trp Gln Ser Asn
            420                 425                 430

Gly Gln Gln Glu Pro Glu Ser Lys Tyr Arg Thr Thr Pro Pro Gln Leu
        435                 440                 445

Asp Glu Asp Gly Ser Tyr Phe Leu Tyr Ser Lys Leu Ser Val Asp Lys
    450                 455                 460

Ser Arg Trp Gln Arg Gly Asp Thr Phe Ile Cys Ala Val Met His Glu
465                 470                 475                 480

Ala Leu His Asn His Tyr Thr Gln Glu Ser Leu Ser His Ser Pro Gly
                485                 490                 495

Lys

<210> SEQ ID NO 21
<211> LENGTH: 495
<212> TYPE: PRT
<213> ORGANISM: Artificial Sequence
<220> FEATURE:
<223> OTHER INFORMATION: caTNFrecp80-aglycosyl HCC Fc Fusion Polypeptide

<400> SEQUENCE: 21

Met Ala Pro Ala Ala Leu Trp Ala Leu Leu Ala Ala Gly Leu Gln Leu
1               5                   10                  15

Trp Gly Ala Gly Arg Ala Val Pro Gly Gln Ala Thr Gln Leu Pro Tyr
            20                  25                  30

Val Pro Asp Pro Glu Leu Gly Ser Ser Cys Gln Gln Ser Glu Tyr Phe
        35                  40                  45

Asp Gln Arg Thr Gln Met Cys Cys Ser Met Cys Pro Pro Gly Ser His
    50                  55                  60

Ala Arg Leu Phe Cys Thr Lys Thr Ser Asn Thr Val Cys Ala Arg Cys

```
            65                  70                  75                  80
Glu Asn Ser Thr Tyr Thr Gln Leu Trp Asn Trp Val Pro Glu Cys Leu
                    85                  90                  95

Ser Cys Gly Ser Arg Cys Gly Ala Asp Gln Val Glu Thr Gln Ala Cys
                100                 105                 110

Thr Arg Glu Gln Asn Arg Ile Cys Ser Cys Lys Ser Gly Trp Tyr Cys
                115                 120                 125

Thr Leu Arg Arg Gln Gly Gly Cys Arg Leu Cys Ala Pro Leu Arg Arg
            130                 135                 140

Cys Arg Pro Gly Phe Gly Val Ala Lys Pro Gly Thr Ala Thr Ser Asp
145                 150                 155                 160

Val Val Cys Ala Pro Cys Ala Pro Gly Thr Phe Ser Asn Thr Thr Ser
                165                 170                 175

Ser Thr Asp Thr Cys Arg Pro His Arg Ile Cys Ser Ser Val Ala Val
            180                 185                 190

Pro Gly Asn Ala Ser Val Asp Ala Val Cys Ser Pro Ala Pro Pro Thr
            195                 200                 205

Val Arg Thr Ala Pro Arg Pro Ala Ser Thr Arg Gln Pro Gly Ser Thr
        210                 215                 220

Gln Pro Arg Pro Ala Glu Pro Thr Pro Gly Pro Ser Thr Pro Pro Arg
225                 230                 235                 240

Thr Ser Val Leu Phe Pro Ala Val Pro Ser Pro Ala Glu Gly Leu
                245                 250                 255

Ser Thr Gly Asp Ala Lys Glu Cys Glu Cys Lys Cys Asn Cys Asn Asn
            260                 265                 270

Cys Pro Cys Pro Gly Cys Gly Leu Leu Gly Gly Pro Ser Val Phe Ile
        275                 280                 285

Phe Pro Pro Lys Pro Lys Asp Ile Leu Val Thr Ala Arg Thr Pro Thr
        290                 295                 300

Val Thr Cys Val Val Asp Leu Asp Pro Glu Asn Pro Glu Val Gln
305                 310                 315                 320

Ile Ser Trp Phe Val Asp Ser Lys Gln Val Gln Thr Ala Asn Thr Gln
                325                 330                 335

Pro Arg Glu Glu Gln Ser Ala Gly Thr Tyr Arg Val Val Ser Val Leu
            340                 345                 350

Pro Ile Gly His Gln Asp Trp Leu Ser Gly Lys Gln Phe Lys Cys Lys
            355                 360                 365

Val Asn Asn Lys Ala Leu Pro Ser Pro Ile Glu Glu Ile Ser Lys
        370                 375                 380

Thr Pro Gly Gln Ala His Gln Pro Asn Val Tyr Val Leu Pro Pro Ser
385                 390                 395                 400

Arg Asp Glu Met Ser Lys Asn Thr Val Thr Leu Thr Cys Leu Val Lys
                405                 410                 415

Asp Phe Phe Pro Pro Glu Ile Asp Val Glu Trp Gln Ser Asn Gly Gln
                420                 425                 430

Gln Glu Pro Glu Ser Lys Tyr Arg Met Thr Pro Pro Gln Leu Asp Glu
            435                 440                 445

Asp Gly Ser Tyr Phe Leu Tyr Ser Lys Leu Ser Val Asp Lys Ser Arg
            450                 455                 460

Trp Gln Arg Gly Asp Thr Phe Ile Cys Ala Val Met His Glu Ala Leu
465                 470                 475                 480

His Asn His Tyr Thr Gln Ile Ser Leu Ser His Ser Pro Gly Lys
                485                 490                 495
```

<210> SEQ ID NO 22
<211> LENGTH: 493
<212> TYPE: PRT
<213> ORGANISM: Artificial Sequence
<220> FEATURE:
<223> OTHER INFORMATION: caTNFrecp80-aglycosyl HCD Fc Fusion Polypeptide

<400> SEQUENCE: 22

```
Met Ala Pro Ala Ala Leu Trp Ala Leu Leu Ala Gly Leu Gln Leu
1               5                   10                  15

Trp Gly Ala Gly Arg Ala Val Pro Gly Gln Ala Thr Gln Leu Pro Tyr
            20                  25                  30

Val Pro Asp Pro Glu Leu Gly Ser Ser Cys Gln Gln Ser Glu Tyr Phe
        35                  40                  45

Asp Gln Arg Thr Gln Met Cys Cys Ser Met Cys Pro Pro Gly Ser His
    50                  55                  60

Ala Arg Leu Phe Cys Thr Lys Thr Ser Asn Thr Val Cys Ala Arg Cys
65                  70                  75                  80

Glu Asn Ser Thr Tyr Thr Gln Leu Trp Asn Trp Val Pro Glu Cys Leu
                85                  90                  95

Ser Cys Gly Ser Arg Cys Gly Ala Asp Gln Val Glu Thr Gln Ala Cys
            100                 105                 110

Thr Arg Glu Gln Asn Arg Ile Cys Ser Cys Lys Ser Gly Trp Tyr Cys
        115                 120                 125

Thr Leu Arg Arg Gln Gly Gly Cys Arg Leu Cys Ala Pro Leu Arg Arg
    130                 135                 140

Cys Arg Pro Gly Phe Gly Val Ala Lys Pro Gly Thr Ala Thr Ser Asp
145                 150                 155                 160

Val Val Cys Ala Pro Cys Ala Pro Gly Thr Phe Ser Asn Thr Thr Ser
                165                 170                 175

Ser Thr Asp Thr Cys Arg Pro His Arg Ile Cys Ser Ser Val Ala Val
            180                 185                 190

Pro Gly Asn Ala Ser Val Asp Ala Val Cys Ser Pro Ala Pro Pro Thr
        195                 200                 205

Val Arg Thr Ala Pro Arg Pro Ala Ser Thr Arg Gln Pro Gly Ser Thr
    210                 215                 220

Gln Pro Arg Pro Ala Glu Pro Thr Pro Gly Pro Ser Thr Pro Arg
225                 230                 235                 240

Thr Ser Val Leu Phe Pro Ala Val Pro Ser Pro Ala Glu Gly Leu
                245                 250                 255

Ser Thr Gly Asp Pro Lys Glu Ser Thr Cys Lys Cys Ile Ser Pro Cys
            260                 265                 270

Pro Val Pro Glu Ser Leu Gly Gly Pro Ser Val Phe Ile Phe Pro Pro
        275                 280                 285

Lys Pro Lys Asp Ile Leu Arg Ile Thr Arg Thr Pro Glu Ile Thr Cys
    290                 295                 300

Val Val Leu Asp Leu Gly Arg Glu Asp Pro Glu Val Gln Ile Ser Trp
305                 310                 315                 320

Phe Val Asp Gly Lys Glu Val His Thr Ala Lys Thr Gln Pro Arg Glu
                325                 330                 335

Gln Gln Phe Ala Ser Thr Tyr Arg Val Val Ser Val Leu Pro Ile Glu
            340                 345                 350

His Gln Asp Trp Leu Thr Gly Lys Glu Phe Lys Cys Arg Val Asn His
        355                 360                 365
```

Ile Gly Leu Pro Ser Pro Ile Glu Arg Thr Ile Ser Lys Ala Arg Gly
    370             375                 380

Gln Ala His Gln Pro Ser Val Tyr Val Leu Pro Ser Pro Lys Glu
385             390                 395                 400

Leu Ser Ser Ser Asp Thr Val Thr Leu Thr Cys Leu Ile Lys Asp Phe
                405                 410                 415

Tyr Pro Pro Glu Ile Asp Val Glu Trp Gln Ser Asn Gly Gln Pro Glu
            420                 425                 430

Pro Glu Ser Lys Tyr His Thr Thr Ala Pro Gln Leu Asp Glu Asp Gly
        435                 440                 445

Ser Tyr Phe Leu Tyr Ser Lys Leu Ser Val Asp Lys Ser Arg Trp Gln
    450                 455                 460

Gln Gly Asp Thr Phe Thr Cys Ala Val Met His Glu Ala Leu Gln Asn
465             470                 475                 480

His Tyr Thr Asp Leu Ser Leu Ser His Ser Pro Gly Lys
                485                 490

<210> SEQ ID NO 23
<211> LENGTH: 633
<212> TYPE: DNA
<213> ORGANISM: Canis familiaris

<400> SEQUENCE: 23
atgggcctgc caccgtgcc tggactgctg ctgcctctgg tgctgctggc cctgctgctg      60
gaaatctacc ccatcagcgt gaccgccctg gtgccccacc cccggaacag agtgaagcgg    120
gccatcctgt gtccacaggg caagtacatc caccctcagg acgacagcat ctgctgcacc    180
aagtgccaca agggcaccta cctgtacaac gactgccccg gacccggcct ggacaccgat    240
tgcagagagt gcgagaacgg caccttcacc gccagcgaga accacctgag acagtgcctg    300
tcctgcagca gtgcagaaa agagatgaac caggtcgaga tcagcccctg caccgtgtac    360
cgggacaccg tgtgcggctg ccggaagaac cagtacagat tctattggag cgagacactg    420
ttccagtgca caactgcag cctgtgcctg aatggcaccg tgcagatcag ctgccaggaa    480
aagcagaaca ccatctgcac ctgtcacgcc ggattctttc tgcgcgagca cgagtgcgtg    540
tcctgtgtga actgcaagaa aaacaccgag tgtggcaagc tgtgcctgcc cctgtggaa     600 accgtgaaag tgcctcagga ccctggcagc aca                                  633

<210> SEQ ID NO 24
<211> LENGTH: 702
<212> TYPE: DNA
<213> ORGANISM: Canis familiaris

<400> SEQUENCE: 24
ttcaacgagt gccggtgtac cgacaccccc ccttgtcctg tgcctgagcc tctgggcgga    60
ccctccgtgc tgatcttccc acccaagccc aaggacatcc tgcggatcac ccggaccccc    120
gaagtgacct gcgtggtgct ggatctgggc cgcgaggacc ctgaggtgca gatcagttgg    180
ttcgtggacg gcaaagaggt gcacaccgct aagacccaga gcagagagca gcagttcaac    240
ggcacctaca gagtggtgtc cgtgctgccc atcgagcacc aggactggct gaccggcaaa    300
gagttcaagt gcagagtcaa ccacatcgac ctgcctagcc ctatcgagcg accatcagc    360 aaggccagag gcagagccca caagcccagc gtgtacgtgc tcccacccag ccccaaagag    420
ctgagcagca gcgacaccgt gtccatcacc tgtctgatca aggacttcta ccccccgac    480

| atcgacgtgg aatggcagag caacggacag caggaacccg agcggaagca cagaatgacc | 540 |
| cccccacagc tggacgagga cggcagctac ttcctgtaca gcaagctgag cgtggacaag | 600 |
| agccggtggc agcagggcga ccccttcaca tgtgccgtga tgcacgagac actgcagaac | 660 |
| cactacaccg acctgtctct gagccacagc cccggcaagt ga | 702 |

<210> SEQ ID NO 25
<211> LENGTH: 714
<212> TYPE: DNA
<213> ORGANISM: Canis familiaris

<400> SEQUENCE: 25

| cccaagcgcg agaacggcag agtgcccaga ccccccgact gccctaagtg tcccgcccct | 60 |
| gagatgctgg gcggaccctc cgtgttcatc ttcccaccca gcccaaggga caccctgctg | 120 |
| atcgcccgga cccccgaagt gacctgcgtg gtggtggacc tggaccccga ggaccctgag | 180 |
| gtgcagatca gttggttcgt ggacggcaag cagatgcaga ccgccaagac ccagcccaga | 240 |
| gaggaacagt tcaacggcac ctaccgggtg gtgtccgtcc tgcctatcgg ccaccaggac | 300 |
| tggctgaagg gcaagcagtt tacctgcaaa gtgaacaaca aggccctgcc tagccccatc | 360 |
| gagcggacca tcagcaaggc cagaggccag gcccaccagc ccagcgtgta cgtgctgccc | 420 |
| cccagccggg aagaactgag caagaatacc gtgtccctga cctgcctgat caaggacttc | 480 |
| tacccccccg acatcgacgt ggaatggcag agcaacggcc agcaggaacc cgagagcaag | 540 |
| taccggacca ccccccccaca gctggacgag gacggcagct acttcctgta cagcaagctg | 600 |
| agcgtggaca gagccggtg gcagcggggc gacaccttca tctgcgccgt gatgcacgag | 660 |
| gccctgcaca accactacac ccaggaaagc ctgtctcaca gccccggcaa gtga | 714 |

<210> SEQ ID NO 26
<211> LENGTH: 708
<212> TYPE: DNA
<213> ORGANISM: Canis familiaris

<400> SEQUENCE: 26

| gctaaagaat gcgagtgcaa gtgcaactgc aacaactgcc cctgtcctgg ctgcggactg | 60 |
| ctgggaggac ctagcgtgtt catcttccca cccaagccca aggacatcct ggtcaccgcc | 120 |
| cggaccccca ccgtgacatg cgtggtggtg gacctggacc ccgagaaccc cgaggtgcag | 180 |
| atcagttggt tcgtggacag caaacaggtg cagaccgcca cacccagcc cagagaggaa | 240 |
| cagagcaacg gcacctacag agtggtgtct gtgctgccta tcggccacca ggactggctg | 300 |
| agcggcaagc agttcaagtg caaagtgaac aacaaggccc tgcctagccc catcgaggaa | 360 |
| atcatcagca gacccctgg acaggcccac cagcctaacg tgtacgtcct gcctcccagc | 420 |
| cgggacgaga tgtccaagaa caccgtgacc ctgacttgcc tggtcaagga cttcttcccc | 480 |
| cccgaaatcg acgtggaatg gcagtccaac ggccagcagg aacccgagag caagtaccgg | 540 |
| atgaccccc cacagctgga cgaggacggc agctacttcc tgtacagcaa gctgagcgtg | 600 |
| gacaagagcc ggtggcagcg gggcgacacc ttcatctgcg ccgtgatgca cgaggccctg | 660 |
| cacaaccact acacccagat cagcctgagc cacagccccg gcaagtga | 708 |

<210> SEQ ID NO 27
<211> LENGTH: 702
<212> TYPE: DNA
<213> ORGANISM: Canis familiaris

<400> SEQUENCE: 27

```
cccaaagaaa gcacatgcaa gtgcatcagc ccctgtcccg tgcctgagtc tctgggaggc    60
ccttccgtgt tcatcttccc acccaagccc aaggacatcc tgcggatcac ccggaccccc   120
gagatcacct gtgtggtgct ggacctgggc cgcgaggacc ctgaggtgca gatcagttgg   180
ttcgtggacg gcaaagaggt gcacaccgct aagacccagc ccagagagca gcagttcaac   240
agcacctacc gggtggtgtc cgtcctgccc atcgagcacc aggactggct gaccggcaaa   300
gagttcaagt gcagagtcaa ccacatcggc ctgcccagcc ctatcgagcg gaccatcagc   360
aaggccagag ccaggcccca ccagcccagc gtgtacgtgc tgccacctag ccccaaagag   420
ctgagcagca gcgacaccgt gaccctgacc tgcctgatca aggacttcta ccccccgaa    480 atcgacgtgg aatggcagag caacggacag cctgagcccg agagcaagta ccacaccaca   540
gccccccagc tggacgagga cggcagctac ttcctgtaca gcaagctgag cgtggacaag   600
agccggtggc agcagggcga caccttcaca tgtgccgtga tgcacgaggc cctgcagaac   660
cactacaccg acctgagcct gagccacagc cccggcaagt ga                     702

<210> SEQ ID NO 28
<211> LENGTH: 1335
<212> TYPE: DNA
<213> ORGANISM: Artificial Sequence
<220> FEATURE:
<223> OTHER INFORMATION: caTNFRp60-HCA - nucleotide sequence encoding
      SEQ ID NO:6

<400> SEQUENCE: 28
atgggcctgc ccaccgtgcc tggactgctg ctgcctctgg tgctgctggc cctgctgctg    60
gaaatctacc ccatcagcgt gaccgccctg gtgccccacc ccggaacag agtgaagcgg   120 gccatcctgt gtccacaggg caagtacatc caccctcagg acgacagcat ctgctgcacc   180
aagtgccaca agggcaccta cctgtacaac gactgccccg acccggcct ggacaccgat   240 tgcagagagt gcgagaacgg caccttcacc gccagcgaga accacctgag acagtgcctg   300
tcctgcagca agtgcagaaa agagatgaac caggtcgaga tcagcccctg caccgtgtac   360
cgggacaccg tgtgcggctg ccggaagaac cagtacagat ctattggag cgagacactg   420 ttccagtgca caactgcag cctgtgcctg aatggcaccg tgcagatcag ctgccaggaa   480
aagcagaaca ccatctgcac ctgtcacgcc ggattctttc tgcgcgagca cgagtgcgtg   540
tcctgtgtga actgcaagaa aaacaccgag tgtggcaagc tgtgcctgcc cctgtggaa   600 accgtgaaag tgcctcagga ccctggcagc acattcaacg agtgccggtg taccgacacc   660 ccccttgtc ctgtgcctga gctctgggc ggaccctccg tgctgatctt ccacccaag    720 cccaaggaca tcctgcggat cacccggacc cccgaagtga cctgcgtggt gctggatctg   780
ggccgcgagg accctgaggt gcagatcagt tggttcgtgg acggcaaaga ggtgcacacc   840
gctaagaccc agagcagaga gcagcagttc aacggcacct acagagtggt gtccgtgctg   900
cccatcgagc accaggactg gctgaccggc aaagagttca gtgcagagt caaccacatc   960 ggcctgccta gccctatcga gcggaccatc agcaaggcca gggcagagc ccacaagccc  1020 agcgtgtacg tgctccccacc cagccccaaa gagctgagca gcagcgacac cgtgtccatc  1080
acctgtctga tcaaggactt ctaccccccg acatcgacg tggaatggca gagcaacgga  1140
cagcaggaac ccgagcggaa gcacagaatg accccccac agctggacga ggacggcagc  1200
tacttcctgt acagcaagct gagcgtggac aagagccggt ggcagcaggg cgacccttc  1260 acatgtgccg tgatgcacga gacactgcag aaccactaca ccgacctgtc tctgagccac  1320
```

```
agccccggca agtga                                              1335
```

<210> SEQ ID NO 29
<211> LENGTH: 1347
<212> TYPE: DNA
<213> ORGANISM: Artificial Sequence
<220> FEATURE:
<223> OTHER INFORMATION: caTNFRp60-HCB - nucleotide sequence encoding
      SEQ ID NO:7

<400> SEQUENCE: 29

```
atgggcctgc ccaccgtgcc tggactgctg ctgcctctgg tgctgctggc cctgctgctg     60
gaaatctacc ccatcagcgt gaccgccctg gtgccccacc cccggaacag agtgaagcgg    120
gccatcctgt gtccacaggg caagtacatc cccctcagg acgacagcat ctgctgcacc     180
aagtgccaca agggcaccta cctgtacaac gactgccccg acccggcct ggacaccgat     240
tgcagagagt gcgagaacgg caccttcacc gccagcgaga accacctgag acagtgcctg    300
tcctgcagca agtgcagaaa agagatgaac caggtcgaga tctctccctg caccgtgtac    360
cgggacaccg tgtgcggctg ccggaagaac cagtacagat tctattggag cgagacactg    420
ttccagtgca caactgcag cctgtgcctg aatggcaccg tgcagatcag ctgccaggaa    480
aagcagaaca ccatctgcac ctgtcacgcc ggattctttc tgcgcgagca cgagtgcgtg    540
tcctgtgtga actgcaagaa aaacaccgag tgtggcaagc tgtgcctgcc ccctgtggaa    600
accgtgaaag tgcctcagga ccccggcagc acacccaagc gcgagaacgg cagagtgccc    660
agaccccccg actgccctaa gtgtcccgcc cctgagatgc tgggcggacc ctccgtgttc    720
atcttcccac ccaagcccaa ggacaccctg ctgatcgccc ggacccccga agtgacctgc    780
gtggtggtgg acctggaccc cgaggaccct gaggtgcaga tcagttggtt cgtggacggc    840
aagcagatgc agaccgccaa gacccagccc agagaggaac agttcaacgg cacctaccgg    900
gtggtgtccg tcctgcctat cggccaccag gactggctga aggcaagca gtttacctgc    960
aaagtgaaca caaaggccct gcctagcccc atcgagcgga ccatcagcaa ggccagaggc   1020
caggcccacc agcccagcgt gtacgtgctg cccccagcc gggaagaact gagcaagaat   1080
accgtgtccc tgacctgcct gatcaaggac ttctacccc ccgacatcga cgtggaatgg   1140
cagagcaacg gccagcagga acccgagagc aagtaccgga ccaccccccc acagctggac   1200
gaggacggca gctacttcct gtacagcaag ctgagcgtgg acaagagccg gtggcagcgg   1260
ggcgacacct tcatctgcgc cgtgatgcac gaggccctgc acaaccacta cacccaggaa   1320
agcctgtctc acagccccgg caagtga                                       1347
```

<210> SEQ ID NO 30
<211> LENGTH: 1341
<212> TYPE: DNA
<213> ORGANISM: Artificial Sequence
<220> FEATURE:
<223> OTHER INFORMATION: caTNFRp60-HCC - nucleotide sequence encoding
      SEQ ID NO:8

<400> SEQUENCE: 30

```
atgggcctgc ccaccgtgcc tggactgctg ctgcctctgg tgctgctggc cctgctgctg     60
gaaatctacc ccatcagcgt gaccgccctg gtgccccacc cccggaacag agtgaagcgg    120
gccatcctgt gtccacaggg caagtacatc cccctcagg acgacagcat ctgctgcacc     180
aagtgccaca agggcaccta cctgtacaac gactgccccg acccggcct ggacaccgat     240
```

| | |
|---|---|
| tgcagagagt gcgagaacgg caccttcacc gccagcgaga accacctgag acagtgcctg | 300 |
| tcctgcagca agtgcagaaa agagatgaac caggtcgaga tcagcccctg caccgtgtac | 360 |
| cgggacaccg tgtgcggctg ccggaagaac cagtacagat tctattggag cgagacactg | 420 |
| ttccagtgca caactgcag cctgtgcctg aatggcaccg tgcagatcag ctgccaggaa | 480 |
| aagcagaaca ccatctgcac ctgtcacgcc ggattctttc tgcgcgagca cgagtgcgtg | 540 |
| tcctgtgtga actgcaagaa aaacaccgag tgtggcaagc tgtgcctgcc ccctgtggaa | 600 |
| accgtgaaag tgcctcagga ccccggcagc acagctaaag aatgcgagtg caagtgcaac | 660 |
| tgcaacaact gccctgtcc tggctgcgga ctgctgggag acctagcgt gttcatcttc | 720 |
| ccacccaagc ccaaggacat cctggtcacc gcccggaccc ccaccgtgac atgcgtggtg | 780 |
| gtggacctgg accccgagaa ccccgaggtg cagatcagtt ggttcgtgga cagcaaacag | 840 |
| gtgcagaccg ccaacaccca gcccagagag gaacagagca cggcaccta cagagtggtg | 900 |
| tctgtgctgc ctatcggcca ccaggactgg ctgagcggca agcagttcaa gtgcaaagtg | 960 |
| aacaacaagg ccctgcctag ccccatcgag gaaatcatca gcaagacccc tggacaggcc | 1020 |
| caccagccta acgtgtacgt cctgcctccc agccgggacg agatgtccaa gaacaccgtg | 1080 |
| accctgactt gcctggtcaa ggacttcttc cccccgaaa tcgacgtgga atggcagtcc | 1140 |
| aacggccagc aggaacccga gagcaagtac cggatgaccc cccacagct ggacgaggac | 1200 |
| ggcagctact tcctgtacag caagctgagc gtggacaaga gccggtggca gcggggcgac | 1260 |
| accttcatct gcgccgtgat gcacgaggcc ctgcacaacc actacaccca gatcagcctg | 1320 |
| agccacagcc ccggcaagtg a | 1341 |

<210> SEQ ID NO 31
<211> LENGTH: 1335
<212> TYPE: DNA
<213> ORGANISM: Artificial Sequence
<220> FEATURE:
<223> OTHER INFORMATION: caTNFRp60-HCD - nucleotide sequence encoding
      SEQ ID NO:9

<400> SEQUENCE: 31

| | |
|---|---|
| atgggcctgc ccaccgtgcc tggactgctg ctgcctctgg tgctgctggc cctgctgctg | 60 |
| gaaatctacc ccatcagcgt gaccgccctg gtgccccacc ccggaacag agtgaagcgg | 120 |
| gccatcctgt gtccacaggg caagtacatc cacccctcagg acgacagcat ctgctgcacc | 180 |
| aagtgcccaca agggcaccta cctgtacaac gactgccccg acccggcct ggacaccgat | 240 |
| tgcagagagt gcgagaacgg caccttcacc gccagcgaga accacctgag acagtgcctg | 300 |
| tcctgcagca agtgcagaaa agagatgaac caggtcgaga tcagcccttg caccgtgtac | 360 |
| cgggacaccg tgtgcggctg ccggaagaac cagtacagat tctattggag cgagacactg | 420 |
| ttccagtgca caactgcag cctgtgcctg aatggcaccg tgcagatcag ctgccaggaa | 480 |
| aagcagaaca ccatctgcac ctgtcacgcc ggattctttc tgcgcgagca cgagtgcgtg | 540 |
| tcctgtgtga actgcaagaa aaacaccgag tgtggcaagc tgtgcctgcc ccctgtggaa | 600 |
| accgtgaaag tgccccagga ccccggcagc acagcccaaag aaagcacatg caagtgcatc | 660 |
| agcccctgtc cgtgcctga gtctctggga ggccttccg tgttcatctt ccacccaag | 720 |
| cccaaggaca tcctgcgat caccccggacc cccgagatca cctgtgtggt gctggacctg | 780 |
| ggccgcgagg accctgaggt gcagatcagt tggttcgtgg acggcaaaga ggtgcacacc | 840 |
| gctaagaccc agcccagaga gcagcagttc aacagcacct accgggtggt gtccgtcctg | 900 |

-continued

```
cccatcgagc accaggactg gctgaccggc aaagagttca agtgcagagt caaccacatc    960
ggcctgccca gccctatcga gcggaccatc agcaaggcca gaggccaggc ccaccagccc   1020
agcgtgtacg tgctgccacc tagccccaaa gagctgagca gcagcgacac cgtgaccctg   1080
acctgcctga tcaaggactt ctaccccccc gaaatcgacg tggaatggca gagcaacgga   1140
cagcctgagc ccgagagcaa gtaccacacc acagccccc agctggacga ggacggcagc   1200
tacttcctgt acagcaagct gagcgtggac aagagccggt ggcagcaggg cgacaccttc   1260
acatgtgccg tgatgcacga ggccctgcag aaccactaca ccgacctgag cctgagccac   1320
agccccggca agtga                                                    1335
```

TUMOUR NECROSIS FACTOR RECEPTOR FUSION PROTEINS AND METHODS OF USING THE SAME

FIELD OF THE INVENTION

The present invention relates to chimeric fusion polypeptides comprising the extracellular ligand binding portion of canine tumour necrosis factor receptor polypeptides and canine immunoglobulin Fc domain polypeptides which are conjoined to form dimeric fusion proteins. The invention further extends to polynucleotides encoding the same, to methods of production of the chimeric fusion polypeptides and further to their use in the treatment and prevention of inflammatory diseases, in particular TNF-associated disorders.

BACKGROUND TO THE INVENTION

Tumour necrosis factor alpha (TNF-α) and tumour necrosis factor beta (TNF-β) exhibit a significant overlap in function. This homology has resulted in these cytokines being collectively referred to as tumour necrosis factor (TNF). TNF exhibits a powerful pleiotropic role in mediating the proinflammatory immune response and has also been shown to have involvement in control of cell proliferation, differentiation and apoptosis. TNF mediates these effects by binding to the type I and II TNF receptors (TNFR), which are cell surface receptors that are expressed on TNF responsive cells.

The use of TNF antagonists, such as anti-TNF antibodies, soluble TNF receptor proteins and TNF receptor-Fc fusion proteins has shown that the proinflammatory effects mediated by TNF, such as induction of the expression of proinflammatory cytokine expression (IL-1, IL-8) and tissue destruction, can be reversed. Furthermore, the use of recombinant TNFR-Fc fusion proteins such as ENBREL (Etanercept, Immunex) has shown that TNF antagonism can be used to treat TNF-associated conditions, in particular rheumatoid arthritis.

Accordingly, the inhibition of TNF using tumour necrosis factor receptor (TNFR)-immunoglobulin Fc domain fusion proteins or anti-TNF neutralising monoclonal antibodies has been proven to be a successful therapeutic approach for the treatment of a variety of human inflammatory diseases, including rheumatoid arthritis and psoriatic arthritis.

Companion animals, such as dogs, develop inflammatory diseases similar to those which occur in humans, with examples being rheumatoid arthritis (RA), osteoarthritis, immune-mediated polyarthritidies, plasmatic-lymphocytic synovitis, systemic lupus erythematosis (SLE), vasculitis and a variety of autoimmune skin diseases. It is estimated that one in five adult dogs in the USA has arthritis and dogs have been used as models of human joint disease, e.g. for osteoarthritis, anterior cruciate ligament disruption and meniscal damage.

The role of TNF in the occurrence of inflammation in dogs has been extensively documented. For example, it has been observed that there is increased secretion of TNF alpha in cell infiltrates of synovial fluid of dogs presenting with stifle arthritis TNF and the type II TNF receptor has been shown to be significantly elevated in the central and peripheral retina of dogs with glaucoma as part of a broad inflammatory response. Treatment of dogs with the human TNFR-Fc fusion protein Etanercept ((huTNFR-Fc) Immunex, a TNF antagonist) reduced myocardial injury by approximately 25-40% following ischaemia-reperfusion induced by balloon occlusion in a closed chest model of human heart disease, with a concomitant reduction in associated inflammatory markers such as ICAM-1 and NF-kB. Similarly, a 60% reduction in infarct size in an open chest dog model of ischaemia reperfusion using 2 mg/kg TNFR-Fc has also been demonstrated. However, the use of huTNFR-Fc as a therapeutic agent for the treatment of diseases of the dog is not indicated beyond this modelling of human disease due to the immunogenicity of human proteins when injected into dogs. Furthermore, the IgG Fc domain of Etanercept is complement recruiting and hence undesirable in the context of an inflammatory disease, due to the immune response which is mediated.

Anti-canine TNF monoclonal antibodies have been used to detect low levels of TNF by capture ELISA in supernatants of canine PBMCs treated with lipopolysaccharide (LPS) and TNF alpha expression has also been reported in skin samples of canine hemangiopericytoma, tricoblastoma, lipoma and mastocytoma. TNF-alpha and TNF receptors are present in canine articular cartilage in an induced model of osteoarthritis, while Adalimumab, a humanised monoclonal antibody to TNF, has been tested in two dogs with exfoliative cutaneous lupus erythematosus (ECLE) (0.5 mg/kg every 2 weeks for 8 weeks), but disease progression was shown to be unaltered, with serum TNF-alpha levels remaining unchanged. Immunogenicity to Adalimumab would potentially have caused the lack of efficacy in these repeat dosing studies. In particular, neutralising antibodies which may be raised against Adalimumab would prevent repeat dosing and therefore restrict the longer term effectiveness of such a therapeutic approach.

Accordingly, due to the involvement of TNF in a wide range of inflammatory mediated conditions in canines, there is a need for inhibitors of canine TNF that can be used for the long-term inhibition of TNF in order to treat TNF-associated disorders and inflammatory conditions in dogs.

SUMMARY OF THE INVENTION

According to a first aspect of the present invention there is provided a chimeric fusion polypeptide comprising, consisting or consisting essentially of an extracellular domain of a canine TNF receptor polypeptide, or a TNF binding fragment thereof, conjoined to a polypeptide comprising, consisting or consisting essentially of an Fc region of a canine IgG immunoglobulin heavy chain, or a fragment thereof wherein the fragment comprises at least the CH2 and CH3 constant domains.

Typically the chimeric fusion polypeptide specifically binds to canine TNF. Typically the chimeric fusion polypeptide neutralises the biological activity of canine TNF. In certain embodiments TNF refers to TNF-α and/or TNF-β. The chimeric fusion protein exhibits improved stability and in vivo half life. Furthermore, the chimeric fusion polypeptide overcomes problems associated with administering hitherto known anti-TNF compounds to canines, most specifically by limiting the production of neutralising antibodies, in particular xenoantibodies, thereagainst, when administered to a canine.

Typically the extracellular domain of the canine TNF receptor polypeptide comprises, consists of or consists essentially of a truncated form of the canine tumour necrosis factor receptor which lacks both the transmembrane domain and the cytoplasmic domain. Typically the extracellular domain or fragment thereof comprises a ligand binding portion of the canine TNF receptor polypeptide and binds to TNF. In certain embodiments the chimeric fusion polypeptide comprises a signal sequence joined to the extracellular domain of the canine TNF receptor polypeptide. Typically the extracellular domain or fragment thereof antagonises the biological activity of canine TNF.

In certain embodiments the canine TNF receptor polypeptide is the canine TNF receptor polypeptide p60 (caTNFR p60). In certain embodiments the extracellular domain therefore comprises, consists of or consists essentially of the extracellular domain of the p60 soluble form of the canine TNF receptor. In certain embodiments the extracellular domain includes a signal sequence joined to the extracellular domain. In certain embodiments a fragment of the caTNFR p60 peptide may be used, in particular a TNF binding portion of the extracellular domain. In certain embodiments the canine TNF receptor polypeptide comprises, consists of or consists essentially of the amino acid of SEQ ID NO:1 (as encoded by SEQ ID NO:23), or a sequence having at least 80%, 85%, 90%, 93%, 95%, 96%, 97%, 98% or 99% sequence identity thereto wherein said sequence binds to canine TNF. Typically said sequence antagonises the biological activity of canine TNF.

In certain further embodiments the canine TNF receptor polypeptide is the canine TNF receptor polypeptide p80 (caTNFR p80). In certain embodiments the extracellular domain therefore comprises, consists of or consists essentially of the extracellular domain of caTNFR p80. In certain embodiments the extracellular domain includes a signal sequence joined to the extracellular domain. In certain embodiments a fragment of the caTNFR p80 peptide may be used, in particular a TNF binding portion of the extracellular domain. In certain embodiments the canine TNF receptor polypeptide comprises, consists of or consists essentially of the amino acid of SEQ ID NO:14 or a sequence having at least 80%, 85%, 90%, 93%, 95%, 96%, 97%, 98% or 99% sequence identity thereto wherein said sequence binds to canine TNF. Typically said sequence antagonises the biological activity of canine TNF.

Typically the fragment of the extracellular domain of the canine TNF receptor polypeptide specifically binds to canine TNF. Typically the fragment antagonises the biological activity of canine TNF.

Typically the polypeptide comprising, consisting or consisting essentially of an Fc region of a canine IgG immunoglobulin heavy chain or the fragment thereof comprises, consists of or consists essentially of at least the CH2 and CH3 constant domains of the canine IgG immunoglobulin heavy chain. In certain embodiments a hinge region, or a fragment thereof is also provided. In certain embodiments the Fc region derived from a canine IgG immunoglobulin heavy chain is of IgG subtype A (e.g. caHCA, SEQ ID NO:2), IgG subtype B (e.g. caHCB, SEQ ID NO:3), IgG subtype C (e.g. caHCC, SEQ ID NO:4) or IgG subtype D (e.g. caHCD, SEQ ID NO:5), or a fragment thereof. In certain embodiments the Fc region comprises, consists of or consists essentially of an amino acid sequence selected from the group consisting of SEQ ID NO:2 (as encoded by SEQ ID NO:24), SEQ ID NO:3 (as encoded by SEQ ID NO:25), SEQ ID NO:4 (as encoded by SEQ ID NO:26), SEQ ID NO:5 (as encoded by SEQ ID NO:27) and a sequence having at least 90, 95, 96, 97, 98 or 99% sequence homology to any of the foregoing, or a fragment thereof. Typically the Fc region or fragment thereof or the sequence having homology thereto provides the canine TNF receptor polypeptide with improved stability and an improved in vivo half life.

The extracellular domain of the canine TNF receptor polypeptide, or fragment thereof, may be conjoined to the polypeptide comprising the Fc region of a canine IgG immunoglobulin heavy chain, or fragment thereof, by way of a covalent linkage. In certain embodiments a linker, such as a polypeptide linker, may be used to covalently link the canine TNFR extracellular domain polypeptide and the canine Fc domain polypeptide, or fragments thereof, to form a chimeric fusion polypeptide, which may also be known as a fusion protein or an immunoconjugate. While a linker region is not typically required due to the structural flexibility conferred by the hinge domain of the Fc domain of the canine derived immunoglobulin component, if a linker is used, this linker may contain at least one cleavage site. Accordingly, in certain embodiments the chimeric fusion polypeptide further comprises a linker peptide functionally interposed between the canine TNF receptor polypeptide and the canine IgG Fc domain polypeptide.

In certain embodiments the chimeric fusion polypeptide comprises, consists of or consists essentially of an amino acid sequence selected from the group consisting of SEQ ID NO: 6 (as encoded by SEQ ID NO:28), SEQ ID NO:7 (as encoded by SEQ ID NO:29), SEQ ID NO:8 (as encoded by SEQ ID NO:30), SEQ ID NO:9 (as encoded by SEQ ID NO:31) and a sequence having at least 90, 95, 96, 97, 98 or 99% sequence homology to any of the foregoing, wherein said homologous sequence binds to canine TNF. Typically said homologous sequence antagonises the biological activity of canine TNF.

In certain embodiments the chimeric fusion polypeptide comprises, consists of or consists essentially of an amino acid sequence selected from the group consisting of SEQ ID NO: 10, SEQ ID NO:11, SEQ ID NO:12, SEQ ID NO:13 and a sequence having at least 90, 95, 96, 97, 98 or 99% sequence homology to any of the foregoing, wherein said homologous sequence binds to canine TNF. Typically said homologous sequence antagonises the biological activity of canine TNF.

In certain embodiments the chimeric fusion polypeptide comprises, consists of or consists essentially of an amino acid sequence selected from the group consisting of SEQ ID NO: 15, SEQ ID NO:16, SEQ ID NO:17, SEQ ID NO:18 and a sequence having at least 90, 95, 96, 97, 98 or 99% sequence homology to any of the foregoing, wherein said homologous sequence binds to canine TNF. Typically said homologous sequence antagonises the biological activity of canine TNF.

In certain embodiments the chimeric fusion polypeptide comprises, consists of or consists essentially of an amino acid sequence selected from the group consisting of SEQ ID NO: 19, SEQ ID NO:20, SEQ ID NO:21, SEQ ID NO:22 and a sequence having at least 90, 95, 96, 97, 98 or 99% sequence homology to any of the foregoing, wherein said homologous sequence binds to canine TNF. Typically said homologous sequence antagonises the biological activity of canine TNF.

In certain further embodiments the chimeric fusion polypeptide of the invention specifically binds to canine TNF-alpha (tumour necrosis factor alpha) with a binding affinity having an equilibrium-dissociation constant ($K_D$) of $1\times10^{-8}$ or less. Furthermore, it is preferred that xenoantibodies (also referred to as neutralising antibodies) are not generated against the chimeric fusion polypeptides of the invention following administration to a canine subject. Furthermore, it is preferred that the Fc domain portion of the chimeric fusion polypeptides does not mediate any downstream effector functions including, but not limited to, complement recruitment, fixation and activation, ADCC and Fc receptor binding and activation. Mutations, substitutions and additions may be made to the amino acid sequence of the canine IgG Fc domain polypeptide to ensure that Fc receptor mediated downstream effector functions do not occur. Furthermore, canine IgG Fc domain polypeptides derived from specific subtypes of canine IgG heavy chains may be selected on the base of their desirable properties in not mediating downstream effector functions.

In certain embodiments modifications to the amino acid sequence of the amino acid residues of the Fc domains of the chimeric fusion polypeptide of the invention may be made. Said modifications may involve the addition, substitution or deletion of one or more amino acid residues. Said amino acid changes are typically performed in order to modify the functional characteristics of the antibody. For example, amino acid modifications may be performed to prevent downstream effector functions mediated by the Fc domain component of the chimeric fusion polypeptide, for example, by preventing the ability of the Fc domain component to bind to Fc receptors, activate complement or induce ADCC. Furthermore, modifications may be made to the amino acid residues of the Fc domain residues in order to modify the circulatory half life of the chimeric fusion polypeptide.

The invention further extends to an isolated polypeptide comprising, consisting of or consisting essentially of SEQ ID NO:1 or SEQ ID NO:14 or a sequence having at least 90, 95, 96, 97, 98 or 99% sequence homology thereto, and to use of same in the methods of the invention as described below. Typically said homologous sequence binds to canine TNF. Typically said homologous sequence antagonises the biological activity of canine TNF. The invention further extends to the use of SEQ ID NO:14 as the extracellular domain of the canine TNF receptor polypeptide p80.

In various further aspects the present invention extends to a polynucleotide which encodes a chimeric fusion polypeptide of the invention. In various further aspects the invention extends to the expression in a canine of a polynucleotide encoding a chimeric fusion polypeptide of the invention.

Accordingly, a further aspect of the present invention provides a polynucleotide which encodes a chimeric fusion polypeptide comprising the extracellular domain of a canine TNF receptor polypeptide, or a fragment thereof, conjoined to a polypeptide comprising the Fc region of a canine IgG immunoglobulin heavy chain, or a fragment thereof. In certain embodiments the polynucleotide comprises a sequence selected from the group consisting of SEQ ID NO:28, SEQ ID NO:29, SEQ ID NO:30, SEQ ID NO:31 and a sequence having at least 90, 95, 96, 97, 98 or 99% sequence homology to any of the foregoing, wherein said homologous sequence encodes a polypeptide which binds to canine TNF. Typically said polypeptide antagonises the biological activity of canine TNF.

In certain embodiments the polynucleotide encodes a chimeric polypeptide comprising the amino acid sequence selected from the group consisting of SEQ ID NO:6, SEQ ID NO:7, SEQ ID NO:8, SEQ ID NO:9, SEQ ID NO: 10, SEQ ID NO:11, SEQ ID NO:12, SEQ ID NO:13 and a sequence having at least 90, 95, 96, 97, 98 or 99% sequence homology to any of the foregoing, wherein said homologous sequence binds to canine TNF. Typically said homologous sequence antagonises the biological activity of canine TNF.

In certain embodiments the polynucleotide encodes a chimeric polypeptide comprising the amino acid sequence selected from the group consisting of SEQ ID NO:15, SEQ ID NO:16, SEQ ID NO:17, SEQ ID NO:18, SEQ ID NO: 19, SEQ ID NO:20, SEQ ID NO:21, SEQ ID NO:22 and a sequence having at least 90, 95, 96, 97, 98 or 99% sequence homology to any of the foregoing, wherein said homologous sequence binds to TNF. Typically said homologous sequence antagonises the biological activity of canine TNF.

A further aspect of the invention provides a recombinant vector which comprises a polynucleotide which encodes a chimeric fusion polypeptide comprising the amino acid sequence selected from the group consisting of SEQ ID NO:6, SEQ ID NO:7, SEQ ID NO:8, SEQ ID NO:9, SEQ ID NO: 10, SEQ ID NO:11, SEQ ID NO:12, SEQ ID NO:13, SEQ ID NO: 15, SEQ ID NO:16, SEQ ID NO:17, SEQ ID NO:18, SEQ ID NO: 19, SEQ ID NO:20, SEQ ID NO:21, SEQ ID NO:22 and a sequence having at least 90, 95, 96, 97, 98 or 99% sequence homology to any of the forgoing, wherein said homologous sequence binds to TNF. Typically said homologous sequence antagonises the biological activity of canine TNF. In certain embodiments the vector is positioned adjacent to and under the control of, or is operably linked to, an expression promoter.

Also provided is an isolated polynucleotide which encodes the extracellular domain of a canine TNF receptor polypeptide. In certain embodiments the polynucleotide encodes a canine TNF receptor (caTNFR) polypeptide comprising the amino acid sequence of SEQ ID NO:1 or a sequence having at least 90, 95, 96, 97, 98 or 99% sequence homology thereto, wherein said homologous sequence binds to TNF. Typically said homologous sequence antagonises the biological activity of canine TNF. In certain embodiments the polynucleotide encodes a canine TNF receptor (caTNFR) polypeptide comprising the amino acid sequence of SEQ ID NO:14 or a sequence having at least 90, 95, 96, 97, 98 or 99% sequence homology thereto, wherein said homologous sequence binds to TNF. Typically said homologous sequence antagonises the biological activity of canine TNF. In certain embodiments the polynucleotide comprises SEQ ID NO:23 or a sequence having at least 90, 95, 96, 97, 98 or 99% sequence homology thereto, wherein said homologous sequence encodes a polypeptide which binds to TNF. Typically said polypeptide antagonises the biological activity of canine TNF. SEQ ID NO:23 is the nucleotide sequence encoding for the amino acid sequence of SEQ ID NO:1. The invention further extends to a recombinant vector which comprises one of the polynucleotides described herein.

In various further aspects the present invention extends to the use of the chimeric fusion polypeptide, or the polynucleotide encoding the same, in methods for the treatment and/or prevention of canine conditions mediated by TNF expression. The chimeric fusion polypeptide, vector or polynucleotide used in the methods of the invention may be any of the chimeric fusion polypeptides, vectors or polynucleotides described above.

Accordingly, a yet further aspect of the present invention provides a method for preventing, reducing or ameliorating an undesired inflammatory response in a canine in need thereof, the method comprising the steps of:
  providing a chimeric fusion polypeptide having the amino acid sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 15, SEQ ID NO:16, SEQ ID NO:17, SEQ ID NO:18, SEQ ID NO: 19, SEQ ID NO:20, SEQ ID NO:21 and SEQ ID NO:22 or a polypeptide sequence having at least 90, 95, 96, 97, 98 or 99% sequence homology thereto, or a vector comprising a polynucleotide which encodes the same, and administering the same to the canine in a therapeutically effective amount which is sufficient to prevent, reduce or ameliorate the inflammatory response.

In certain embodiments the homologous sequence binds to TNF. Typically said homologous sequence antagonises the biological activity of canine TNF.

In certain embodiments the method further comprises the step of administering at least one further TNF antagonist or anti-inflammatory compound along with the chimeric fusion polypeptide.

A yet further aspect of the present invention provides a method for reducing tumour necrosis factor (TNF) levels in a canine in need thereof, said method comprising the steps of:

providing a chimeric fusion polypeptide having the amino acid sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 15, SEQ ID NO:16, SEQ ID NO:17, SEQ ID NO:18, SEQ ID NO: 19, SEQ ID NO:20, SEQ ID NO:21 and SEQ ID NO:22 or a polypeptide sequence having at least 90, 95, 96, 97, 98 or 99% sequence homology thereto, or a vector comprising a polynucleotide which encodes the same, and administering the same to the canine in a therapeutically effective amount which is sufficient to reduce tumour necrosis factor levels.

In certain embodiments the homologous sequence binds to TNF. Typically said homologous sequence antagonises the biological activity of canine TNF.

In certain embodiments the method further comprises the step of administering at least one further TNF antagonist or anti-inflammatory compound.

A yet further aspect of the present invention provides a method for treating or ameliorating a tumour necrosis factor (TNF) related condition in a canine in need thereof, said method comprising the steps of:

providing a chimeric fusion polypeptide having the amino acid sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 15, SEQ ID NO:16, SEQ ID NO:17, SEQ ID NO:18, SEQ ID NO: 19, SEQ ID NO:20, SEQ ID NO:21 and SEQ ID NO:22 or a polypeptide sequence having at least 90, 95, 96, 97, 98 or 99% sequence homology thereto, or a vector comprising a polynucleotide which encodes the same, and administering the same to the canine in a therapeutically effective amount which is sufficient to treat or ameliorate the condition.

In certain embodiments the homologous sequence binds to TNF. Typically said homologous sequence antagonises the biological activity of canine TNF.

In certain embodiments the method further comprises the step of administering at least one further TNF antagonist or anti-inflammatory compound.

In certain embodiments the undesired inflammatory response or TNF related condition is a chronic inflammatory disease. Said chronic inflammatory disease may be selected from the group consisting of, but not limited to, rheumatoid arthritis (RA), osteoarthritis and other polyarthritidies, ankylosing spondylitis (AS), Crohn's disease and ulcerative colitis, psoriasis and psoriatic arthritis (PsA), systemic vasculitis, atopic dermatitis, congestive heart failure (CHF), refractory uveitis, bronchial asthma and allergic conditions. Inflammatory mediated conditions may also include sepsis and shock, diabetes mellitus and neuro-degenerative conditions such as Alzheimer's disease, Parkinson's disease, stroke and amyotrophic lateral sclerosis.

In certain further embodiments the undesired inflammatory response or TNF related condition, which may also be referred to as a TNF-alpha related disorder, or a disorder in which TNF-alpha is a key inflammatory mediator, may include, but is not limited to, Behcet's disease, bullous dermatitis, neutrophilic dermatitis, toxic epidermal necrolysis, systemic vasculitis, pyoderma gangrenosum, pustular dermatitis, cerebral malaria, hemolytic uremic syndrome, pre-eclampsia, allograft rejection, otitis media, snakebite, erythema nodosum, myelodysplastic syndromes, graft versus host disease, dermatomyositis and polymyositis.

According to a yet further aspect of the present invention there is provided a method for the treatment of arthritis or an arthritic condition in a canine in need thereof, said method comprising the steps of:

providing a chimeric fusion polypeptide having the amino acid sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 15, SEQ ID NO:16, SEQ ID NO:17, SEQ ID NO:18, SEQ ID NO: 19, SEQ ID NO:20, SEQ ID NO:21 and SEQ ID NO:22 or a polypeptide sequence having at least 90, 95, 96, 97, 98 or 99% sequence homology thereto, or a vector comprising a polynucleotide which encodes the same, and administering a therapeutically effective amount to the canine.

In certain embodiments the homologous sequence binds to TNF. Typically said homologous sequence antagonises the biological activity of canine TNF.

In certain embodiments the arthritis or arthritic condition includes the conditions selected from the group consisting of immune mediated polyarthritis, rheumatoid arthritis, osteoarthritis, psoriatic arthritis, juvenile idiopathic arthritis, ankylosing spondylitis and related conditions.

Typically, the treatment of the arthritis or arthritic condition comprises ameliorating, inhibiting, reducing or suppressing the immune response which is causative, associated with, or attributable to the arthritic condition.

A further aspect of the present invention provides a method for the treatment of a condition caused by, associated with or resulting in increased expression of canine TNF or increased sensitivity to TNF in a canine subject, said method comprising the steps of:

providing a chimeric fusion polypeptide having the amino acid sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 15, SEQ ID NO:16, SEQ ID NO:17, SEQ ID NO:18, SEQ ID NO: 19, SEQ ID NO:20, SEQ ID NO:21 and SEQ ID NO:22 or a polypeptide sequence having at least 90, 95, 96, 97, 98 or 99% sequence homology thereto, or a vector comprising a polynucleotide which encodes the same, and administering a therapeutically effective amount to a canine in need of said treatment.

In certain embodiments the homologous sequence binds to TNF. Typically said homologous sequence antagonises the biological activity of canine TNF.

In certain embodiments the foregoing methods of the invention further comprise the further step of co-administering at least one further agent which may enhance and/or supplement the effectiveness of the chimeric fusion polypeptide of the invention. For example, the chimeric fusion polypeptide may be co-administered along with one or more additional pharmaceutical compositions. Said additional compositions may comprise a drug useful for treating a chronic inflammatory condition, in particular, a TNF-alpha related disorder. In certain embodiments the additional pharmaceutical composition may be a TNF antagonist, such as methotrexate, a chimeric or caninised antibody to canine TNF, an anti-canine TNF antibody fragment, at least one analgesic, a compound which is a cytokine suppressing anti-inflammatory drug, an NSAID, an opioid, a corticosteroid, a steroid or an antagonist of nerve growth factor.

Examples of suitable analgesics include, but are not limited to, butorphanol, buprenorphine, fentanyl, flunixin meglumine, merpidine, morphine, nalbuphine and derivatives thereof. Suitable NSAIDS include, but are not limited to, acetaminophen, acetylsalicylic acid, carprofen, etodolac, ketoprofen, meloxicam, firocoxib, rob enacoxib, deracoxib and the like.

In certain further embodiments the at least one further agent or pharmaceutical composition may be a therapeutically active agent that may be one or more of the group selected from an antibiotic, an antifungal agent, an antiprotozoal agent, an antiviral agent and similar therapeutic agents. Furthermore the at least one further agent may be an inhibitor of mediator(s) of inflammation, such as a PGE-receptor antagonist, an immunosuppressive agent, such as cyclosporine, or anti-inflammatory glucocorticoids. In certain further embodiments the at least one further agent may be an agent which is used for the treatment of cognitive dysfunction or impairment, such as memory loss or related conditions which may become increasingly prevalent in older canines. Further still, the at least one further agent may be an anti-hypertensive or other compound used for the treatment of cardiovascular dysfunction, for example, to treat hypertension, myocardial ischemia, congestive heart failure and the like. Further still, the at least one further agent may be a diuretic, vasodilator, beta-adrenergic receptor antagonist, angiotensin-II converting enzyme inhibitor, calcium channel blocker or HMG-CoA reductase inhibitor.

In certain embodiments the chimeric fusion protein or antigen binding fragment is administered to the canine as part of the foregoing methods at a dose ranging from about 0.01 mg/kg of body weight to about 10 mg/kg of body weight, in particular, from 0.03 mg/kg of body weight to about 3 mg/kg of body weight.

A further aspect of the present invention provides a chimeric fusion polypeptide or polynucleotide as described above for use as a medicament, in particular, for use in the treatment or prevention of any of the conditions described above. The invention extends to use of the chimeric fusion polypeptide or polynucleotide as described above in the preparation of a medicament for the treatment or prevention of any of the conditions described above.

In various further aspects the present invention extends to a composition comprising a chimeric fusion polypeptide which binds canine TNF according to any foregoing aspect of the invention. The chimeric fusion polypeptide used in the compositions of the invention may be any of the chimeric fusion polypeptides described above. In certain embodiments, the composition further comprises at least one pharmaceutically acceptable carrier.

In a yet further aspect, the present invention provides a pharmaceutical composition comprising a chimeric fusion polypeptide having the amino acid sequence selected from the group consisting of SEQ ID NO:6, SEQ ID NO:7, SEQ ID NO:8, SEQ ID NO:9, SEQ ID NO: 10, SEQ ID NO:11, SEQ ID NO:12, SEQ ID NO:13, SEQ ID NO: 15, SEQ ID NO:16, SEQ ID NO:17, SEQ ID NO:18, SEQ ID NO: 19, SEQ ID NO:20, SEQ ID NO:21, SEQ ID NO:22 and a sequence having at least 90, 95, 96, 97, 98 or 99% sequence homology thereto, along with at least one carrier diluent or excipient.

In certain embodiments the homologous sequence binds to TNF. Typically said homologous sequence antagonises the biological activity of canine TNF.

In certain embodiments the pharmaceutical composition further comprises at least one further TNF antagonist compound and/or an anti-inflammatory compound. In certain embodiments the TNF antagonist compound is methotrexate.

In certain embodiments the pharmaceutical composition further comprises at least one analgesic, NSAID, opioid, corticosteroid, steroid or antagonist of nerve growth factor.

A yet further aspect of the present invention provides a method for producing a chimeric fusion polypeptide comprising the extracellular domain of a TNF receptor polypeptide which is functionally linked to the Fc domain of a canine IgG immunoglobulin, the method comprising:

(i) providing a recombinant host cell comprising a vector which can express a polynucleotide encoding the chimeric fusion polypeptide according to the invention;

(ii) culturing the host cell under conditions suitable for expression of the polypeptide, and (iii) recovering the chimeric fusion polypeptide.

In certain embodiments the host cell is a eukaryotic cell. In further embodiments the host cell is a prokaryotic cell. In certain embodiments the vector is the vector of the invention described above. In certain embodiments the polynucleotide is the polynucleotide of the invention described above.

According to a still further aspect of the present invention there is provided a chimeric fusion polypeptide according to any of the foregoing aspects of the invention, or a pharmaceutical composition according to the foregoing aspects of the invention, or a nucleic acid, or vector comprising the same according to any of the foregoing aspects of the invention for use in the treatment or prevention of an inflammatory mediated condition in a canine.

A yet further aspect of the invention provides a chimeric fusion polypeptide according to any of the foregoing aspects of the invention, or a pharmaceutical composition according to the foregoing aspects of the invention, or a nucleic acid, or vector comprising the same according to any of the foregoing aspects of the invention for use in the treatment of arthritis in a canine, in particular immune mediated polyarthritis, rheumatoid arthritis, osteoarthritis, psoriatic arthritis or ankylosing spondylitis.

A yet further aspect of the invention provides use of a chimeric fusion polypeptide according to any of the foregoing aspects of the invention, or a pharmaceutical composition according to the foregoing aspects of the invention, or a nucleic acid, or vector comprising the same according to any of the foregoing aspects of the invention in the preparation of a medicament for the treatment or prevention of a chronic inflammatory disease in a canine.

A yet further aspect of the invention provides use of a chimeric fusion polypeptide according to any of the foregoing aspects of the invention, or a pharmaceutical composition according to the foregoing aspects of the invention, or a nucleic acid, or vector comprising the same according to any of the foregoing aspects of the invention in the preparation of a medicament for the treatment, inhibition amelioration or prevention of rheumatoid arthritis or osteoarthritis in a canine.

In a yet further aspect there is provided a cell line, or a derivative or progeny cell thereof that produces a chimeric fusion polypeptide according to the invention.

A yet further aspect of the present invention provides a kit for the treatment of a chronic inflammatory condition in a canine or for the treatment of a condition associated with pain, or for the treatment, amelioration or inhibition of pain associated with osteoarthritis or rheumatoid arthritis, in a canine comprising a chimeric fusion polypeptide according to any of the foregoing aspects of the invention and instructions for use of the same.

In various further aspects the invention extends to a method for purification of certain of the chimeric fusion polypeptides of the invention. In particular, the inventors have surprisingly identified that chimeric fusion polypeptides which comprise canine derived immunoglobulin heavy chain domains of type B or C are purified more efficiently than those of type A or D. Accordingly, purification of chimeric fusion polypeptides of the invention provides higher yields where the immunoglobulin heavy chain domain is of type B or C. This is significant in that often protein purification based on Protein A matrices is used to obtain a commercially relevant yield of a protein for therapeutic use. Accordingly, the use of Protein A purification for the purification of chimeric fusion polypeptides of the invention provides higher yields where the immunoglobulin heavy chain domain is of type B or C, and, in particular, where the immunoglobulin heavy chain domains is of type B. This feature coupled to the entirely surprising observation that the resulting purified proteins do not recruit complement or mediate downstream effector functions when administered to a canine provides compositions according to the invention which can be advantageously administered to canines for therapeutic purposes and, in particular, protein therapeutics which are surprisingly advantageous over chimeric fusion polypeptides comprised of polypeptides of human origin.

A further aspect of the present invention therefore provides a method for purifying a chimeric fusion polypeptide of the invention, in particular chimeric fusion polypeptides having type B immunoglobulin heavy chains, comprising steps of purifying the chimeric fusion polypeptide using Protein A. In certain embodiments the eluting buffer has a pH of 5.

A further aspect of the present invention provides a method for purifying a chimeric fusion polypeptide of the invention, in particular chimeric fusion polypeptides having type C immunoglobulin heavy chains, comprising steps of purifying the chimeric fusion polypeptide using Protein G.

A yet further aspect of the present invention provides for the selective purification of a preferred dimer form of the chimeric fusion polypeptides of the invention, in particular chimeric fusion polypeptides having type B immunoglobulin heavy chains, from higher molecular weight multimers formed by CHO cell expression by elution at optimal pH from a Protein A column.

Accordingly, a further aspect of the present invention provides a method of purifying chimeric fusion polypeptides of the invention, in particular chimeric fusion polypeptides comprising type B immunoglobulin heavy chains, the method comprising the step of eluting the chimeric fusion polypeptides at a pH of greater than 4.7. Typically, the pH is 4.7 to 5.3, more typically 4.8 to 5.2, more typically 4.9 to 5.1 and most typically the pH is 5.0. Typically the chimeric fusion polypeptides are formed by CHO cell expression. Typically, the chimeric fusion polypeptides are eluted from Protein A, e.g. a Protein A column and the elution buffer has a pH of 5.

In certain embodiments the chimeric fusion polypeptide comprises SEQ ID NO:7, or a polypeptide sequence having at least 90, 95, 96, 97, 98 or 99%سequence homology thereto. In certain embodiments the chimeric fusion polypeptide comprises SEQ ID NO:11, or a polypeptide sequence having at least 90, 95, 96, 97, 98 or 99% sequence homology thereto. In certain embodiments the chimeric fusion polypeptide comprises SEQ ID NO:16, or a polypeptide sequence having at least 90, 95, 96, 97, 98 or 99% sequence homology thereto. In certain embodiments the chimeric fusion polypeptide comprises SEQ ID NO:20, or a polypeptide sequence having at least 90, 95, 96, 97, 98 or 99% sequence homology thereto.

The above method may be applied as a modification of the standard method of purification by Protein A chromatography to purify the desired TNFR-Fc fusion protein dimer from aggregated forms of same. This advantageously yields a product of higher specific activity and purity and, furthermore, the removal of aggregates reduces the potential for immunogenicity. The standard procedure for Protein A purification of immunoglobulins is to bind at neutral pH and elute at pH3.

In certain embodiments the method includes a step of eluting higher molecular weight multimers at a pH of 4.5-4.7.

Another aspect of the invention provides chimeric fusion polypeptides purified using the above described method of the invention and use of same as a medicament, for example, in the methods of treatment of the invention described above.

BRIEF DESCRIPTION OF THE FIGURES

FIG. 1 shows the amino acid sequence of the canine TNF Receptor (TNFR) p60 extracellular domain (ECD) fragment (SEQ ID NO:1).

FIG. 2 shows the amino acid sequence of the Fc domain of canine IgG1 immunoglobulin type A (caHCA) from the hinge region to C terminus (SEQ ID NO:2).

FIG. 3 shows the amino acid sequence of the Fc domain of canine IgG1 immunoglobulin type B (caHCB) from the hinge region to C terminus (SEQ ID NO:3).

FIG. 4 shows the amino acid sequence of the Fc domain of canine IgG1 immunoglobulin type C (caHCC) from the hinge region to C terminus (SEQ ID NO:4).

FIG. 5 shows the amino acid sequence of the Fc domain of canine IgG1 immunoglobulin type D (caHCD) from the hinge region to C terminus (SEQ ID NO:5).

FIG. 6 shows the amino acid sequence of SEQ ID NO:6 which is a chimeric fusion polypeptide comprising the canine TNFR sequence of SEQ ID NO:1 and the canine IgG HCA Fc domain of SEQ ID NO:2.

FIG. 7 shows the amino acid sequence of SEQ ID NO:7 which is a chimeric fusion polypeptide comprising the canine TNFR sequence of SEQ ID NO:1 and the canine IgG HCB Fc domain of SEQ ID NO:3.

FIG. 8 shows the amino acid sequence of SEQ ID NO:8 which is a chimeric fusion polypeptide comprising the canine TNFR sequence of SEQ ID NO:1 and the canine IgG HCC Fc domain of SEQ ID NO:4.

FIG. 9 shows the amino acid sequence of SEQ ID NO:9 which is a chimeric fusion polypeptide comprising the canine TNFR sequence of SEQ ID NO:1 and the canine IgG HCD Fc domain of SEQ ID NO:5.

FIG. 10 shows the amino acid sequence of SEQ ID NO:10 which is a chimeric fusion polypeptide comprising the canine TNFR sequence of SEQ ID NO:1 and an aglycosyl version of the canine IgG HCA Fc domain of SEQ ID NO:2.

FIG. 11 shows the amino acid sequence of SEQ ID NO:11 which is a chimeric fusion polypeptide comprising the canine TNFR sequence of SEQ ID NO:1 and an aglycosyl version of the canine IgG HCB Fc domain of SEQ ID NO:3.

FIG. 12 shows the amino acid sequence of SEQ ID NO:12 which is a chimeric fusion polypeptide comprising the canine TNFR sequence of SEQ ID NO:1 and an aglycosyl version of the canine IgG HCC Fc domain of SEQ ID NO:4.

FIG. 13 shows the amino acid sequence of SEQ ID NO:13 which is a chimeric fusion polypeptide comprising the canine TNFR sequence of SEQ ID NO:1 and an aglycosyl version of canine IgG HCD Fc domain of SEQ ID NO:5.

FIG. 14 shows the amino acid sequence of the canine TNF Receptor (TNFR) p80 extracellular domain (ECD) fragment (SEQ ID NO:14).

FIG. 15 shows the amino acid sequence of SEQ ID NO:15 which is a chimeric fusion polypeptide comprising the canine TNFR sequence of SEQ ID NO:14 and the canine IgG HCA Fc domain of SEQ ID NO:2.

FIG. 16 shows the amino acid sequence of SEQ ID NO:16 which is a chimeric fusion polypeptide comprising the canine TNFR sequence of SEQ ID NO:14 and the canine IgG HCB Fc domain of SEQ ID NO:3.

FIG. 17 shows the amino acid sequence of SEQ ID NO:17 which is a chimeric fusion polypeptide comprising the canine TNFR sequence of SEQ ID NO:14 and the canine IgG HCC Fc domain of SEQ ID NO:4.

FIG. 18 shows the amino acid sequence of SEQ ID NO:18 which is a chimeric fusion polypeptide comprising the canine TNFR sequence of SEQ ID NO:14 and the canine IgG HCD Fc domain of SEQ ID NO:5.

FIG. 19 shows the amino acid sequence of SEQ ID NO:19 which is a chimeric fusion polypeptide comprising the canine TNFR sequence of SEQ ID NO:14 and an aglycosyl version of the canine IgG HCA Fc domain of SEQ ID NO:2.

FIG. 20 shows the amino acid sequence of SEQ ID NO:20 which is a chimeric fusion polypeptide comprising the canine TNFR sequence of SEQ ID NO:14 and an aglycosyl version of the canine IgG HCB Fc domain of SEQ ID NO:3.

FIG. 21 shows the amino acid sequence of SEQ ID NO:21 which is a chimeric fusion polypeptide comprising the canine TNFR sequence of SEQ ID NO:14 and an aglycosyl version of the canine IgG HCC Fc domain of SEQ ID NO:4.

FIG. 22 shows the amino acid sequence of SEQ ID NO:22 which is a chimeric fusion polypeptide comprising the canine TNFR sequence of SEQ ID NO:14 and an aglycosyl version of canine IgG HCD Fc domain of SEQ ID NO:5.

FIG. 30 shows the derivation of a novel canine TNFR p80 extracellular domain amino acid sequence (SEQ ID NO:14).

DETAILED DESCRIPTION OF THE INVENTION

Figure 23:
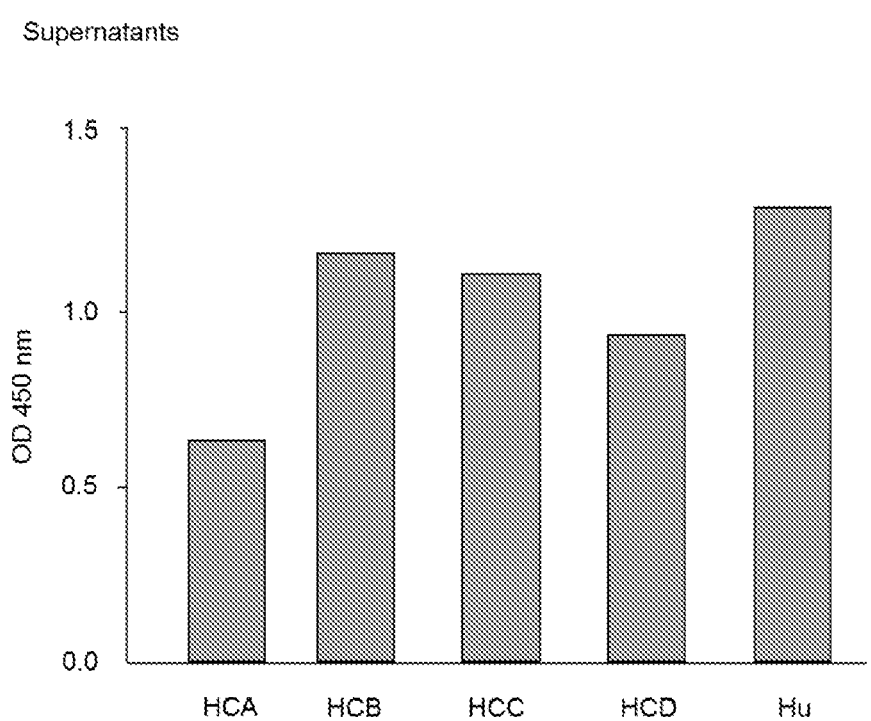
FIG. 23 is a graph showing the results of an ELISA of the binding of canine TNF of supernatants of expressed canine TNFR-Fc fusion proteins detected using a secondary anti-canine IgG polyclonal antibody-HRP conjugate. Transfection of CHO cells with expression plasmids encoding SEQ ID NO:6 (HCA), SEQ ID NO:7 (HCB), SEQ ID NO:8 (HCC) and SEQ ID NO:9 (HCD) resulted in the various supernatants tested being compared to an equivalent human TNFR-Fc extracellular domain fused N-terminally to canine HCB hinge-CH2-CH3 in an analogous fusion to SEQ ID NO:7.

The present inventors have provided compositions and methods for use in the treatment and prevention of TNF mediated conditions in a canine. In particular, the compositions and methods of the invention serve to reduce TNF levels systemically or at a particular anatomical location.

In particular, it is demonstrated herein that, despite fusion of complement recruiting varieties of canine immunoglobulin heavy chain constant domains to the canine TNF receptor extracellular domain, the resultant chimeric fusion polypeptides of the invention bind to canine TNF with high specificity and yet do not recruit complement C1q. Furthermore, binding sequesters the biological activity of canine TNF by inhibiting the binding of canine TNF to cell membrane expressed TNF receptors. This, in turn, will prevent or reduce the occurrence of a TNF mediated induction, development or progression of inflammatory mediated diseases in canines, such as arthritis, without concomitant damage through induction of the complement cascade.

The receptor fusion proteins of the invention are produced using recombinant DNA methods and exhibit binding specificity for canine TNF, whilst also having canine constant domain sequences which reduce their immunogenicity when administered to a canine host. As a result, the risk of xeno-antibody induction is minimised.

The invention provides recombinant fusion proteins which comprise the extracellular domain of the canine TNF receptor p60 (caTNFRp60) conjoined with the Fc domain of a canine IgG immunoglobulin isotype. The invention further extends to recombinant fusion proteins which comprise the extracellular domain of the canine TNF receptor p80 (caTNFRp80) conjoined with the Fc domain of a canine IgG immunoglobulin isotype. The resulting dimeric polypeptides are chimeric Fc fusion proteins. The inventors have shown that the caTNFRp60:Fc fusion protein has binding specificity to canine TNF and acts as a TNF antagonist. Use of TNF antagonists has been shown to reverse the effects of TNF mediated progression of inflammatory disease and other TNF-mediated conditions.

The fusion protein compositions of the present invention are typically administered exogenously, for example, by intravenous or subcutaneous administration. However, in certain embodiments a vector may be used to deliver a polynucleotide which encodes a chimeric fusion polypeptide of the invention. The invention therefore provides compositions and methods for the effective and continuous treatment of TNF-mediated inflammatory diseases and other TNF-associated conditions and disorders.

Following extensive experimentation, the inventors have taken a canine protein sequence with similarity to the human TNF receptor extracellular domain (Accession number AAD01516, Campbell, et al. 2001, Vet Immuno Immunopath 78, 207-214), a receptor which was not previously known to have binding specificity to canine TNF, and have surprisingly used this as the basis to produce antagonistic receptor-immunoglobulin fusion proteins (fusion polypeptides) which bind specifically to canine TNF-alpha and yet do not recruit complement C1q.

The resulting non-immunogenic receptor fusion proteins are shown to exhibit high affinity binding to canine TNF. The receptor fusion proteins neutralise canine TNF biological function, most specifically by inhibiting the binding of TNF to the cell membrane associated receptor TNFR1. Furthermore, the fusion proteins have also been designed so that the constant regions incorporate only residues present in canine IgG molecules so that when administered to a canine, xenoantibodies are unlikely to be produced there against. Accordingly, the caninised receptor fusion proteins of the invention are suitable for long-term administration for the treatment of chronic inflammatory diseases in canines.

The inventors have surprisingly, for the first time, identified the complete canine p80 TNF receptor extracellular domain in its entirety by combining the predicted carboxy terminal residues of NCBI genomic reference clone XP_544562.2 (which the inventors have identified as including an incorrectly predicted signal sequence and amino terminal residues of canine p80) with the correct signal sequence and amino terminal residues from the partial canine cDNA clone DN368636. This novel canine p80 extracellular domain sequence (FIG. 30) is shown as SEQ ID NO:14 herein. As a result, the correct entire canine p80 extracellular domain can be synthesised with its appropriate amino terminal residues intact and consequently will not be immunogenic when administered to a canine subject. By comparison, the sequence derived from clone XP_544562.2 would generate a foreign and immunogenic amino terminus against which neutralising antibodies would be raised when administered to a canine. Similarly, canine TNF receptor p80-immunoglobulin Fc domain fusion proteins can be provided using the herein determined corrected p80 amino terminus amino acid sequence (SEQ ID NO:15-22 herein).

The process of generating the receptor fusion proteins of the invention which has been employed by the inventors results in the presentation of the receptor extracellular domain which, based on the inventors' analysis, will retain the conformation of the receptor and therefore maintain binding specificity and avidity, and increase the receptor size above that eliminated in the kidney, while reducing the presence of immunogenic epitopes which may result in neutralising antibodies (particularly xenoantibodies) being generated against the receptor if it were to be administered to canines in an unaltered form.

Further, the Fc domain components of the fusion proteins comprise IgG immunoglobulin heavy chain constant regions obtained from canine derived antibodies, canines being the target species to which the fusion proteins of the invention are to be administered. The immunoglobulin heavy chain constant domains are selected or modified such that they do not mediate downstream effector functions. Furthermore, as the fusion of the receptor extracellular domain to the immunoglobulin heavy chain constant domain is performed in such a manner that it does not affect the three dimensional conformation of the receptor domain, there will be no variation in binding specificity to the desired target.

There are four major IgG isotypes in man and mouse and while nomenclature is similar they differ in behaviour and function, including affinity for bacterial products, such as Protein A and Protein G, and their ability to activate the complement dependent cytolysis (CDC) and to induce killing of target cells through antibody dependent cellular cytotoxicity (ADCC). The selection of IgG isotypes with CDC and ADCC active or "armed" constant domains is considered to be of clinical benefit when antibodies are designed to eliminate target cells bearing their cognate antigen, such as in oncology or infection control (e.g. in human medical use, human IgG1 isotypes are preferred for the above purposes). By contrast, the activation of the immune system is considered undesirable in other settings, such as in the relief of inflammation, pain or autoimmunity and so human IgG isotypes with minimal CDC and ADCC activity are preferred (e.g. in such human medical use, IgG4 isotypes are often preferred). Four distinct immunoglobulin gamma (IgG) heavy chain constant domain isotypes have been described in the canine immune system (U.S. Pat. No. 5,852,183, Tang L. et al. 2001. Veterinary Immunology and Immunopathology, 80. 259-270), along with single kappa and lambda constant domain sequences. The four canine heavy chain constant domains A, B, C and D have not been characterised in terms of the immune system functional activity which they mediate. Despite overall homology to the IgG family, the proteins encoding canine IgG are more related to one another than to family members from other species, so it has not been possible by homology alone to define which of the above functions, if any, can be ascribed to each of the four canine isotypes. However, the inventors have surprisingly identified that canine IgG subtypes B and C do not mediate downstream effector functions, in particular, complement fixation and, accordingly, polypeptide fragments derived from canine IgG subtypes B and C are preferred in the chimeric fusion polypeptides of the invention.

In certain embodiments the receptor fusion proteins are produced comprising Fc domain components which have altered glycosylation patterns. In certain embodiments a TNF receptor-Fc fusion protein of the invention can be altered to increase or decrease the extent to which the Fc portion is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose or xylose to a hydroxyamino acid, most commonly serine or threonine, although 5-hydroxyproline or 5-hydroxylysine may also be used.

In certain further embodiments the anti-canine TNF receptor fusion proteins of the invention can be PEGylated by reacting the receptor fusion protein with a polyethylene glycol (PEG) derivative. In certain embodiments the receptor fusion protein is defucosylated and therefore lacks fucose residues.

In certain embodiments modifications to the biological properties of a protein may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (A. L. Lehninger, in Biochemistry, $2^{nd}$ Ed., 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His (H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. Non-conservative substitutions will entail exchanging a member of one of these classes for another class. Such substituted residues may also be introduced into the conservative substitution sites or into the remaining (e.g. non-conserved) sites.

The receptor fusion proteins and binding members of the invention may be produced wholly or partly by chemical synthesis. For example, the canine TNF receptor fusion proteins and binding members of the invention can be prepared by techniques which are well known to the person skilled in the art, such as standard liquid peptide synthesis or by solid-phase peptide synthesis methods. Alternatively, the fusion proteins may be prepared in solution using liquid phase peptide synthesis techniques, or further by a combination of solid-phase, liquid phase and solution chemistry.

The present invention further extends to the production of the receptor fusion proteins or binding members of the invention by expression of polynucleotide(s) which encode the chimeric fusion polypeptide or components thereof in a suitable expression system.

Nucleic acid sequences encoding the receptor fusion proteins of the invention can be readily prepared by the skilled person using techniques which are well known to those skilled in the art, such as those described in Sambrook et al. "Molecular Cloning", A laboratory manual, cold Spring Harbor Laboratory Press, Volumes 1-3, 2001 (ISBN-0879695773), and Ausubel et al. Short Protocols in Molecular Biology. John Wiley and Sons, $4^{th}$ Edition, 1999 (ISBN-0471250929).

Nucleic acid sequences encoding the receptor fusion proteins of the invention may be provided as constructs in the form of a plasmid, vector, transcription or expression cassette which comprises at least one nucleic acid. The construct may be comprised within a recombinant host cell which comprises one or more constructs. Expression may conveniently be achieved by culturing, under appropriate conditions, recombinant host cells containing suitable nucleic acid sequences. Following expression, the receptor fusion protein or receptor fusion protein fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells and NS0 mouse myeloma cells. A common, preferred bacterial host is *E. coli*. The expression of receptor fusion proteins and receptor fusion protein fragments in prokaryotic cells such as *E. coli* is well established in the art. Expression in eukaryotic cells in culture is also available to those skilled in the art as an option for production of a polypeptide.

A receptor fusion protein of the invention may be produced by recombinant means, not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native receptor signal sequence, the signal sequence is substituted by a prokaryotic signal sequence selected, for example, from the group of the alkaline phosphatase, penicillinase, lpp, and heat-stable enterotoxin II leaders.

The term "isolated", when used in reference to the receptor fusion proteins of the invention, or to binding members derived therefrom, or polynucleotides which encode the same, refers to the state in which said receptor fusion proteins or polynucleotides are provided in an isolated and/or purified form, that is they have been separated, isolated or purified from their natural environment, and are provided in a substantially pure or homogeneous form, or, in the case of nucleic acids, free or substantially free of nucleic acid or genes of origin other than the sequence encoding a polypeptide with the required function. Accordingly, such isolated receptor fusion proteins and isolated nucleic acids will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo.

Receptor fusion proteins and nucleic acids may be formulated with diluents or adjuvants and still, for practical purposes, be considered as being provided in an isolated form. For example the receptor fusion proteins can be mixed with gelatin or other carriers if used to coat microtitre plates for use in immunoassays, or will be mixed with pharmaceutically acceptable carriers or diluents when used in diagnosis or therapy. The receptor fusion proteins may be glycosylated, either naturally or by systems of heterologous eukaryotic cells (e.g. CHO or NSO cells), or they may be (for example if produced by expression in a prokaryotic cell) unglycosylated.

Heterogeneous preparations comprising anti-canine TNF receptor fusion protein molecules also form part of the invention. For example, such preparations may be mixtures of receptor fusion proteins with receptor fusion proteins lacking the C-terminal lysine, with various degrees of glycosylation and/or with derivatised amino acids, such as cyclization of an N-terminal glutamic acid to form a pyroglutamic acid residue.

Typically the pharmaceutical compositions of the invention are formulated in a liquid formulation, a lyophilized formulation, a lyophilized formulation that is reconstituted as a liquid, or as an aerosol formulation. In certain embodiments the receptor fusion protein in the formulation is at a concentration of about 0.5 mg/ml to about 250 mg/ml, about 0.5 mg/ml to about 45 mg/ml, about 0.5 mg/ml to about 100 mg/ml, about 100 mg/ml to about 200 mg/ml or about 50 mg/ml to about 250 mg/ml.

In certain embodiments the formulation further comprises a buffer. Typically the pH of the formulation is from about pH 5.5 to about pH 6.5. In certain embodiments the buffer may comprise from about 4 mM to about 60 mM histidine buffer, about 5 mM to about 25 mM succinate buffer, or about 5 mM to 25 mM acetate buffer. In certain embodiments the buffer comprises sodium chloride at a concentration of from about 10 mM to 300 mM, typically at around 125 mM concentration and sodium citrate at a concentration of from about 5 mM to 50 mM, typically 25 mM. In certain embodiments the formulation can further comprise a surfactant at a concentration of just above 0% to about 0.2%. In certain embodiments the surfactant is selected from the group consisting of, but not limited to, polysorbate-20, polysorbate-40, polysorbate-60, polysorbate-65, polysorbate-80, polysorbate-85, and combinations thereof. In a preferred embodiment the surfactant is polysorbate-20 and may further comprise sodium chloride at a concentration of about 125 mM and sodium citrate at a concentration of about 25 mM.

The receptor fusion proteins of the invention may be administered alone, but will preferably be administered as a pharmaceutical composition which will generally comprise a suitable pharmaceutically acceptable excipient, diluent or carrier selected depending on the intended route of administration. Examples of suitable pharmaceutical carriers include water, glycerol, ethanol and the like.

The receptor fusion protein or binding member of the present invention may be administered to a canine in need of treatment exogenously or via any other suitable route. Typically, the composition can be administered parenterally by injection or infusion. Examples of preferred routes for parenteral administration include, but are not limited to, intravenous, intraperitoneal, intramuscular, subcutaneous or transmucosal. Routes of administration may further include topical and enteral, for example, mucosal (including pulmonary), oral, nasal and rectal.

In embodiments where the composition is delivered as an injectable composition, for example in intravenous, intradermal or subcutaneous application, the active ingredient can be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required. The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7.

The receptor fusion proteins and compositions of the invention are typically administered to a subject in a "therapeutically effective amount", this being an amount sufficient to show benefit to the subject to whom the composition is administered. The actual dose administered, and rate and time-course of administration, will depend on, and can be determined with due reference to, the nature and severity of the condition which is being treated, as well as factors such as the age, sex and weight of the subject being treated, as well as the route of administration. Further due consideration should be given to the properties of the composition, for example, its binding activity and in-vivo plasma life, the concentration of the receptor fusion protein or binding member in the formulation, as well as the route, site and rate of delivery.

Dosage regimens can include a single administration of the receptor fusion protein or composition of the invention, or multiple administrative doses of the receptor fusion protein or composition. The receptor fusion protein or receptor fusion protein containing compositions can further be administered sequentially, simultaneously or separately with other anti-inflammatory or TNF antagonist compositions.

Examples of dosage regimens which can be administered to a subject can be selected from the group comprising, but not limited to, 1 µg/kg/day through to 20 mg/kg/day, 1 µg/kg/day through to 10 mg/kg/day and 10 µg/kg/day through to 1 mg/kg/day. In certain embodiments the dosage will be such that a plasma concentration of from 1 µg/ml to 100 µg/ml of the antibody is obtained. However, the actual dose of the composition administered, and rate and time-course of administration, will depend on the nature and severity of the condition being treated. Prescription of treatment, e.g. decisions on dosage etc., is ultimately within the responsibility and at the discretion of veterinary practitioners and other veterinary doctors, and typically takes account of the disorder to be treated, the condition of the individual patient, the site of delivery, the method of administration and other factors known to practitioners.

Definitions

Unless otherwise defined, all technical and scientific terms used herein have the meaning commonly understood by a person who is skilled in the art in the field of the present invention. The meaning and scope of the terms should be clear, however, in the event of any ambiguity, definitions provided herein take precedence over any dictionary or extrinsic definition.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

As used herein, terms such as "a", an and "the" include singular and plural instances unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like. Further, unless otherwise required by context, singular terms shall include pluralities and plural terms shall include the singular.

Typically, the chimeric fusion polypeptide of the invention is a neutralising receptor fusion protein. As defined herein, the term "neutralising receptor fusion protein" describes a receptor fusion protein that is capable of neutralising the biological activity and signalling of TNF. The neutralising receptor fusion protein, which may also be referred to as a TNF antagonist fusion protein, an antagonistic receptor fusion protein, or a blocking receptor fusion protein, specifically and preferably selectively, binds to TNF and inhibits one or more biological activities of TNF. For example, the neutralising receptor fusion protein may inhibit the binding of TNF to its target receptor, such as the cell membrane bound TNF Receptor 1 (TNFR1) receptor (CD120a).

As used herein, the term "biological activity" refers to any one or more inherent biological properties of a molecule (whether present naturally as found in vivo, or provided or enabled by recombinant means). Biological properties include, but are not limited to, receptor binding and/or activation, induction of cell signalling or cell proliferation, inhibiting cell growth, induction of cytokine production, induction of apoptosis and enzymatic activity.

The term "constant region (CR)" as used herein, refers to the portion of the antibody molecule which confers effector functions. In the present invention, constant regions typically mean canine constant regions, that is, that the constant regions are from canine immunoglobulins.

The term "immunogenicity" as used herein refers to a measure of the ability of a protein or therapeutic moiety to elicit an immune response (humoral or cellular) when administered to a recipient. Preferably the chimeric fusion polypeptides of the present invention have no immunogenicity, that is, that no xenoantibodies will be raised against them when administered to a canine.

The term "identity" or "sequence identity" or "homology" as used herein, means that at any particular amino acid residue position in an aligned sequence, the amino acid residue is identical between the aligned sequences. The term "similarity" or "sequence similarity" as used herein, indicates that, at any particular position in the aligned sequences, the amino acid residue is of a similar type between the sequences. For example, leucine may be substituted for an isoleucine or valine residue. This may be referred to as conservative substitution. Preferably when the amino acid sequences of the invention are modified by way of conservative substitution of any of the amino acid residues contained therein, these changes have no effect on the binding specificity or functional activity of the resulting receptor fusion protein when compared to the unmodified receptor fusion protein.

Sequence identity with respect to a (native) polypeptide of the invention and its functional derivative relates to the percentage of amino acid residues in the candidate sequence which are identical with the residues of the corresponding native polypeptide after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology. Methods and computer programs for performing an alignment of two or more amino acid sequences and determining their sequence identity or homology are well known to the person skilled in the art. For example, the percentage of identity or similarity of two amino acid sequences can be readily calculated using algorithms e.g. BLAST (Altschul et al. 1990), FASTA (Pearson & Lipman 1988), or the Smith-Waterman algorithm (Smith & Waterman 1981). The present invention extends to sequences having at least 80%, 85%, 90%, 93%, 95%, 96%, 97%, 98% or 99% sequence identity or sequence homology with the sequences identified herein, and to use of same in the methods of the invention described herein.

The term "consists essentially of" or "consisting essentially of" as used herein means that a polypeptide may have additional features or elements beyond those described provided that such additional features or elements do not materially affect the ability of the receptor fusion protein or receptor fusion protein fragment to have binding specificity to canine TNF. That is, the receptor fusion protein or receptor fusion protein fragments comprising the polypeptides may have additional features or elements that do not interfere with the ability of the receptor fusion protein or receptor fusion protein fragments to bind to canine TNF and antagonise canine TNF functional activity. Such modifications may be introduced into the amino acid sequence in order to reduce the immunogenicity of the receptor fusion protein. For example, a polypeptide consisting essentially of a specified sequence may contain one, two, three, four, five or more additional, deleted or substituted amino acids, at either end or at both ends of the sequence provided that these amino acids do not interfere with, inhibit, block or interrupt the role of the receptor fusion protein or fragment in binding to canine TNF and sequestering its biological function. Similarly, a polypeptide molecule which contributes to the canine TNF antagonistic receptor fusion proteins of the invention may be chemically modified with one or more functional groups provided that such functional groups do not interfere with the ability of the receptor fusion protein or receptor fusion protein fragment to bind to canine TNF and antagonise its function.

As used herein, the term "effective amount" or "therapeutically effective amount" means the amount of a fusion protein of the invention which is required to suppress canine TNF binding to the TNFR1 receptor and/or an amount of the chimeric fusion polypeptide of the invention which is sufficient to effect beneficial or desired clinical results. An effective amount may be administered in one or more administrations. For the purposes of this invention, an "effective amount" is an amount that achieves at least one of the following: a reduction in TNF levels, a reduction of an inflammatory response or a reduction, prevention or amelioration of a TNF-mediated disease or condition As used herein, the term "chimeric polypeptide", "fusion polypeptide", "fusion protein" or "dimeric polypeptide" is a polypeptide which comprises at least two domains which are derived from different proteins. These domains are brought together in the chimeric, dimeric or fusion protein to form a novel protein, typically due to the extracellular domain, or a fragment thereof of the p60 canine TNF receptor (p60TNFR) or the p80 canine TNF receptor (p80TNFR)

being conjoined with the whole or a part of an Fc domain derived from a canine IgG immunoglobulin heavy chain constant region.

The terms "polypeptide", "peptide", or "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide.

The terms "polynucleotide" and "nucleic acid" are used interchangeably to refer to polymeric forms of nucleotides of any length. The term polynucleotide also refers interchangeably to double and single stranded molecules.

As defined herein, a "canine" may also be referred to as a dog. Canines can be categorised as belonging to the subspecies with the trinomial name Canis lupus familiaris (Canis familiaris domesticus) or Canis lupus dingo. Canines include any species of dog and include both feral and pet varieties, the latter also being referred to as companion animals.

The phrase "specifically binds to" refers to the binding of an antibody or protein to a specific protein or target which is present amongst a heterogeneous population of proteins. Hence, when present in specific immunoassay conditions, the proteins bind to a particular protein, in this case canine TNF, and do not bind in a significant amount to other proteins present in the sample.

As defined herein, the term "xenoantibody" refers to an antibody which is raised by the host against an epitope which is foreign to the host.

The present invention will now be described with reference to the following examples which are provided for the purpose of illustration and are not intended to be construed as being limiting on the present invention. The methods and techniques of the present invention are generally performed according to conventional methods well known in the art and as described in various general and more specific references that are cited and discussed throughout the present specification unless otherwise indicated.

EXAMPLES

Example 1—Expression of DNA Encoding Anti-Canine TNF Receptor Fusion Proteins

An ELISA was performed to determine the binding to canine TNF of supernatants of expressed canine TNFR-Fc fusion proteins detected using a secondary anti-canine IgG polyclonal antibody-HRP conjugate. The results are shown in FIG. 23.

Transfection of CHO cells with expression plasmids encoding SEQ ID NO:6 (HCA (caTNFRp50:ca IgGHCA Fc)), SEQ ID NO:7 (HCB (caTNFRp50:ca IgGHCB Fc)), SEQ ID NO:8 (HCC (caTNFRp50:ca IgGHCC Fc)) and SEQ ID NO:9 (HCD (caTNFRp50:ca IgGHCD Fc)) resulted in the various supernatants which were tested and these were compared to an equivalent human TNFR-Fc comprising a human TNFR extracellular domain fused N-terminally to canine HCB hinge-CH2-CH3 in an analogous fusion to SEQ ID NO:7.

Figure 24:
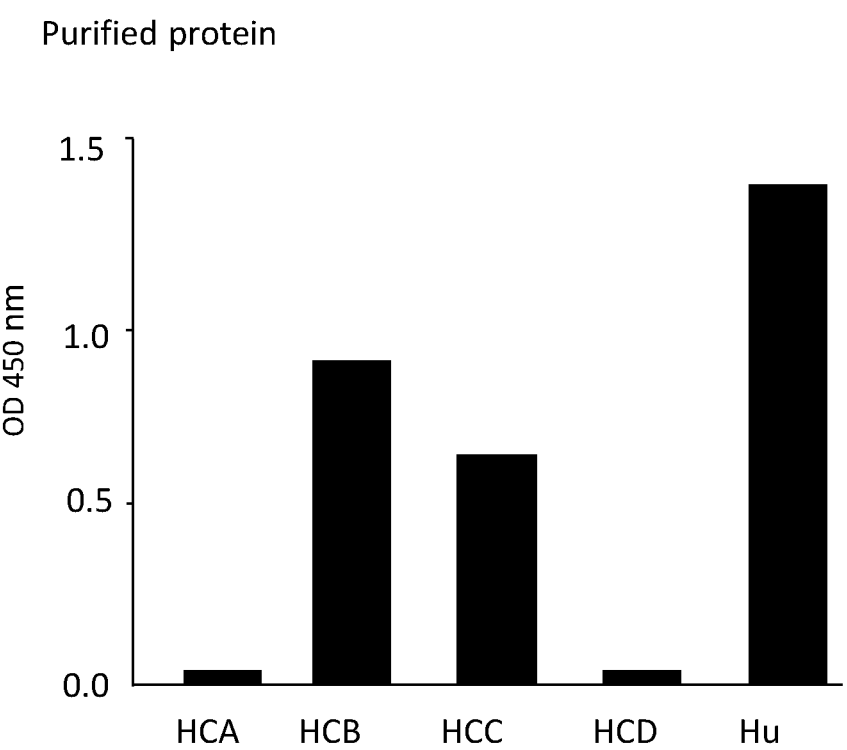
FIG. 24 is a graph showing an ELISA of binding of purified canine TNFR-Fc fusion proteins post affinity capture on tandem Protein A and Protein G sepharose columns. As can be seen from this Figure, the HCB and HCC forms of the canine TNF receptor fusion proteins were efficiently captured by Protein A or Protein G, whereas the HCA and HCD forms of the fusion proteins were poorly captured. Further analysis (not shown) demonstrated that the canine TNFR-HCB was captured efficiently by Protein A whereas the HCC form was captured by Protein G.

FIG. 24 shows the results of an ELISA of binding of purified canine TNFR-Fc fusion proteins post affinity capture on tandem Protein A and Protein G sepharose columns. As can be seen from this Figure, the HCB and HCC forms of the canine TNF receptor fusion proteins were efficiently captured by Protein A or Protein G, whereas the HCA and HCD forms of the fusion proteins were poorly captured. Further analysis (not shown) demonstrated that the canine TNFR-HCB was captured efficiently by Protein A whereas the canine TNFR-HCC form was able to be captured by Protein G.

Figure 25:
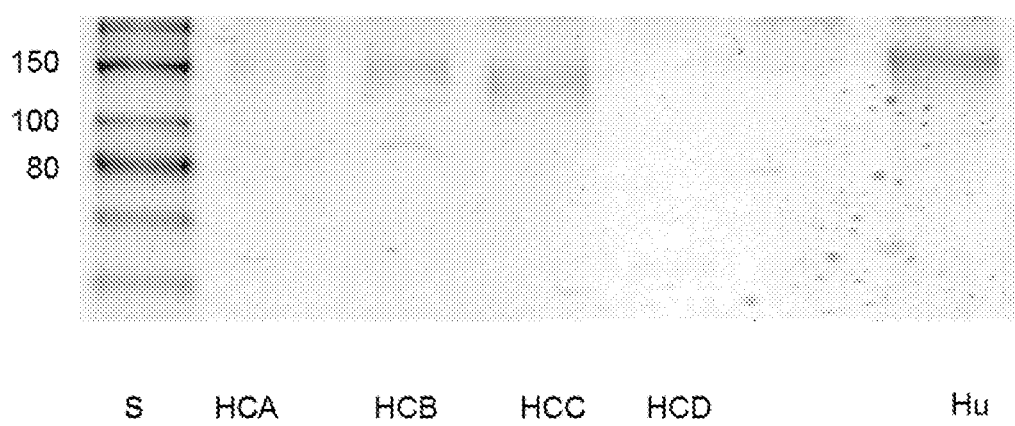
FIG. 25 show the results of a non reducing SDS-PAGE gel of the products of tandem Protein A and Protein G affinity chromatography confirming the poor recovery of HCA (SEQ ID NO:6) and HCD (SEQ ID NO:9) isoforms of canine TNFR fusion proteins.

FIG. 25 show the results of a non-reducing SDS-PAGE gel of the products of tandem Protein A and Protein G affinity chromatography confirming the poor recovery of HCA (SEQ ID NO:6) and HCD (SEQ ID NO:9) isoforms of canine TNFR fusion proteins.

Example 2—Inhibition of Canine TNF Activity

Figure 26:
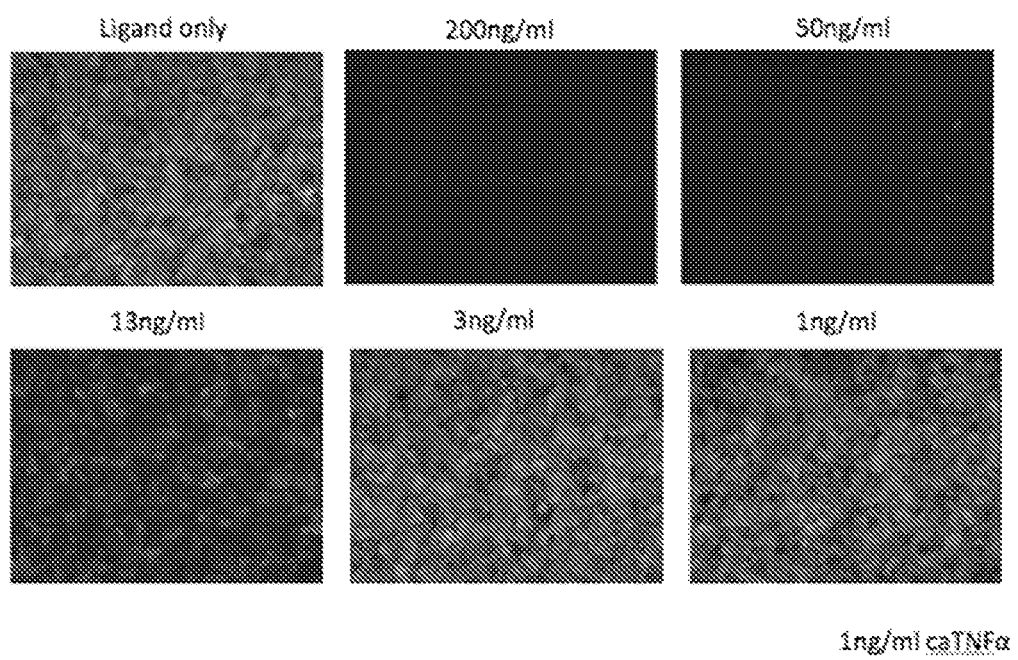
FIGS. 26 and 27 show inhibition of canine TNFalpha bioactivity (R&D systems, 1 ng/ml) using 293-HEK cells transfected with the NF-kB-EGFP reporter construct pTRH1 (Vince et al, Cell 131, 682, 2007). These cells respond to canine TNF by fluorescence. Both the canine TNFR-HCB (SEQ ID NO:7) (FIG. 26) and canine TNFR-HCC (SEQ ID NO:8) (FIG. 27) isoforms of canine TNFR fusion proteins inhibited TNF-induced fluorescence equally as well as the human TNFR-canine HCB control fusion protein (quantified in FIG. 27). The IC50 for the assay was approximately 1 ng/ml.
Figure 27:
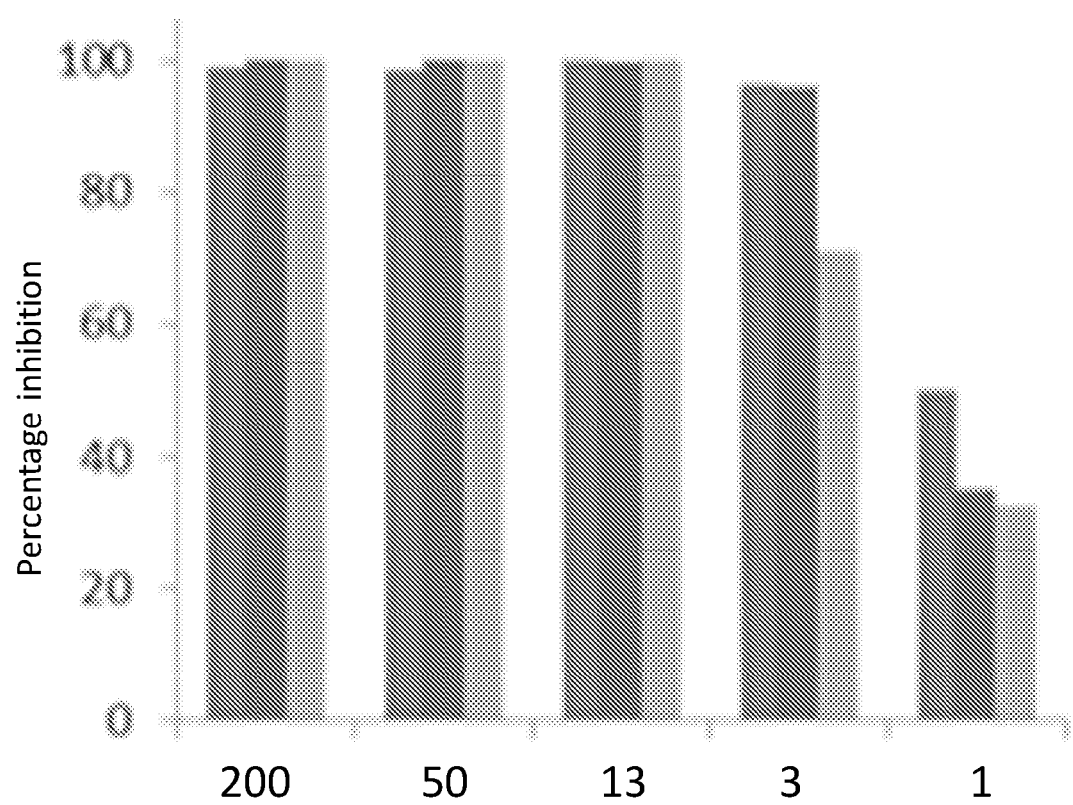

This experiment assessed whether the fusion polypeptides of the invention acted as antagonists of TNF biological activity. FIGS. 26 and 27 show the results of inhibition of canine TNF-alpha bioactivity (R&D systems, 1 ng/ml) using 293-HEK cells transfected with the NF-kB-EGFP reporter construct pTRH1 (Vince et al., Cell 131, 682, 2007). These cells respond to canine TNF by fluorescence. Both the canine TNFR-HCB (SEQ ID NO:7) (FIG. 26) and canine TNFR-HCC (SEQ ID NO:8) (FIG. 27) isoforms of canine TNFR fusion proteins inhibited TNF-induced fluorescence equally as well as the human TNFR-canine HCB control fusion protein (quantified in FIG. 27). The IC50 for the assay was approximately 1 ng/ml.

Example 3—TNF Receptor Fusion Proteins Lack Complement Activity

Figure 28:
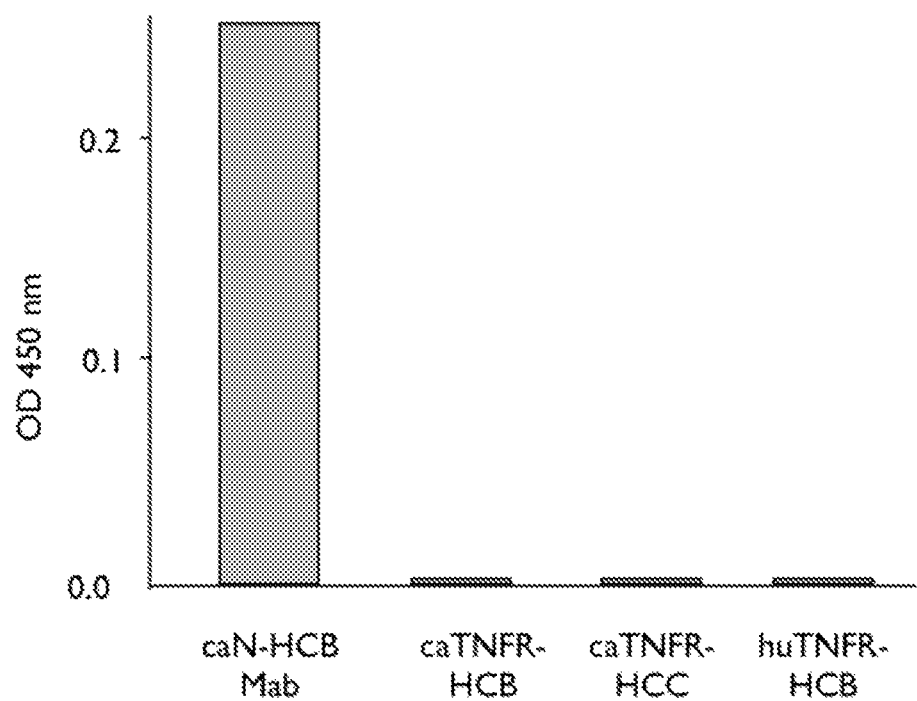
FIG. 28 shows the results of a complement C1q binding ELISA. The canine TNFR-HCB, canine TNFR-HCC and human TNFR-canine HCB fusion proteins were incubated with plates pre-coated with canine TNF (4 µg/ml). For comparison, a caninised monoclonal antibody (MAb, canine isotype HCB) with specificity to nerve growth factor (NGF) was incubated with plates coated with NGF. The plates were washed and incubated with normal or heat-killed human serum as a source of complement. Binding of complement C1q was detected using a C1q reactive polyclonal antibody-HRP conjugate. As can be seen from the results, whereas the canine HCB MAb was able to recruit complement, surprisingly, neither the canine nor human TNFR-HCB fusion proteins, nor the canine TNFR-HCC fusion protein was able to recruit complement (in other experiments the HCC isotype of the anti-NGF monoclonal antibodies binds C1q; data not shown).

FIG. 28 shows the results of a complement C1q binding ELISA. The canine TNFR-HCB, canine TNFR-HCC and human TNFR-canine HCB fusion proteins were incubated with plates pre-coated with canine TNF (4 µg/ml). For comparison, a caninised monoclonal antibody (MAb, canine isotype HCB) with specificity to nerve growth factor (NGF) was incubated with plates coated with NGF. The plates were washed and incubated with normal or heat-killed human serum as a source of complement. Binding of complement C1q was detected using a C1q reactive polyclonal antibody-HRP conjugate. As can be seen from the results, whereas the canine HCB monoclonal antibody was able to recruit complement, surprisingly, neither the fully canine nor the chimeric human TNFR-canine HCB fusion proteins nor the canine TNFR-HCC fusion protein were able to recruit complement (in other experiments the HCC isotype of the anti-NGF MAbs binds C1q; data not shown).

Together these results show that the canine TNF receptor fusion proteins of the invention and the human TNFR-canine Fc chimera construct bind canine TNF and are equipotent by both ELISA and inhibition assay, demonstrating that the fusion process has produced fully active canine versions of TNF receptor fusion proteins.

Furthermore, these results show that purification by Protein A and Protein G cannot be achieved by simple fusion of any of the canine IgG heavy chain constant domains to a canine TNFR extracellular domain, since unexpectedly, neither the canine IgG HCA nor HCD constant domains conferred the ability to bind these useful purification materials. Consequently, the HCB and HCC IgG constant domains are desirable fusion partners for making TNFR-Fc fusion proteins (or any other canine receptor Fc fusion proteins) that can be usefully purified at scale for veterinary clinical use in treating diseases in the dog.

FIG. 28 shows that, unexpectedly, the design of the HCB and HCC isoforms of the canine TNF receptor fusion proteins resulted in a lack of ability to recruit complement. Accordingly, the canine TNF receptor fusion proteins show an unexpected combination of strong binding to canine TNF equivalent to that to of the human TNF receptor with a desirable lack of recruitment of complement damage to sites of TNF inflammatory activity. Therefore, the canine TNF receptor fusion proteins of the invention are surprisingly useful for the treatment of canine diseases mediated by canine TNF.

Figure 29A:
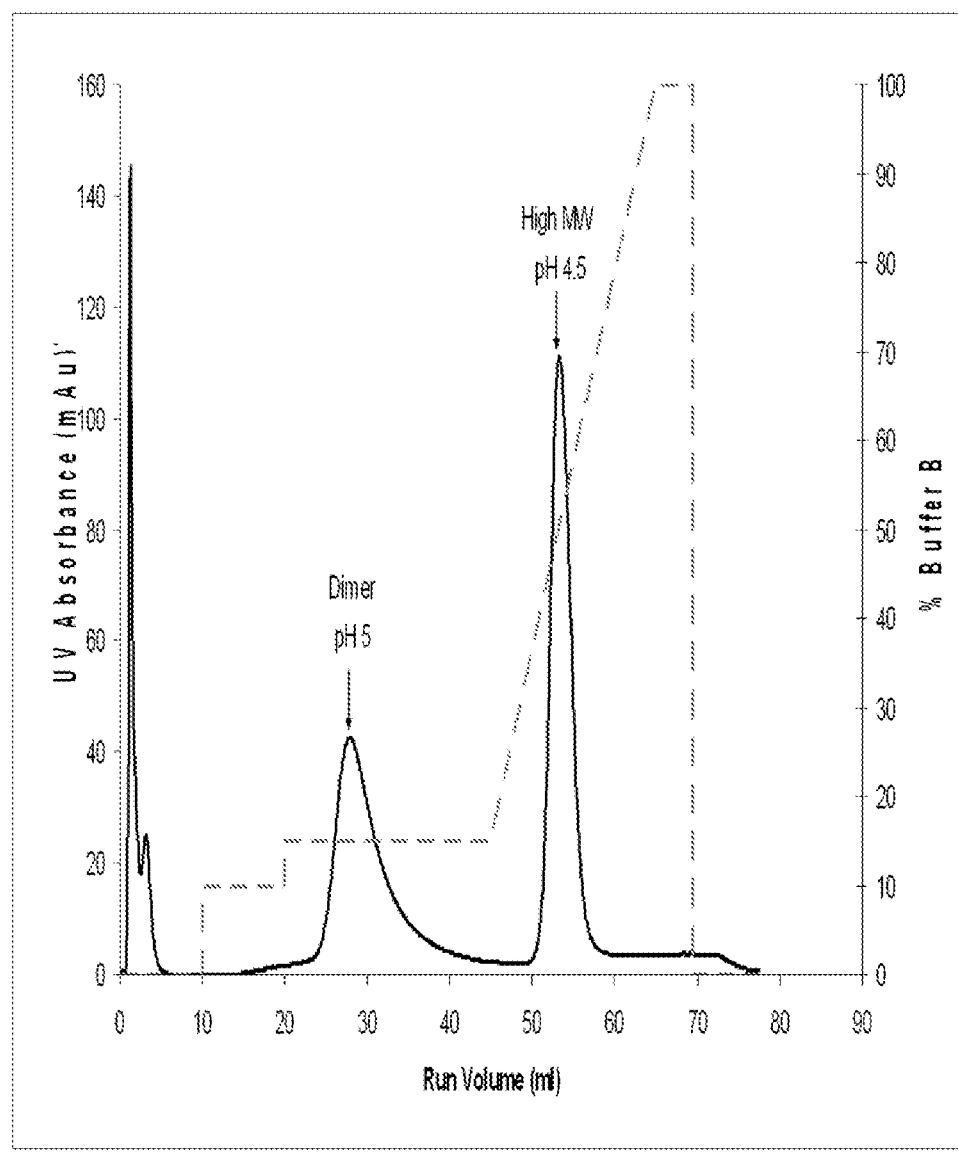
FIG. 29 shows the results of optimised purification of canine TNFR-HCB (SEQ ID NO:7) polypeptide fusion protein dimers from higher molecular weight aggregates of the same by selective elution at pH5.
Figure 29B:
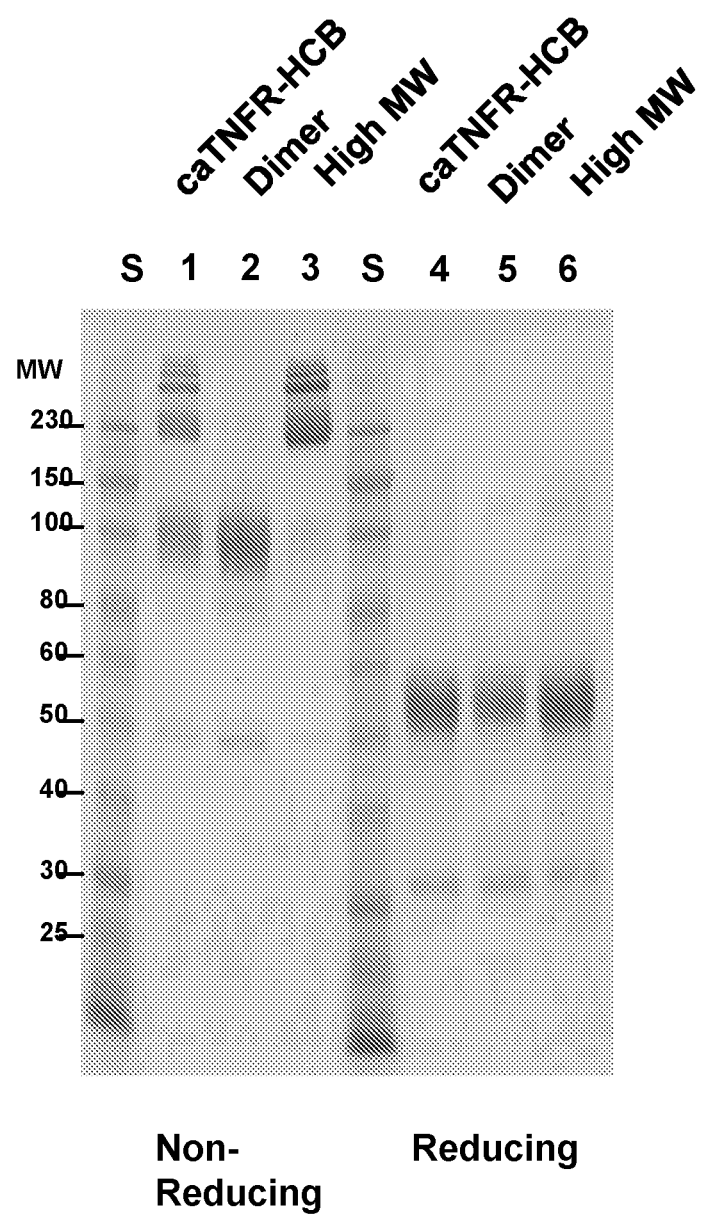

FIG. 29 shows the results of optimised purification of canine TNFR-HCB (SEQ ID NO:7) polypeptide fusion protein dimers from higher molecular weight aggregates of the same by selective elution at pH5. The standard procedure for Protein A purification of immunoglobulins is to bind at neutral pH and elute at pH3. The canine TNFR-HCB fusion protein (SEQ ID NO:7) can be captured and eluted this way, but a significant proportion of the CHO cell product is in the form of high molecular weight aggregates (FIG. 29B, lane 1; also FIG. 25, lane HCB, just entering the gel at the top of the figure). Such aggregates can be immunogenic and their removal is desirable. Surprisingly, the high molecular weight aggregates could be purified from the preferred dimer form of canine TNFR-HCB fusion protein by modification of the pH of the eluting buffer to a higher pH. In FIG. 29A, canine TNFR-HCB protein produced in CHO cells by expression of SEQ ID NO:7 was bound to a Protein A column at pH7, then eluted with a buffer of pH5 to specifically elute the canine TNFR-HCB fusion protein dimer. The higher molecular weight aggregates of canine TNFR-HCB were subsequently eluted at pH4.5-4.7. The fractions were compared with the CHO cell expressed TNFR-HCB protein by SDS-PAGE (FIG. 29B). The original TNFR-HCB preparation, purified by standard pH3 elution, containing dimer and higher molecular weight aggregates is shown in Lanes 1 and 4. The pH5 eluate prepared according to the present invention (collected from run volume 25-45 mL in FIG. 29A), containing the purified dimer is shown in Lanes 2 and 5, whereas the aggregated forms eluted at lower pH (collected from run volumes 50-60 mL in FIG. 29A) are shown in lanes 3 and 6. The higher molecular weight aggregates were confirmed to be canine TNFR-HCB fusion protein by the identical banding pattern observed under reducing conditions (Lanes 4, 5 and 6). The improvement in purity of the canine TNFR-HCB fusion protein dimer is apparent by comparison of Lanes 1 and 2. Therefore, the novel pH5 Protein A elution conditions of the current invention have utility in preparing a higher purity canine TNFR-HCB fusion protein suitable for use as a therapeutic agent.

Example 4—A Novel Canine TNFR p80 Extracellular Domain Protein Sequence

FIG. 30 shows the derivation of a novel canine TNFR p80 extracellular domain amino acid sequence. By comparison with the human p80 extracellular domain sequence (P20333, in which the signal sequence is underlined), the derived sequences of two annotated variants of canine TNFR p80, clones XP_544562.2 and DN368636, were identified as incomplete versions of the TNFR p80, neither of which code for a complete canine TNFR p80 extracellular domain sequence that is capable of being expressed in a mammalian cell—clone XP_544562.2 (shown translated as far as the transmembrane domain in FIG. 30), by virtue of its lack of signal sequence and missing N-terminal sequence VPG, and Clone DN368636, by virtue of its lack of membrane proximal extracellular domain sequence and incorrect C-terminal sequence (TRRH). The combination of these two sequences results in a novel sequence for canine TNFR p80 ECD, which is shown as SEQ ID NO:14.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

```
Sequence Listing

SEQ ID NO: 1 (Canine TNFR p60 signal sequence and ECD)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGST SEQ ID NO: 2 (Canine IgG HCA heavy chain - hinge CH2, CH3)
FNECRCTDTPPCPVPEPLGGPSVLIFPPKPKDILRITRTPEVTCVVLDLGREDPEVQISWFVDGKE
VHTAKTQSREQQFNGTYRVVSVLPIEHQDWLTGKEFKCRVNHIDLPSPIERTISKARGRAHKPS
VYVLPPSPKELSSSDTVSITCLIKDFYPPDIDVEWQSNGQQEPERKHRMTPPQLDEDGSYFLYSK
LSVDKSRWQQGDPFTCAVMHETLQNHYTDLSLSHSPGK SEQ ID NO: 3 (Canine IgG HCB heavy chain - hinge CH2, CH3)
PKRENGRVPRPPDCPKCPAPEMLGGPSVFIFPPKPKDTLLIARTPEVTCVVVDLDPEDPEVQISW
FVDGKQMQTAKTQPREEQFNGTYRVVSVLPIGHQDWLKGKQFTCKVNNKALPSPIERTISKAR
GQAHQPSVYVLPPSREELSKNTVSLTCLIKDFYPPDIDVEWQSNGQQEPESKYRTTPPQLDEDGS
YFLYSKLSVDKSRWQRGDTFICAVMHEALHNHYTQESLSHSPGK SEQ ID NO: 4 (Canine IgG HCC heavy chain - hinge CH2, CH3)
AKECECKCNCNNCPCPGCGLLGGPSVFIFPPKPKDILVTARTPTVTCVVVDLDPENPEVQISWFV
DSKQVQTANTQPREEQSNGTYRVVSVLPIGHQDWLSGKQFKCKVNNKALPSPIEEIISKTPGQA
HQPNVYVLPPSRDEMSKNTVTLTCLVKDFFPPEIDVEWQSNGQQEPESKYRMTPPQLDEDGSY
FLYSKLSVDKSRWQRGDTFICAVMHEALHNHYTQISLSHSPGK SEQ ID NO: 5 (Canine IgG HCD heavy chain - hinge CH2, CH3)
PKESTCKCISPCPVPESLGGPSVFIFPPKPKDILRITRTPEITCVVLDLGREDPEVQISWFVDGKEV
```

HTAKTQPREQQFNSTYRVVSVLPIEHQDWLTGKEFKCRVNHIGLPSPIERTISKARGQAHQPSV
YVLPPSPKELSSSDTVTLTCLIKDFYPPEIDVEWQSNGQPEPESKYHTTAPQLDEDGSYFLYSKLS
VDKSRWQQGDTFTCAVMHEALQNHYTDLSLSHSPGK

SEQ ID NO: 6 (caTNFrecp60-HCA)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGSTFNECRCTDTPPCPVPEPLGGPSVLIFPPKPKDILRITRTPEVTCVVLDL
GREDPEVQISWFVDGKEVHTAKTQSREQQFNGTYRVVSVLPIEHQDWLTGKEFKCRVNHIDLP
SPIERTISKARGRAHKPSVYVLPPSPKELSSSDTVSITCLIKDFYPPDIDVEWQSNGQQEPERKHR
MTPPQLDEDGSYFLYSKLSVDKSRWQQGDPFTCAVMHETLQNHYTDLSLSHSPGK**

SEQ ID NO: 7 (caTNFrecp60-HCB)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGSTPKRENGRVPRPPDCPKCPAPEMLGGPSVFIFPPKPKDTLLIARTPEVT
CVVVDLDPEDPEVQISWFVDGKQMQTAKTQPREEQFNGTYRVVSVLPIGHQDWLKGKQFTCK
VNNKALPSPIERTISKARGQAHQPSVYVLPPSREELSKNTVSLTCLIKDFYPPDIDVEWQSNGQQ
EPESKYRTTPPQLDEDGSYFLYSKLSVDKSRWQRGDTFICAVMHEALHNHYTQESLSHSPGK**

SEQ ID NO: 8 (caTNFrecp60-HCC)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGSTAKECECKCNCNNCPCPGCGLLGGPSVFIFPPKPKDILVTARTPTVTCV
VVDLDPENPEVQISWFVDSKQVQTANTQPREEQSNGTYRVVSVLPIGHQDWLSGKQFKCKVNN
KALPSPIEEIISKTPGQAHQPNVYVLPPSRDEMSKNTVTLTCLVKDFFPPEIDVEWQSNGQQEPE
SKYRMTPPQLDEDGSYFLYSKLSVDKSRWQRGDTFICAVMHEALHNHYTQISLSHSPGK**

SEQ ID NO: 9 (caTNFrecp60-HCD)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGSTPKESTCKCISPCVPESLGGPSVFIFPPKPKDILRITRTPEITCVVLDLG
REDPEVQISWFVDGKEVHTAKTQPREQQFNSTYRVVSVLPIEHQDWLTGKEFKCRVNHIGLPSP
IERTISKARGQAHQPSVYVLPPSPKELSSSDTVTLTCLIKDFYPPEIDVEWQSNGQPEPESKYHTT
APQLDEDGSYFLYSKLSVDKSRWQQGDTFTCAVMHEALQNHYTDLSLSHSPGK**

SEQ ID NO: 10 (caTNFrecp60-aglycosyl HCA)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGSTFNECRCTDTPPCPVPEPLGGPSVLIFPPKPKDILRITRTPEVTCVVLDL
GREDPEVQISWFVDGKEVHTAKTQSREQQFAGTYRVVSVLPIEHQDWLTGKEFKCRVNHIDLP
SPIERTISKARGRAHKPSVYVLPPSPKELSSSDTVSITCLIKDFYPPDIDVEWQSNGQQEPERKHR
MTPPQLDEDGSYFLYSKLSVDKSRWQQGDPFTCAVMHETLQNHYTDLSLSHSPGK**

SEQ ID NO: 11 (caTNFrecp60-aglycosyl HCB)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGSTPKRENGRVPRPPDCPKCPAPEMLGGPSVFIFPPKPKDTLLIARTPEVT
CVVVDLDPEDPEVQISWFVDGKQMQTAKTQPREEQFAGTYRVVSVLPIGHQDWLKGKQFTCK
VNNKALPSPIERTISKARGQAHQPSVYVLPPSREELSKNTVSLTCLIKDFYPPDIDVEWQSNGQQ
EPESKYRTTPPQLDEDGSYFLYSKLSVDKSRWQRGDTFICAVMHEALHNHYTQESLSHSPGK**

SEQ ID NO: 12 (caTNFrecp60-aglycosyl HCC)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGSTAKECECKCNCNNCPCPGCGLLGGPSVFIFPPKPKDILVTARTPTVTCV
VVDLDPENPEVQISWFVDSKQVQTANTQPREEQSAGTYRVVSVLPIGHQDWLSGKQFKCKVNN
KALPSPIEEIISKTPGQAHQPNVYVLPPSRDEMSKNTVTLTCLVKDFFPPEIDVEWQSNGQQEPE
SKYRMTPPQLDEDGSYFLYSKLSVDKSRWQRGDTFICAVMHEALHNHYTQISLSHSPGK**

SEQ ID NO: 13 (caTNFrecp60-aglycosyl HCD)
MGLPTVPGLLLPLVLLALLLEIYPISVTALVPHPRNRVKRAILCPQGKYIHPQDDSICCTKCHKGT
YLYNDCPGPGLDTDCRECENGTFTASENHLRQCLSCSKCRKEMNQVEISPCTVYRDTVCGCRKN
QYRFYWSETLFQCNNCSLCLNGTVQISCQEKQNTICTCHAGFFLREHECVSCVNCKKNTECGKL
CLPPVETVKVPQDPGSTPKESTCKCISPCVPESLGGPSVFIFPPKPKDILRITRTPEITCVVLDLG
REDPEVQISWFVDGKEVHTAKTQPREQQFASTYRVVSVLPIEHQDWLTGKEFKCRVNHIGLPSP
IERTISKARGQAHQPSVYVLPPSPKELSSSDTVTLTCLIKDFYPPEIDVEWQSNGQPEPESKYHTT
APQLDEDGSYFLYSKLSVDKSRWQQGDTFTCAVMHEALQNHYTDLSLSHSPGK**

SEQ ID NO: 14 (Canine TNFR p80 signal sequence and ECD)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGD SEQ ID NO: 15 (caTNFrecp80-HCA)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGDFNECRCTDTPPCPVPEPLGGPSVLIFPPKPKDILRITRTPEVTCVVLDLGREDPEVQISW
FVDGKEVHTAKTQSREQQFNGTYRVVSVLPIEHQDWLTGKEFKCRVNHIDLPSPIERTISKARG
RAHKPSVYVLPPSPKELSSSDTVSITCLIKDFYPPDIDVEWQSNGQQEPERKHRMTPPQLDEDGS
YFLYSKLSVDKSRWQQGDPFTCAVMHETLQNHYTDLSLSHSPGK**

SEQ ID NO: 16 (caTNFrecp80-HCB)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGDPKRENGRVPRPPDCPKCPAPEMLGGPSVFIFPPKPKDTLLIARTPEVTCVVVDLDPEDP
EVQISWFVDGKQMTAKTQPREEQFNGTYRVVSVLPIGHQDWLKGKQFTCKVNNKALPSPIER
TISKARGQAHQPSVYVLPPSREELSKNTVSLTCLIKDFYPPDIDVEWQSNGQQEPESKYRTTPPQ
LDEDGSYFLYSKLSVDKSRWQRGDTFICAVMHEALHNHYTQESLSHSPGK**

SEQ ID NO: 17 (caTNFrecp80-HCC)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGDAKECECKCNCNNCPCPGCGLLGGPSVFIFPPKPKDILVTARTPTVTCVVVDLDPENPEV
QISWFVDSKQVQTANTQPREEQSNGTYRVVSVLPIGHQDWLSGKQFKCKVNNKALPSPIEEIISK
TPGQAHQPNVYVLPPSRDEMSKNTVTLTCLVKDFFPPEIDVEWQSNGQQEPESKYRMTPPQLD
EDGSYFLYSKLSVDKSRWQRGDTFICAVMHEALHNHYTQISLSHSPGK**

SEQ ID NO: 18 (caTNFrecp80-HCD)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGDPKESTCKCISPCPVPESLGGPSVFIFPPKPKDILRITRTPEITCVVLDLGREDPEVQISWF
VDGKEVHTAKTQPREQQFNSTYRVVSVLPIEHQDWLTGKEFKCRVNHIGLPSPIERTISKARGQ
AHQPSVYVLPPSPKELSSSDTVTLTCLIKDFYPPEIDVEWQSNGQPEPESKYHTTAPQLDEDGSY
FLYSKLSVDKSRWQQGDTFTCAVMHEALQNHYTDLSLSHSPGK**

SEQ ID NO: 19 (caTNFrecp80-aglycosyl HCA)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGDFNECRCTDTPPCPVPEPLGGPSVLIFPPKPKDILRITRTPEVTCVVLDLGREDPEVQISW
FVDGKEVHTAKTQSREQQFAGTYRVVSVLPIEHQDWLTGKEFKCRVNHIDLPSPIERTISKARG
RAHKPSVYVLPPSPKELSSSDTVSITCLIKDFYPPDIDVEWQSNGQQEPERKHRMTPPQLDEDGS
YFLYSKLSVDKSRWQQGDPFTCAVMHETLQNHYTDLSLSHSPGK**

SEQ ID NO: 20 (caTNFrecp80-aglycosyl HCB)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGDPKRENGRVPRPPDCPKCPAPEMLGGPSVFIFPPKPKDTLLIARTPEVTCVVVDLDPEDP
EVQISWFVDGKQMTAKTQPREEQFAGTYRVVSVLPIGHQDWLKGKQFTCKVNNKALPSPIER
TISKARGQAHQPSVYVLPPSREELSKNTVSLTCLIKDFYPPDIDVEWQSNGQQEPESKYRTTPPQ
LDEDGSYFLYSKLSVDKSRWQRGDTFICAVMHEALHNHYTQESLSHSPGK**

SEQ ID NO: 21 (caTNFrecp80-aglycosyl HCC)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGDAKECECKCNCNNCPCPGCGLLGGPSVFIFPPKPKDILVTARTPTVTCVVVDLDPENPEV
QISWFVDSKQVQTANTQPREEQSAGTYRVVSVLPIGHQDWLSGKQFKCKVNNKALPSPIEEIISK
TPGQAHQPNVYVLPPSRDEMSKNTVTLTCLVKDFFPPEIDVEWQSNGQQEPESKYRMTPPQLD
EDGSYFLYSKLSVDKSRWQRGDTFICAVMHEALHNHYTQISLSHSPGK**

Sequence Listing

SEQ ID NO: 22 (caTNFrecp80-aglycosyl HCD)
MAPAALWALLAAGLQLWGAGRAVPGQATQLPYVPDPELGSSCQQSEYFDQRTQMCCSMCPPG
SHARLFCTKTSNTVCARCENSTYTQLWNWVPECLSCGSRCGADQVETQACTREQNRICSCKSG
WYCTLRRQGGCRLCAPLRRCRPGFGVAKPGTATSDVVCAPCAPGTFSNTTSSTDTCRPHRICSS
VAVPGNASVDAVCSPAPPTVRTAPRPASTRQPGSTQPRPAEPTPGPSTPPRTSVLFPAVPSPPAE
GLSTGDPKESTCKCISPCPVPESLGGPSVFIFPPKPKDILRITRTPEITCVVLDLGREDPEVQISWF
VDGKEVHTAKTQPREQQFASTYRVVSVLPIEHQDWLTGKEFKCRVNHIGLPSPIERTISKARGQ
AHQPSVYVLPPSPKELSSSDTVTLTCLIKDFYPPEIDVEWQSNGQPEPESKYHTTAPQLDEDGSY
FLYSKLSVDKSRWQQGDTFTCAVMHEALQNHYTDLSLSHSPGK**

The invention claimed is:

1. A chimeric fusion polypeptide comprising (i) a canine tumor necrosis factor receptor (TNFR) p80 extracellular domain polypeptide that specifically binds to canine TNF, or a canine TNF-binding fragment thereof, conjoined to (ii) a polypeptide comprising a CH2 constant domain and a CH3 constant domain of canine IgG immunoglobulin, wherein the p80 extracellular domain polypeptide comprises amino acid residues 23 to 260 of SEQ ID NO:14, or a sequence having at least 90% sequence identity thereto, wherein the N-terminal amino sequence of the chimeric fusion polypeptide comprises the N-terminal VPGQ motif of the p80 extracellular domain polypeptide.

2. The chimeric fusion polypeptide as claimed in claim 1, wherein the p80 extracellular domain polypeptide, or the TNF-binding fragment thereof, is conjoined to a polypeptide comprising a hinge region, a CH2 constant domain and a CH3 constant domain of canine IgG immunoglobulin.

3. The chimeric fusion polypeptide as claimed in claim 1, wherein the chimeric fusion polypeptide comprises a linker peptide functionally interposed between the canine p80 extracellular domain polypeptide and the polypeptide comprising the CH2 and CH3 constant domains.

4. The chimeric fusion polypeptide as claimed in claim 1, wherein the p80 extracellular domain polypeptide comprises amino acid residues 23 to 260 of SEQ ID NO:14.

5. The chimeric fusion polypeptide as claimed in claim 4, wherein the p80 extracellular domain polypeptide consists of amino acid residues 23 to 260 of SEQ ID NO:14.

6. The chimeric fusion polypeptide as claimed in claim 1, wherein the p80 extracellular domain polypeptide, or the TNF-binding fragment thereof, is conjoined to a polypeptide comprising the CH2 and CH3 constant domains of a canine IgG isotype selected from the group consisting of subtype A, subtype D and an aglycolsylated version of subtypes A, B, C and D.

7. The chimeric fusion polypeptide as claimed in claim 1, wherein the p80 extracellular domain polypeptide, or the TNF-binding fragment thereof, is conjoined to a polypeptide comprising an amino acid sequence selected from the group consisting of SEQ ID NO:2, SEQ ID NO:3, SEQ ID NO:4 and SEQ ID NO:5.

8. The chimeric fusion polypeptide as claimed in claim 1 comprising an amino acid sequence selected from the group consisting of:

a) amino acid residues 23 to 493 of SEQ ID NO:15;
 b) amino acid residues 23 to 497 of SEQ ID NO:16;
 c) amino acid residues 23 to 495 of SEQ ID NO:17;
 d) amino acid residues 23 to 493 of SEQ ID NO:18; and
 e) a sequence having at least 90% sequence identity to any of (a) to (d).

9. The chimeric fusion polypeptide as claimed in claim 8, wherein the chimeric fusion polypeptide consists of an amino acid sequence selected from the group consisting of:

a) amino acid residues 23 to 493 of SEQ ID NO:15;
 b) amino acid residues 23 to 497 of SEQ ID NO:16;
 c) amino acid residues 23 to 495 of SEQ ID NO:17; and
 d) amino acid residues 23 to 493 of SEQ ID NO:18.

10. The chimeric fusion polypeptide as claimed in claim 1 comprising an amino acid sequence selected from the group consisting of:

a) amino acid residues 23 to 493 of SEQ ID NO:19;
 b) amino acid residues 23 to 497 of SEQ ID NO:20;
 c) amino acid residues 23 to 495 of SEQ ID NO:21;
 d) amino acid residues 23 to 493 of SEQ ID NO:22; and
 e) a sequence having at least 90% sequence identity to any of (a) to (d).

11. The chimeric fusion polypeptide as claimed in claim 10, wherein the chimeric fusion polypeptide consists of an amino acid sequence selected from the group consisting of:

a) amino acid residues 23 to 493 of SEQ ID NO:19;
 b) amino acid residues 23 to 497 of SEQ ID NO:20;
 c) amino acid residues 23 to 495 of SEQ ID NO:21; and
 d) amino acid residues 23 to 493 of SEQ ID NO:22.

12. A pharmaceutical composition comprising the chimeric fusion polypeptide as claimed in claim 1, and a pharmaceutically acceptable carrier or excipient.

13. An isolated canine tumor necrosis factor receptor (TNFR) p80 polypeptide that specifically binds to canine TNF, or a canine TNF-binding fragment thereof, wherein the polypeptide comprises amino acid residues 23 to 260 of SEQ ID NO:14, or a sequence having at least 90% sequence identity thereto, wherein the N-terminal amino sequence of the polypeptide comprises the N-terminal VPGQ motif of amino acid residues 23 to 260 of SEQ ID NO:14.

14. The polypeptide as claimed in claim 13 consisting of amino acid residues 23 to 260 of SEQ ID NO:14.

* * * * *